(12) United States Patent
Yasuma et al.

(10) Patent No.: US 7,456,218 B2
(45) Date of Patent: Nov. 25, 2008

(54) 3-(4-BENZYLOXYPHENYL) PROPANOIC ACID DERIVATIVES

(75) Inventors: Tsuneo Yasuma, Osaka (JP); Shuji Kitamura, Osaka (JP); Nobuyuki Negoro, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 83 days.

(21) Appl. No.: 10/584,481

(22) PCT Filed: Dec. 24, 2004

(86) PCT No.: PCT/JP2004/019741

§ 371 (c)(1),
(2), (4) Date: Jun. 23, 2006

(87) PCT Pub. No.: WO2005/063729

PCT Pub. Date: Jul. 14, 2005

(65) Prior Publication Data

US 2007/0149608 A1    Jun. 28, 2007

(30) Foreign Application Priority Data

Dec. 25, 2003    (JP)    ............................. 2003-431629
Aug. 20, 2004    (JP)    ............................. 2004-241484

(51) Int. Cl.
 *A61K 31/192*    (2006.01)
 *C07C 51/09*    (2006.01)
(52) U.S. Cl. ...................... 514/568; 562/407
(58) Field of Classification Search ................. 514/568; 562/407
See application file for complete search history.

(56) References Cited

FOREIGN PATENT DOCUMENTS

| JP | 2003-261491 | 9/2003 |
|---|---|---|
| WO | 97/31907 | 9/1997 |
| WO | 99/11255 | 3/1999 |
| WO | 00/64876 | 11/2000 |
| WO | 01/00603 | 1/2001 |
| WO | 01/55085 | 8/2001 |
| WO | 01/79150 | 10/2001 |
| WO | 02/053547 | 7/2002 |
| WO | 02/083616 | 10/2002 |
| WO | 02/092590 | 11/2002 |
| WO | 02/100813 | 12/2002 |
| WO | 03/018553 | 3/2003 |
| WO | 03/084916 | 10/2003 |
| WO | 03/099793 | 12/2003 |
| WO | 2004/000315 | 12/2003 |
| WO | 2004/041266 | 5/2004 |
| WO | 2004/091604 | 10/2004 |

OTHER PUBLICATIONS

Y. Itoh et al., "Free fatty acids regulate insulin secretion from pancreatic β cells through GPR40", Nature, vol. 422, No. 6928, pp. 173-176, Mar. 13, 2003.

*Primary Examiner*—Taofiq A Solola
(74) *Attorney, Agent, or Firm*—Wenderoth, Lind & Ponack, L.L.P.

(57) ABSTRACT

The present invention provides a novel compound represented by the formula (I) wherein each symbol is as defined in the specification, a salt thereof and a prodrug thereof having a superior GPR40 receptor function modulating action, which can be used as an insulin secretagogue, an agent for the prophylaxis or treatment of diabetes and the like. They unexpectedly show superior GPR40 receptor agonist activity, and also show superior properties as a pharmaceutical product, such as stability and the like. Thus, they can be safe and useful pharmaceutical agents for the prophylaxis or treatment of GPR40 receptor related diseases in mammals.

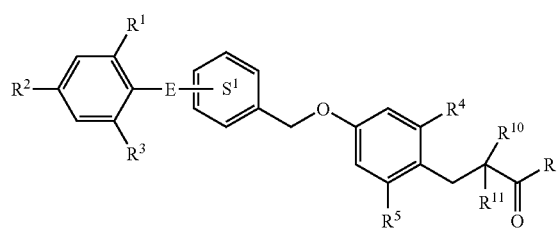

15 Claims, No Drawings

3-(4-BENZYLOXYPHENYL) PROPANOIC ACID DERIVATIVES

This application is a U.S. national stage of International Application No. PCT/JP2004/019741 filed Dec. 24, 2004.

1. Technical Field

The present invention relates to a novel compound having GPR40 receptor function modifying action and which is useful as an agent for the prophylaxis or treatment of diabetes.

2. Background Art

It has been reported in recent years that a ligand of GPR40, which is one of the G Protein-Coupled Receptors (GPCR), is fatty acid and GPR40 in pancreatic β cell is deeply involved in insulin secretion action (Nature, 2003, vol. 422, pages 173-176). Thus, a GPR40 agonist promotes insulin secretion, a GPR40 antagonist inhibits insulin secretion, and the agonist and the antagonist are useful as an agent for the prophylaxis or treatment of type 2 diabetes, obesity, impaired glucose tolerance, insulin resistance, neurodegenerative diseases (Alzheimer's disease) and the like (WO03/068959 and WO02/057783).

On the other hand, many compounds useful as an agent for the prophylaxis or treatment of diabetes have been reported.

For example, WO02/092590 discloses that a peroxisome proliferator activated receptor (PPAR) modulator represented by the formula:

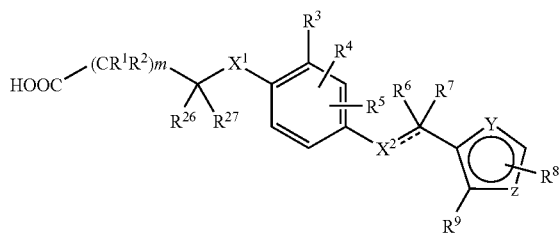

wherein $X^1$: a $C_{1-3}$ alkyl and the like; $R^1$, $R^2$: H and the like; $R^3$, $R^4$, $R^5$: H, $CH_3$ and the like; $R^{26}$, $R^{27}$: H and the like; m: 0-3; $X^2$: O and the like; $R^6$, $R^7$: H and the like; Y, Z: one is CH and the other is S or O; $R^8$: a phenyl and the like; $R^9$: a $C_{1-6}$ alkyl and the like, is useful as an agent for the prophylaxis or treatment of PPAR mediated disease (e.g., diabetes).

WO02/053547 discloses that an alkanoic acid derivative represented by the formula:

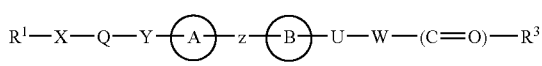

wherein $R^1$: an optionally substituted 5-membered aromatic heterocyclic group; X: a bond, O, S, —$NR^6$— ($R^6$: H, an optionally substituted hydrocarbon group and the like) and the like; Q: a divalent $C_{1-20}$ hydrocarbon group; Y: a bond, O, S, —$NR^7$— ($R^7$: H, an optionally substituted hydrocarbon group and the like) and the like; ring A: an aromatic ring optionally further having 1 to 3 substituent(s); Z: —$(CH_2)n$-$Z^1$- (n: 1-8, $Z^1$: O and the like) and the like; ring B: a benzene ring optionally further having 1 to 3 substituent(s) and the like; U: a bond and the like; W: a divalent $C_{1-20}$ hydrocarbon group; $R^3$: —$OR^8$— ($R^8$: H, an optionally substituted hydrocarbon group) or —$NR^9R^{10}$— ($R^9$, $R^{10}$: H, an optionally substituted hydrocarbon group and the like) and the like; provided that when ring B is a benzene ring optionally further having 1 to 3 substituent(s), then U is a bond, is useful as an agent for the prophylaxis or treatment of diabetes, hyperlipidemia, impaired glucose tolerance and the like.

WO99/11255 discloses that a compound represented by the formula:

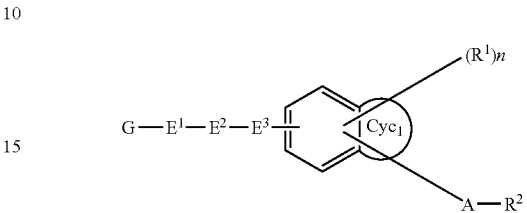

wherein $R^1$: a $C_{1-8}$ alkyl, a $C_{1-8}$ alkoxy, a halogen atom, a trifluoromethyl and the like; $R^2$: —$COOR^3$ ($R^3$: H, a $C_{1-4}$ alkyl) and the like; A: a $C_{1-8}$ alkylene and the like; G: a carbon ring optionally substituted by a $C_{1-8}$ alkyl, a $C_{1-8}$ alkoxy, a halogen atom, a trifluoromethyl or a nitro, and the like; $E^1$: a $C_{1-8}$ alkylene and the like; $E^2$: —O— and the like; $E^3$: a single bond and the like; n: 0, 1; Cyc1 ring: absent and the like, has a PPAR receptor regulating action, and is useful as an agent for the prophylaxis or treatment of metabolism abnormality diseases such as diabetes, obesity, syndrome X, hypercholesterolemia, hyperlipoproteinemia and the like, and the like.

WO00/64876 discloses that a compound represented by the formula:

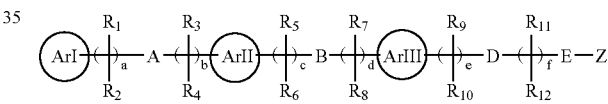

wherein ring ArI, ring ArII, ring ArIII: an optionally substituted aryl and the like; A: —O—, —S—, a bond, —$NR_{13}$— ($R_{13}$: H, an alkyl and the like) and the like; B: —O— and the like; D: a bond, an ethylene; E: a bond, an ethylene; Z: $R_{21}O_2C$—, $(R_{21})_2NCO$— ($R_{21}$: H, an alkyl and the like) and the like; a, b, c, e: 0-4; d: 0-5; f: 0-6; $R_1$-$R_{12}$: H and the like, is useful as a PPAR ligand receptor binder, PPAR receptor agonist or PPAR receptor antagonist, and can be used as an agent for the treatment of diabetes.

WO01/00603 discloses that a compound represented by the formula:

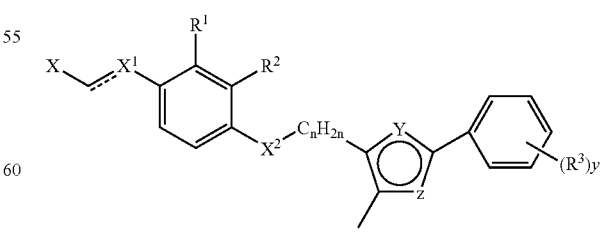

wherein X: COOH (containing ester) and the like; $X^1$: $CH_2$ etc.; dotted line shows double bond only when $X^1$ is CH; $X^2$: O and the like; $R^1$, $R^2$: H, Me and the like; n: 1, 2; Y, Z: one is N and the other is S or O; y: an integer of 0-5; $R^3$: $CF_3$ and the like, can be used as a PPARδ agonist, and is useful as an agent for the prophylaxis or treatment of PPARδ mediated disease (e.g., hyperlipidemia, arteriosclerosis, type I or II diabetes and the like).

WO97/31907 discloses that a compound represented by the formula:

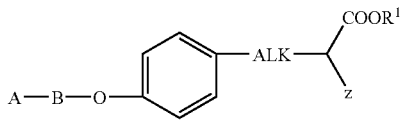

wherein A: a phenyl optionally substituted a halogen and the like, and the like; B: a $C_{1-6}$ alkylene and the like; ALK: a $C_{1-3}$ alkylene; $R^1$: H, a $C_{1-3}$ alkyl; Z: —($C_{1-3}$ alkylene)phenyl optionally substituted by a halogen and the like, is useful as a PPARγ agonist, can be used as an agent for the prophylaxis or treatment of hyperglycemia, type I or II diabetes, hyperlipidemia and the like.

WO02/083616 discloses that a compound represented by the formula:

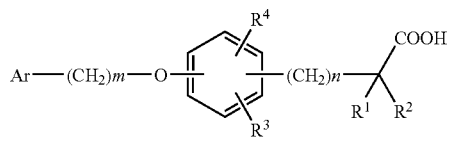

wherein Ar: a phenyl substituted by 1 to 5 the same or different halogen atom(s) and the like, and the like; $R^1$: a halogen atom and the like; $R^2$: H and the like; $R^3$, $R^4$: H, a halogen atom; m: 1, 2; n: 2-7, has a superior insulin sensitizing action, hypoglycemic action, hypolipidemic action, antiinflammatory action, immunomodulating action, lipoperoxide production suppressive action and PPAR activating action, and is useful as an agent for the treatment of diabetes.

WO01/55085 discloses that a compound represented by the formula:

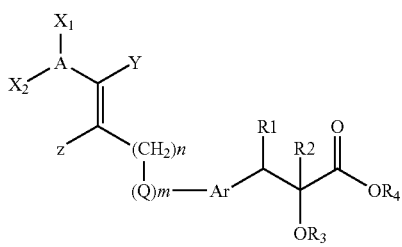

wherein A: an aryl optionally substituted by OH and the like; $X^1$, $X^2$: H and the like; Y, Z: H and the like; n: 0-3; m: 0, 1; Q: O and the like; Ar: an arylene and the like; $R^1$-$R^4$: H and the like, is useful as an agent for the treatment of PPAR related diseases, and useful as an agent for the treatment of, for example, type 2 diabetes, impaired glucose tolerance, insulin resistance, hypertriglyceridemia and the like.

However, it has not been disclosed at all that these known therapeutic drugs for diabetes have a GPR40 receptor function modifying action, and there is no report on a compound having a GPR40 receptor function modifying action (compound useful as a GPR40 agonist or GPR40 antagonist). Under the circumstances, development of a compound having a GPR40 receptor function modifying action has been desired.

DISCLOSURE OF THE INVENTION

The present invention aims at providing a novel compound having a GPR40 receptor function modifying action, which is useful as an insulin secretagogue or an agent for the prophylaxis or treatment of diabetes and the like.

The present inventors have intensively conducted various studies and found that the compound represented by the following formula (I) unexpectedly has a superior GPR40 receptor agonist activity, shows superior properties as a pharmaceutical product such as stability and the like, and can be a safe and useful pharmaceutical agent for the prophylaxis or treatment of GPR40 receptor related disease state or diseases in mammal, and completed the present invention.

Accordingly, the present invention provides the following.

(1) A compound represented by the formula (I):

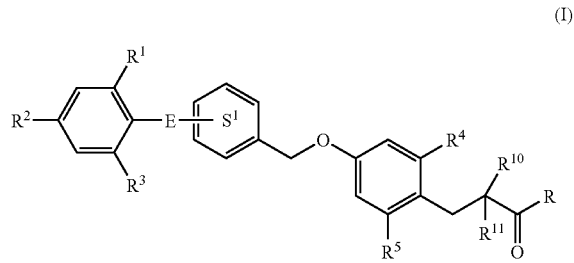

wherein $R^1$, $R^3$, $R^4$ and $R^5$
are the same or different and each is a hydrogen atom, a halogen atom, an optionally substituted hydrocarbon group or an optionally substituted hydroxy group;

$R^2$ is a halogen atom, a nitro group, an optionally substituted hydrocarbon group, an optionally substituted hydroxy group, an optionally substituted amino group, an optionally substituted mercapto group, an optionally substituted acyl group or an optionally substituted heterocyclic group;

$R^{10}$ and $R^{11}$ are the same or different and each is a hydrogen atom, a halogen atom or a $C_{1-6}$ alkoxy group;

E is a bond, an optionally substituted $C_{1-4}$ alkylene group, —$W^1$—O—$W^2$—, —$W^1$—S—$W^2$— or —$W^1$—N($R^6$)—$W^2$— (wherein $W^1$ and $W^2$ are the same or different and each is a bond or an optionally substituted $C_{1-3}$ alkylene group, and $R^6$ is a hydrogen atom, an optionally substituted acyl group or an optionally substituted hydrocarbon group);

ring $S^1$ is a benzene ring optionally further having substituent(s) selected from a halogen atom, an optionally substituted hydrocarbon group, an optionally substituted hydroxy group and an optionally substituted amino group; and R is an optionally substituted hydroxy group or an optionally substituted amino group;

provided that $R^1$ and $R^3$ are not simultaneously a hydrogen atom, or a salt thereof.

(2) The compound of (1) above, wherein $R^2$ is a halogen atom, an optionally substituted hydrocarbon group, an optionally substituted hydroxy group, an optionally substituted amino group, an optionally substituted mercapto group or an optionally substituted heterocyclic group, and $R^{10}$ and $R^{11}$ are both hydrogen atoms, or a salt thereof.

(3) A prodrug of a compound of (1) above or a salt thereof.

(4) The compound of (1) above, wherein $R^4$ and $R^5$ are the same or different and each is a hydrogen atom or a halogen atom, or a salt thereof.

(5) The compound of (1) above, wherein E is a bond, or a salt thereof.

(6) The compound of (1) above, wherein R is a hydroxy group, or a salt thereof.

(7) The compound of (1) above, wherein $R^1$ and $R^3$ are the same or different and each is a $C_{1-6}$ alkyl group, or a salt thereof.

(8) The compound of (1) above, wherein $R^2$ is an optionally substituted hydroxy group, or a salt thereof.

(9) The compound of (1) above, wherein $R^{10}$ and $R^{11}$ are both hydrogen atoms, or a salt thereof.

(10) The compound of (1) above, wherein ring $S^1$ is a benzene ring optionally further having a $C_{1-6}$ alkoxy group, or a salt thereof.

(11) 3-[4-[[4'-(Benzyloxy)-2',6'-dimethylbiphenyl-3-yl] methoxy]phenyl]propanoic acid;

3-(4-{[4'-(2-ethoxyethoxy)-2',6'-dimethylbiphenyl-3-yl] methoxy}phenyl)-2,2-difluoropropanoic acid;

3-[4-({4'-[2-(ethylsulfonyl)ethoxy]-2',6'-dimethylbiphenyl-3-yl}methoxy)-2-fluorophenyl]propanoic acid;

3-[4-({2',6'-dimethyl-4'-[3-(2-oxopyrrolidin-1-yl)propoxy] biphenyl-3-yl}methoxy)-2-fluorophenyl]propanoic acid;

3-[4-({2',6'-dimethyl-4'-[(6-methylpyridin-2-yl)methoxy] biphenyl-3-yl}methoxy)-2-fluorophenyl]propanoic acid;

3-[2-fluoro-4-({4'-[(4-hydroxy-1,1-dioxidotetrahydro-2H-thiopyran-4-yl)methoxy]-2',6'-dimethylbiphenyl-3-yl}methoxy)phenyl]propanoic acid;

3-[4-({2',6'-dimethyl-4'-[(methylsulfonyl)oxy]biphenyl-3-yl}methoxy)-2-fluorophenyl]propanoic acid;

3-[4-({4'-[(1,1-dioxidotetrahydro-2H-thiopyran-4-yl)oxy]-2',6'-dimethylbiphenyl-3-yl}methoxy)-2-fluorophenyl] propanoic acid;

3-[4-({2',6'-dimethyl-4'-[(3-methyloxetan-3-yl)methoxy]biphenyl-3-yl}methoxy)-2-fluorophenyl]propanoic acid;

3-(4-{[2',6'-dimethyl-4'-(tetrahydro-2H-pyran-4-yloxy)biphenyl-3-yl]methoxy}-2-fluorophenyl)propanoic acid;

3-[4-({4'-[3-(diethoxyphosphoryl)propoxy]-2',6'-dimethylbiphenyl-3-yl}methoxy)-2-fluorophenyl]propanoic acid;

3-[2-fluoro-4-({6-isopropoxy-2',6'-dimethyl-4'-[(3-methyloxetan-3-yl)methoxy]biphenyl-3-yl}methoxy)phenyl] propanoic acid;

or a salt thereof.

(12) A GPR40 receptor function modulator comprising a compound of (1) above or a salt thereof or a prodrug thereof.

(13) A pharmaceutical agent comprising a compound of (1) above or a salt thereof or a prodrug thereof.

(14) The pharmaceutical agent of (13) above, which is an agent for the prophylaxis or treatment of diabetes.

(15) Use of a compound of (1) above or a salt thereof or a prodrug thereof for the production of a GPR40 receptor function modulator.

(16) Use of a compound of (1) above or a salt thereof or a prodrug thereof for the production of an agent for the prophylaxis or treatment of diabetes.

(17) A method of modifying a GPR40 receptor function in a mammal, which comprises administering an effective amount of a compound of (1) above or a salt thereof or a prodrug thereof to the mammal.

(18) A method for the prophylaxis or treatment of diabetes in a mammal, which comprises administering an effective amount of a compound of (1) above or a salt thereof or a prodrug thereof to the mammal.

(19) A production method of a compound represented by the formula (Ib):

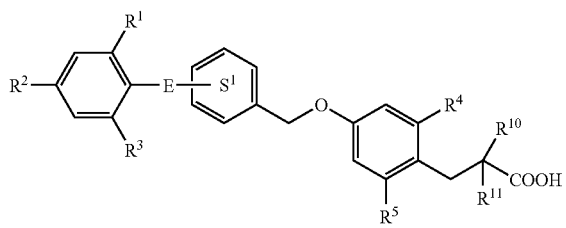

(Ib)

wherein $R^1$, $R^2$, $R^3$, $R^4$, $R^5$, $R^{10}$, $R^{11}$, E and ring $S^1$ are as defined in (1) above, or a salt thereof, which comprises reacting a compound represented by the formula (X):

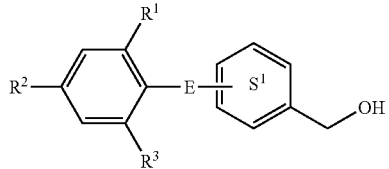

(X)

wherein each symbol is as defined above, or a salt thereof, and a compound represented by the formula (II):

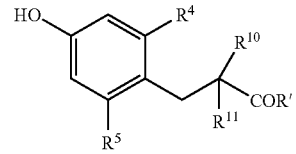

(II)

wherein $R^4$, $R^5$, $R^{10}$ and $R^{11}$ are as defined above, and R' is an optionally substituted $C_{1-6}$ alkoxy group, or a salt thereof, to give a compound represented by the formula (Ib'):

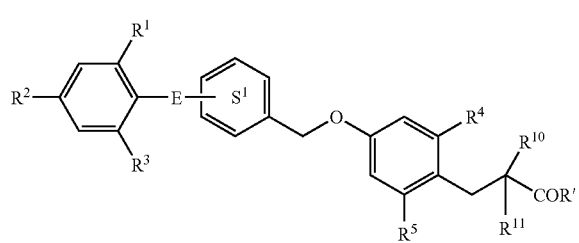

(Ib')

wherein each symbol is as defined above, or a salt thereof, and subjecting the compound or a salt thereof to a hydrolysis reaction.

(20) A production method of a compound represented by the formula (Id):

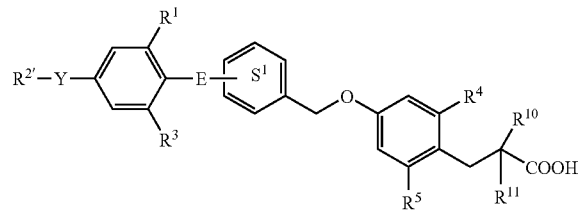
(Id)

wherein $R^1$, $R^3$, $R^4$, $R^5$, $R^{10}$, $R^{11}$, E and ring $S^1$ are as defined in (1) above, Y is —O— or —S—, and $R^{2'}$ is a substituent, or a salt thereof, which comprises reacting a compound represented by the formula (Ie'):

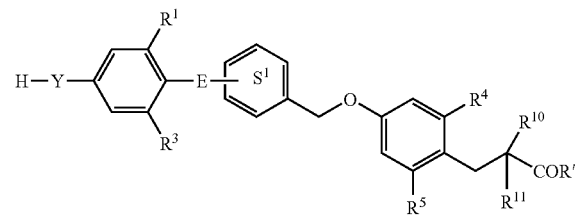
(Ie')

wherein $R^1$, $R^3$, $R^4$, $R^5$, $R^{10}$, $R^{11}$, E, Y and ring $S^1$ are as defined above; R' is as defined in (19) above, or a salt thereof, and a compound represented by the formula:

$R^{2'}$—OH wherein $R^{2'}$ is as defined above, or a salt thereof, to give a compound represented by the formula (If'):

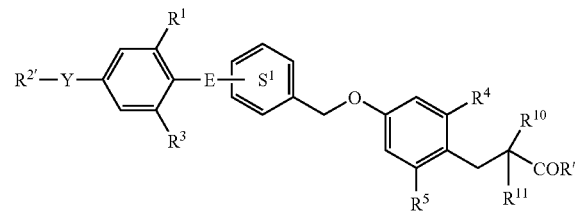
(If')

wherein each symbol is as defined above, or a salt thereof, and subjecting the compound or a salt thereof to a hydrolysis reaction.

The compound of the present invention has a superior GPR40 receptor function modifying action, and can be used as an agent for the prophylaxis or treatment of diabetes and the like.

BEST MODE FOR CARRYING OUT THE INVENTION

Unless otherwise specified, as the "halogen atom" in the present specification, fluorine atom, chlorine atom, bromine atom, iodine atom can be mentioned.

Unless otherwise specified, as the "optionally substituted hydrocarbon group" in the present specification, for example, "optionally substituted $C_{1-6}$ alkyl group", "optionally substituted $C_{2-6}$ alkenyl group", "optionally substituted $C_{2-6}$ alkynyl group", "optionally substituted $C_{3-8}$ cycloalkyl group", "optionally substituted $C_{6-14}$ aryl group", "optionally substituted $C_{7-16}$ aralkyl group" and the like can be mentioned.

Unless otherwise specified, as the "$C_{1-6}$ alkyl group" in the present specification, for example, methyl, ethyl, propyl, isopropyl, butyl, isobutyl, sec-butyl, tert-butyl, pentyl, isopentyl, neopentyl, hexyl and the like can be mentioned.

Unless otherwise specified, as the "$C_{2-6}$ alkenyl group" in the present specification, for example, vinyl, propenyl, isopropenyl, 2-buten-1-yl, 4-penten-1-yl, 5-hexen-1-yl and the like can be mentioned.

Unless otherwise specified, as the "$C_{2-6}$ alkynyl group" in the present specification, for example, 2-butyn-1-yl, 4-pentyn-1-yl, 5-hexyn-1-yl and the like can be mentioned.

Unless otherwise specified, as the "$C_{3-8}$ cycloalkyl group" in the present specification, for example, cyclopropyl, cyclobutyl, cyclopentyl, cyclohexyl and the like can be mentioned.

Unless otherwise specified, as the "$C_{6-14}$ aryl group" in the present specification, for example, phenyl, 1-naphthyl, 2-naphthyl, 2-biphenylyl, 3-biphenylyl, 4-biphenylyl, 2-anthryl and the like can be mentioned. The $C_{6-14}$ aryl may be optionally saturated partially, and as the partially saturated $C_{6-14}$ aryl, for example, tetrahydronaphthyl and the like can be mentioned.

Unless otherwise specified, as the "$C_{7-16}$ aralkyl group" in the present specification, for example, benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl and the like can be mentioned.

Unless otherwise specified, as the "optionally substituted hydroxy group" in the present specification, for example, "hydroxy group", "optionally substituted $C_{1-10}$ alkoxy group", "optionally substituted heterocyclyloxy group", "optionally substituted $C_{6-14}$ aryloxy group", "optionally substituted $C_{7-16}$ aralkyloxy group", "tri-$C_{1-6}$ alkyl-silyloxy group", "optionally substituted $C_{1-6}$ alkylsulfonyloxy group", "optionally substituted heterocyclylsulfonyloxy group" and the like can be mentioned.

Unless otherwise specified, as the "$C_{1-6}$ alkoxy group" in the present specification, for example, methoxy, ethoxy, propoxy, isopropoxy, butoxy, isobutoxy, tert-butoxy, pentyloxy, hexyloxy and the like can be mentioned. As the "$C_{1-10}$ alkoxy group" in the present specification, heptyloxy, octyloxy, nonyloxy, decyloxy and the like can be mentioned besides the above-mentioned $C_{1-6}$ alkoxy group.

As the "heterocyclyloxy group" in the present specification, hydroxy group substituted by a "heterocyclic group" below can be mentioned. As preferable examples of the heterocyclyloxy group, tetrahydropyranyloxy, thiazolyloxy, pyridyloxy, pyrazolyloxy, oxazolyloxy, thienyloxy, furyloxy, tetrahydrothiopyranyloxy, 1-oxidotetrahydrothiopyranyloxy, 1,1-dioxidotetrahydrothiopyranyloxy and the like can be mentioned.

Unless otherwise specified, as the "$C_{6-14}$ aryloxy group" in the present specification, for example, phenoxy, 1-naphthyloxy, 2-naphthyloxy and the like can be mentioned.

Unless otherwise specified, as the "$C_{7-16}$ aralkyloxy group" in the present specification, for example, benzyloxy, phenethyloxy and the like can be mentioned.

Unless otherwise specified, as the "tri-$C_{1-6}$ alkyl-silyloxy group" in the present specification, for example, trimethylsilyloxy, tert-butyl(dimethyl)silyloxy and the like can be mentioned.

As the "$C_{1-6}$ alkylsulfonyloxy group" in the present specification, for example, methylsulfonyloxy, ethylsulfonyloxy and the like can be mentioned.

As the "heterocyclylsulfonyloxy group" in the present specification, sulfonyloxy group substituted by a "heterocyclic group" below can be mentioned. As preferable examples of the heterocyclylsulfonyloxy group, thienylsulfonyloxy, furylsulfonyloxy and the like can be mentioned.

Unless otherwise specified, as the "optionally substituted mercapto group" in the present specification, for example, "mercapto group", "optionally substituted $C_{1-10}$ alkylthio group", "optionally substituted heterocyclylthio group", "optionally substituted $C_{6-14}$ arylthio group", "optionally substituted $C_{7-16}$ aralkylthio group" and the like can be mentioned.

Unless otherwise specified, as the "$C_{1-6}$ alkylthio group" in the present specification, for example, methylthio, ethylthio, propylthio, isopropylthio, butylthio, sec-butylthio, tert-butylthio and the like can be mentioned. As the "$C_{1-10}$ alkylthio group" in the present specification, heptylthio, octylthio, nonylthio, decylthio and the like can be mentioned besides the above-mentioned $C_{1-6}$ alkylthio group.

Unless otherwise specified, as the "heterocyclylthio group" in the present specification, mercapto group substituted by a "heterocyclic group" below can be mentioned. As preferable examples of the heterocyclylthio group, tetrahydropyranylthio, thiazolylthio, pyridylthio, pyrazolylthio, oxazolylthio, thienylthio, furylthio, tetrahydrothiopyranylthio, 1-oxidotetrahydrothiopyranylthio, 1,1-dioxidotetrahydrothiopyranylthio and the like can be mentioned.

Unless otherwise specified, as the "$C_{6-14}$ arylthio group" in the present specification, for example, phenylthio, 1-naphthylthio, 2-naphthylthio and the like can be mentioned.

Unless otherwise specified, as the "$C_{7-16}$ aralkylthio group" in the present specification, for example, benzylthio, phenethylthio and the like can be mentioned.

Unless otherwise specified, as the "heterocyclic group" in the present specification, for example, a 4- to 14-membered (monocyclic, bicyclic or tricyclic) heterocyclic group containing one or two kind(s) of 1 to 4 heteroatom(s) selected from a nitrogen atom, a sulfur atom and an oxygen atom as a ring-constituting atom, besides carbon atoms, preferably (i) 5- to 14-membered (preferably 5- to 10-membered) aromatic heterocyclic group, (ii) 4- to 10-membered non-aromatic heterocyclic group and the like can be mentioned. Of these, 5- or 6-membered aromatic heterocyclic group is preferable.

Specifically, aromatic heterocyclic group such as thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl, 5-oxazolyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl, 4-isothiazolyl, 5-isothiazolyl), isoxazolyl (e.g., 3-isoxazolyl, 4-isoxazolyl, 5-isoxazolyl), indolyl (e.g., 1-indolyl, 2-indolyl, 3-indolyl), 2-benzothiazolyl, 2-benzoxazolyl, benzimidazolyl (e.g., 1-benzimidazolyl, 2-benzimidazolyl), benzo[b]thienyl (e.g., 2-benzo[b]thienyl, 3-benzo[b]thienyl), benzo[b]furanyl (e.g., 2-benzo[b]furanyl, 3-benzo[b]furanyl) and the like; non-aromatic heterocyclic group such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholinyl (e.g., 2-morpholinyl, 3-morpholinyl, 4-morpholinyl), thiomorpholinyl (e.g., 2-thiomorpholinyl, 3-thiomorpholinyl, 4-thiomorpholinyl), tetrahydropyranyl, tetrahydrothiopyranyl, 1-oxidotetrahydrothiopyranyl, 1,1-dioxidotetrahydrothiopyranyl, oxopyrrolidinyl, oxetanyl (e.g., 2-oxetanyl, 3-oxetanyl) and the like, and the like can be mentioned.

Unless otherwise specified, as the "$C_{1-6}$ alkylsulfonyl group" in the present specification, for example, methylsulfonyl, ethylsulfonyl and the like can be mentioned.

Unless otherwise specified, as the "$C_{1-6}$ alkylsulfinyl group" in the present specification, for example, methylsulfinyl, ethylsulfinyl and the like can be mentioned.

Unless otherwise specified, as the "$C_{6-14}$ arylsulfonyl group" in the present specification, for example, phenylsulfonyl, 1-naphthylsulfonyl, 2-naphthylsulfonyl and the like can be mentioned.

Unless otherwise specified, as the "$C_{6-14}$ arylsulfinyl group" in the present specification, for example, phenylsulfinyl, 1-naphthylsulfinyl, 2-naphthylsulfinyl and the like can be mentioned.

Unless otherwise specified, as the "optionally esterified carboxyl group" in the present specification, for example, carboxyl group, $C_{1-6}$ alkoxy-carbonyl group (e.g., methoxycarbonyl, ethoxycarbonyl, propoxycarbonyl, tert-butoxycarbonyl etc.), $C_{6-14}$ aryloxy-carbonyl group (e.g., phenoxycarbonyl etc.), $C_{7-16}$ aralkyloxy-carbonyl group (e.g., benzyloxycarbonyl, phenethyloxycarbonyl etc.) and the like can be mentioned.

Unless otherwise specified, as the "optionally halogenated $C_{1-6}$ alkyl group" in the present specification, the above-mentioned "$C_{1-6}$ alkyl group" optionally substituted by 1 to 5 above-mentioned "halogen atoms" can be mentioned. For example, methyl, ethyl, propyl, isopropyl, butyl, tert-butyl, isobutyl, trifluoromethyl and the like can be mentioned.

Unless otherwise specified, as the "optionally halogenated $C_{1-6}$ alkoxy group" in the present specification, the above-mentioned "$C_{1-6}$ alkoxy group" optionally substituted by 1 to 5 above-mentioned "halogen atoms" can be mentioned. For example, methoxy, ethoxy, isopropoxy, tert-butoxy, trifluoromethoxy and the like can be mentioned.

Unless otherwise specified, as the "mono- or di-$C_{1-6}$ alkyl-amino group" in the present specification, amino group mono- or di-substituted by the above-mentioned "$C_{1-6}$ alkyl group" can be mentioned. For example, methylamino, ethylamino, propylamino, dimethylamino, diethylamino and the like can be mentioned.

Unless otherwise specified, as the "mono- or di-$C_{6-14}$ aryl-amino group" in the present specification, amino group mono- or di-substituted by the above-mentioned "$C_{6-14}$ aryl group" can be mentioned. For example, phenylamino, diphenylamino, 1-naphthylamino, 2-naphthylamino and the like can be mentioned.

Unless otherwise specified, as the "mono- or di-$C_{7-16}$ aralkyl-amino group" in the present specification, amino group mono- or di-substituted by the above-mentioned "$C_{7-16}$ aralkyl group" can be mentioned. For example, benzylamino, phenethylamino and the like can be mentioned.

Unless otherwise specified, as the "N—$C_{1-6}$ alkyl-N—$C_{6-14}$ aryl-amino group" in the present specification, amino group substituted by the above-mentioned "$C_{1-6}$ alkyl group" and the above-mentioned "$C_{6-14}$ aryl group" can be mentioned. For example, N-methyl-N-phenylamino, N-ethyl-N-phenylamino and the like can be mentioned.

Unless otherwise specified, as the "N—$C_{1-6}$ alkyl-N—$C_{7-16}$ aralkyl-amino group" in the present specification, amino group substituted by the above-mentioned "$C_{1-6}$ alkyl group" and the above-mentioned "$C_{7-16}$ aralkyl group" can be mentioned. For example, N-methyl-N-benzylamino, N-ethyl-N-benzylamino and the like can be mentioned.

Unless otherwise specified, as the "mono- or di-$C_{1-6}$ alkyl-carbamoyl group" in the present specification, carbamoyl group mono- or di-substituted by the above-mentioned "$C_{1-6}$ alkyl group" can be mentioned. For example, methylcarbamoyl, ethylcarbamoyl, dimethylcarbamoyl, diethylcarbamoyl, ethylmethylcarbamoyl and the like can be mentioned.

Unless otherwise specified, as the "N—$C_{1-6}$ alkyl-N—$C_{1-6}$ alkyl-carbonyl-amino group" in the present specification, amino group substituted by the above-mentioned "$C_{1-6}$ alkyl group" and $C_{1-6}$ alkyl-carbonyl group (e.g., acetyl, isobutanoyl, isopentanoyl) can be mentioned. For example, N-methyl-N-acetylamino, N-ethyl-N-acetylamino and the like can be mentioned.

Unless otherwise specified, as the "mono- or di-$C_{6-14}$ aryl-carbamoyl group" in the present specification, carbamoyl group mono- or di-substituted by the above-mentioned "$C_{6-14}$ aryl group" can be mentioned. For example, phenylcarbamoyl, 1-naphthylcarbamoyl, 2-naphthylcarbamoyl and the like can be mentioned.

Unless otherwise specified, as the "mono- or di-5- to 7-membered heterocyclyl-carbamoyl group" in the present specification, carbamoyl group mono- or di-substituted by 5- to 7-membered heterocyclic group can be mentioned. As the 5- to 7-membered heterocyclic group, a heterocyclic group containing one or two kind(s) of 1 to 4 heteroatom(s) selected from a nitrogen atom, a sulfur atom and an oxygen atom as a ring-constituting atom, besides carbon atoms can be mentioned. As preferable examples of the "mono- or di-5 to 7-membered heterocyclyl-carbamoyl group", 2-pyridylcarbamoyl, 3-pyridylcarbamoyl, 4-pyridylcarbamoyl, 2-thienylcarbamoyl, 3-thienylcarbamoyl and the like can be mentioned.

Unless otherwise specified, as the "mono- or di-$C_{1-6}$ alkyl-sulfamoyl group" in the present specification, sulfamoyl group mono- or di-substituted by the above-mentioned "$C_{1-6}$ alkyl group" can be used, for example, methylsulfamoyl, ethylsulfamoyl, dimethylsulfamoyl, diethylsulfamoyl and the like can be mentioned.

Unless otherwise specified, as the "mono- or di-$C_{6-14}$ aryl-sulfamoyl group" in the present specification, sulfamoyl group mono- or di-substituted by the above-mentioned "$C_{6-14}$ aryl group" can be used, for example, phenylsulfamoyl, diphenylsulfamoyl, 1-naphthylsulfamoyl, 2-naphthylsulfamoyl and the like can be mentioned.

As the "mono- or di-$C_{1-6}$ alkyl-phosphono group" in the present specification, phosphono group mono- or di-substituted by the above-mentioned "$C_{1-6}$ alkyl group" can be mentioned. For example, dimethylphosphono, diethylphosphono, diisopropylphosphono, dibutylphosphono and the like can be mentioned.

Unless otherwise specified, as the "optionally substituted $C_{1-6}$ alkyl group", "optionally substituted $C_{2-6}$ alkenyl group", "optionally substituted $C_{2-6}$ alkynyl group", "optionally substituted $C_{1-10}$ alkoxy group (containing optionally substituted $C_{1-6}$ alkoxy group)", "optionally substituted $C_{1-6}$ alkylsulfonyloxy group" and "optionally substituted $C_{1-10}$ alkylthio group (containing optionally substituted $C_{1-6}$ alkylthio group)" in the present specification, for example, "$C_{1-6}$ alkyl group", "$C_{2-6}$ alkenyl group", "$C_{2-6}$ alkynyl group", "$C_{1-10}$ alkoxy group (containing $C_{1-6}$ alkoxy group)", "$C_{1-6}$ alkylsulfonyloxy group" and "$C_{1-10}$ alkylthio group (containing $C_{1-6}$ alkylthio group)", each of which optionally has 1 to 5 substituent(s) at substitutable position(s) selected from (1) halogen atom;
(2) hydroxy group;
(3) amino group;
(4) nitro group;
(5) cyano group;
(6) heterocyclic group (preferably furyl, pyridyl, thienyl, pyrazolyl, thiazolyl, oxazolyl, pyrrolidinyl, oxopyrrolidinyl, tetrahydropyranyl, tetrahydrothiopyranyl, 1-oxidotetrahydrothiopyranyl, 1,1-dioxidotetrahydrothiopyranyl, oxetanyl) optionally substituted by 1 to 3 substituent(s) selected from halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group;
(7) mono- or di-$C_{1-6}$ alkyl-amino group;
(8) mono- or di-$C_{6-14}$ aryl-amino group;
(9) mono- or di-$C_{7-16}$ aralkyl-amino group;
(10) N—$C_{1-6}$ alkyl-N—$C_{6-14}$ aryl-amino group;
(11) N—$C_{1-6}$ alkyl-N—$C_{7-16}$ aralkyl-amino group;
(12) $C_{3-8}$ cycloalkyl group;
(13) optionally halogenated $C_{1-6}$ alkoxy group;
(14) $C_{1-6}$ alkylthio group;
(15) $C_{1-6}$ alkylsulfinyl group;
(16) $C_{1-6}$ alkylsulfonyl group;
(17) optionally esterified carboxyl group;
(18) carbamoyl group;
(19) thiocarbamoyl group;
(20) mono- or di-$C_{1-6}$ alkyl-carbamoyl group;
(21) mono- or di-$C_{6-14}$ aryl-carbamoyl group;
(22) mono- or di-5- to 7-membered heterocyclyl-carbamoyl group;
(23) $C_{1-6}$ alkyl-carbonylamino group (e.g., acetylamino, propionylamino) optionally substituted by carboxyl group;
(24) $C_{6-14}$ aryloxy group optionally substituted by 1 to 3 substituent(s) selected from halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group;
(25) $C_{6-14}$ aryl group optionally substituted by 1 to 3 substituent(s) selected from halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group;

(26) heterocyclyloxy group optionally substituted by 1 to 3 substituent(s) selected from halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group;

(27) sulfamoyl group;

(28) mono- or di-$C_{1-6}$ alkyl-sulfamoyl group;

(29) mono- or di-$C_{6-14}$ aryl-sulfamoyl group;

(30) $C_{7-16}$ aralkyloxy group optionally substituted by 1 to 3 substituent(s) selected from halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group;

(31) N—$C_{1-6}$ alkyl-N—$C_{1-6}$ alkyl-carbonyl-amino group;

(32) mono- or di-$C_{1-6}$ alkyl-phosphono group; and the like, can be mentioned.

As the "optionally substituted $C_{3-8}$ cycloalkyl group", "optionally substituted $C_{6-14}$ aryl group", "optionally substituted $C_{7-16}$ aralkyl group", "optionally substituted heterocyclic group", "optionally substituted heterocyclyloxy group", "optionally substituted $C_{6-14}$ aryloxy group", "optionally substituted $C_{7-16}$ aralkyloxy group", "optionally substituted heterocyclylsulfonyloxy group", "optionally substituted heterocyclylthio group", "optionally substituted $C_{6-14}$ arylthio group" and "optionally substituted $C_{7-16}$ aralkylthio group" in the present specification, for example, "$C_{3-8}$ cycloalkyl group", "$C_{6-14}$ aryl group", "$C_{7-16}$ aralkyl group", "heterocyclic group", "heterocyclyloxy group", "$C_{6-14}$ aryloxy group", "$C_{7-16}$ aralkyloxy group", "heterocyclylsulfonyloxy group", "heterocyclylthio group", "$C_{6-14}$ arylthio group" and "$C_{7-16}$ aralkylthio group", each of which optionally has 1 to 5 substituent(s) at substitutable position(s) selected from (1) halogen atom;
(2) hydroxy group;
(3) amino group;
(4) nitro group;
(5) cyano group;
(6) optionally substituted $C_{1-6}$ alkyl group;
(7) optionally substituted $C_{2-6}$ alkenyl group;
(8) optionally substituted $C_{2-6}$ alkynyl group;
(9) $C_{6-14}$ aryl group optionally substituted by 1 to 3 substituent(s) selected from halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group;

(10) $C_{6-14}$ aryloxy group optionally substituted by 1 to 3 substituent(s) selected from halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group;

(11) $C_{7-16}$ aralkyloxy group optionally substituted by 1 to 3 substituent(s) selected from halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group;

(12) heterocyclic group (preferably furyl, pyridyl, thienyl, pyrazolyl, thiazolyl, oxazolyl, pyrrolidinyl, oxopyrrolidinyl, tetrahydropyranyl, tetrahydrothiopyranyl, 1-oxidotetrahydrothiopyranyl, 1,1-dioxidotetrahydrothiopyranyl, oxetanyl) optionally substituted by 1 to 3 substituent(s) selected from halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group;

(13) mono- or di-$C_{1-6}$ alkyl-amino group;
(14) mono- or di-$C_{6-14}$ aryl-amino group;
(15) mono- or di-$C_{7-16}$ aralkyl-amino group;
(16) N—$C_{1-6}$ alkyl-N—$C_{6-14}$ aryl-amino group;
(17) N—$C_{1-6}$ alkyl-N—$C_{7-16}$ aralkyl-amino group;
(18) $C_{3-8}$ cycloalkyl group;
(19) optionally substituted $C_{1-6}$ alkoxy group;
(20) $C_{1-6}$ alkylthio group;
(21) $C_{1-6}$ alkylsulfinyl group;
(22) $C_{1-6}$ alkylsulfonyl group;
(23) optionally esterified carboxyl group;
(24) carbamoyl group;
(25) thiocarbamoyl group;
(26) mono- or di-$C_{1-6}$ alkyl-carbamoyl group;
(27) mono- or di-$C_{6-14}$ aryl-carbamoyl group;
(28) mono- or di-5- to 7-membered heterocyclyl-carbamoyl group;
(29) sulfamoyl group;
(30) mono- or di-$C_{1-6}$ alkyl-sulfamoyl group;
(31) mono- or di-$C_{6-14}$ aryl-sulfamoyl group;
(32) N—$C_{1-6}$ alkyl-N—$C_{1-6}$ alkyl-carbonyl-amino group;
(33) heterocyclyloxy group optionally substituted by 1 to 3 substituent(s) selected from halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group;

(34) mono- or di-$C_{1-6}$ alkyl-phosphono group; and the like, can be mentioned.

Unless otherwise specified, as the "optionally substituted amino group" in the present specification, amino group optionally substituted by 1 or 2 substituent(s) selected from (1) optionally substituted $C_{1-6}$ alkyl group;
(2) optionally substituted $C_{2-6}$ alkenyl group;
(3) optionally substituted $C_{2-6}$ alkynyl group;
(4) optionally substituted $C_{3-8}$ cycloalkyl group;
(5) optionally substituted $C_{6-14}$ aryl group;
(6) optionally substituted $C_{1-6}$ alkoxy group;
(7) optionally substituted acyl group;
(8) optionally substituted heterocyclic group (preferably furyl, pyridyl, thienyl, pyrazolyl, thiazolyl, oxazolyl);
(9) sulfamoyl group;
(10) mono- or di-$C_{1-6}$ alkyl-sulfamoyl group;
(11) mono- or di-$C_{6-14}$ aryl-sulfamoyl group; and the like, can be mentioned. When the "optionally substituted amino group" is an amino group substituted by 2 substituents, these substituents may form a nitrogen-containing heterocycle together with the adjacent nitrogen atom. As the "nitrogen-containing heterocycle", for example, a 5- to 7-membered nitrogen-containing heterocycle containing at least one nitrogen atom and optionally further containing 1 or 2 heteroatom(s) selected from an oxygen atom, a sulfur atom and a nitrogen atom as a ring-constituting atom, besides carbon atoms can be mentioned. As preferable examples of the nitrogen-containing heterocycle, pyrrolidine, imidazolidine, pyrazolidine, piperidine, piperazine, morpholine, thiomorpholine, thiazolidine, oxazolidine and the like can be mentioned.

Unless otherwise specified, as the "optionally substituted acyl group" in the present specification, groups represented by the formula: —$COR^8$, —CO—$OR^8$, —$SO_2R^8$, —$SOR^8$, —$PO(OR^8)(OR^9)$, —CO—$NR^{8a}R^{9a}$ and —CS—$NR^{8a}R^{9a}$, wherein $R^8$ and $R^9$ are the same or different and each is a hydrogen atom, an optionally substituted hydrocarbon group or an optionally substituted heterocyclic group, and $R^{8a}$ and $R^{9a}$ are the same or different and each is a hydrogen atom, an optionally substituted hydrocarbon group or an optionally substituted heterocyclic group, or $R^{8a}$ and $R^{9a}$ may form an optionally substituted nitrogen-containing heterocycle together with the adjacent nitrogen atom, and the like can be mentioned.

As the "nitrogen-containing heterocycle" of the "optionally substituted nitrogen-containing heterocycle" which $R^{8a}$ and $R^{9a}$ form together with the adjacent nitrogen atom, for example, a 5- to 7-membered nitrogen-containing heterocycle containing at least one nitrogen atom and optionally further containing 1 to 2 heteroatom(s) selected from an oxygen atom, a sulfur atom and a nitrogen atom as a ring-constituting atom, besides carbon atoms can be mentioned. As preferable examples of the "nitrogen-containing heterocycle", pyrrolidine, imidazolidine, pyrazolidine, piperidine, piperazine, morpholine, thiomorpholine, thiazolidine, oxazolidine and the like can be mentioned.

The nitrogen-containing heterocycle optionally has 1 to 2 substituent(s) at substitutable position(s). As these substituent(s), a hydroxy group, an optionally halogenated $C_{1-6}$ alkyl group, a $C_{6-14}$ aryl group, a $C_{7-16}$ aralkyl group and the like can be mentioned.

As preferable examples of "optionally substituted acyl group", formyl group, carboxyl group, carbamoyl group, $C_{1-6}$ alkyl-carbonyl group (e.g., acetyl, isobutanoyl, isopentanoyl), $C_{1-6}$ alkoxy-carbonyl group (e.g., methoxycarbonyl, ethoxycarbonyl, propoxycarbonyl, tert-butoxycarbonyl), $C_{3-8}$ cycloalkyl-carbonyl group (e.g., cyclopentylcarbonyl, cyclohexylcarbonyl), $C_{6-14}$ aryl-carbonyl group (e.g., benzoyl, 1-naphthoyl, 2-naphthoyl), $C_{7-16}$ aralkyl-carbonyl group (e.g., phenylacetyl, 2-phenylpropanoyl), $C_{6-14}$ aryloxy-carbonyl group (e.g., phenyloxycarbonyl, naphthyloxycarbonyl), $C_{7-16}$ aralkyloxy-carbonyl group (e.g., benzyloxycarbonyl, phenethyloxycarbonyl), mono- or di-$C_{1-6}$ alkylcarbamoyl group, mono- or di-$C_{6-14}$ aryl-carbamoyl group, $C_{3-8}$ cycloalkyl-carbamoyl group (e.g., cyclopropylcarbamoyl), $C_{7-16}$ aralkyl-carbamoyl group (e.g., benzylcarbamoyl), $C_{1-6}$ alkylsulfonyl group, $C_{6-14}$ arylsulfonyl group, nitrogen-containing heterocyclyl-carbonyl group (e.g., pyrrolidinylcarbonyl, piperidinylcarbonyl), $C_{1-6}$ alkylsulfinyl group, $C_{6-14}$ arylsulfinyl group, thiocarbamoyl group, mono- or di-$C_{1-6}$ alkyl-phosphono group (e.g., dimethylphosphono, diethylphosphono, diisopropylphosphono, dibutylphosphono) and the like can be mentioned.

The "$C_{1-4}$ alkylene group" of the "Optionally substituted $C_{1-4}$ alkylene group" in the present specification is straight-chain or branched, and, for example, methylene, ethylene, 1-methylethylene, propylene, 1-ethylethylene, 1-methylpropylene, 2-methylpropylene, butylene and the like can be mentioned. The $C_{1-4}$ alkylene group optionally has 1 to 3 substituent(s) at substitutable position(s). As these substituent(s), for example, halogen atom, hydroxy group, amino group, mono- or di-$C_{1-16}$ alkyl-amino group, mono- or di-$C_{6-14}$ aryl-amino group, mono- or di-$C_{7-16}$ aralkyl-amino group, nitro group, cyano group, $C_{1-6}$ alkoxy group, $C_{1-6}$ alkylthio group and the like can be mentioned.

As the "$C_{1-3}$ alkylene group" of the "optionally substituted $C_{1-3}$ alkylene group" in the present specification, of the aforementioned "$C_{1-4}$ alkylene groups", those having 1 to 3 carbon atom(s) can be mentioned. The $C_{1-3}$ alkylene group optionally has 1 to 3 substituent(s) at substitutable position(s). As these substituent(s), those exemplarily shown as the substituent of the above-mentioned $C_{1-4}$ alkylene group can be mentioned.

The compound represented by the formula (I) of the present invention (hereinafter sometimes to be abbreviated as compound (I)) and a salt thereof are explained in the following.

$R^2$ in the formula (I) is a halogen atom, a nitro group, an optionally substituted hydrocarbon group, an optionally substituted hydroxy group, an optionally substituted amino group, an optionally substituted mercapto group, an optionally substituted acyl group or an optionally substituted heterocyclic group, preferably a halogen atom, an optionally substituted hydrocarbon group, an optionally substituted hydroxy group, an optionally substituted amino group, an optionally substituted mercapto group or an optionally substituted heterocyclic group, more preferably an optionally substituted hydrocarbon group or an optionally substituted hydroxy group. Of these, an optionally substituted hydroxy group is preferable. As preferable specific examples of the optionally substituted hydroxy group, (1) hydroxy group,
(2) $C_{1-10}$ alkoxy group optionally substituted by 1 to 3 substituent(s) selected from
  (a) a 4- to 7-membered heterocyclic group containing one or two kind(s) of 1 to 4 heteroatom(s) selected from a nitrogen atom, a sulfur atom and an oxygen atom as a ring-constituting atom, besides carbon atoms (preferably, pyridyl, thiazolyl, pyrrolidinyl, oxopyrrolidinyl, tetrahydropyranyl, tetrahydrothiopyranyl, 1-oxidotetrahydrothiopyranyl, 1,1-dioxidotetrahydrothiopyranyl, oxetanyl), optionally substituted by 1 to 3 substituent(s) selected from optionally halogenated $C_{1-6}$ alkyl group, hydroxy group and $C_{1-6}$ alkoxy-carbonyl group,
  (b) $C_{3-8}$ cycloalkyl group,
  (c) hydroxy group,
  (d) optionally halogenated $C_{1-6}$ alkoxy group,
  (e) amino group,
  (f) mono- or di-$C_{1-6}$ alkyl-amino group,
  (g) N—$C_{1-6}$ alkyl-N—$C_{1-6}$ alkyl-carbonyl-amino group,
  (h) $C_{7-16}$ aralkyloxy group,
  (i) $C_{1-6}$ alkylthio group,
  (j) $C_{1-6}$ alkylsulfinyl group,
  (k) $C_{1-6}$ alkylsulfonyl group, and
  (l) mono- or di-$C_{1-6}$ alkyl-phosphono group,
(3) heterocyclyloxy group (preferably tetrahydropyranyloxy, pyridyloxy, tetrahydrothiopyranyloxy, 1-oxidotetrahydrothiopyranyloxy, 1,1-dioxidotetrahydrothiopyranyloxy) optionally substituted by optionally halogenated $C_{1-6}$ alkyl group,
(4) $C_{7-16}$ aralkyloxy group,
(5) silyloxy group optionally substituted by 1 to 3 $C_{1-6}$ alkyl group(s),
(6) $C_{1-6}$ alkylsulfonyloxy group, and
(7) heterocyclylsulfonyloxy group (preferably thienylsulfonyloxy, furylsulfonyloxy), can be mentioned.

$R^1$ and $R^3$ in the formula (I) are the same (except when $R^1$ and $R^3$ are both hydrogen atoms) or different and each is a hydrogen atom, a halogen atom, an optionally substituted hydrocarbon group or an optionally substituted hydroxy group, preferably a hydrogen atom, a halogen atom or a $C_{1-6}$ alkyl group, more preferably a halogen atom or a $C_{1-6}$ alkyl group. Of these, a $C_{1-6}$ alkyl group (preferably methyl) is preferable.

$R^4$ and $R^5$ in the formula (I) are the same or different and each is a hydrogen atom, a halogen atom, an optionally substituted hydrocarbon group or an optionally substituted hydroxy group, preferably a hydrogen atom or a halogen atom (preferably fluorine atom).

$R^{10}$ and $R^{11}$ in the formula (I) are the same or different and each is a hydrogen atom, a halogen atom or a $C_{1-6}$ alkoxy group, preferably both are hydrogen atoms.

E in the formula (I) is a bond, an optionally substituted $C_{1-4}$ alkylene group, —$W^1$—O—$W^2$—, —$W^1$—S—$W^2$— or —$W^1$—N($R^6$)—$W^2$— ($W^1$ and $W^2$ are the same or different and each is a bond or an optionally substituted $C_{1-3}$ alkylene group, and $R^6$ is a hydrogen atom, an optionally substituted acyl group or an optionally substituted hydrocarbon group), preferably a bond.

Ring $S^1$ in the formula (I) is a benzene ring optionally further having substituent(s) selected from a halogen atom, an optionally substituted hydrocarbon group, an optionally substituted hydroxy group and an optionally substituted amino group, preferably a benzene ring optionally further having a $C_{1-6}$ alkoxy group. The number of the substituent is, for example, 1 or 2.

R in the formula (I) is an optionally substituted hydroxy group or an optionally substituted amino group, preferably an optionally substituted hydroxy group, more preferably a hydroxy group or a $C_{1-6}$ alkoxy group. Of these, a hydroxy group is preferable.

As the "preferable examples of compound (I)", the following compounds can be mentioned.

[Compound A]

A compound wherein $R^2$ is
(1) halogen atom,
(2) $C_{1-6}$ alkyl group optionally substituted by $C_{6-14}$ aryloxy group optionally substituted by halogen atom,
(3) hydroxy group,
(4) $C_{1-10}$ alkoxy group optionally substituted by 1 to 3 substituent(s) selected from
  (a) 5- to 7-membered heterocyclic group containing one or two kind(s) of 1 to 4 heteroatom(s) selected from a nitrogen atom, a sulfur atom and an oxygen atom as a ring-constituting atom, besides carbon atom (preferably, pyridyl, thiazolyl), optionally substituted by optionally halogenated $C_{1-6}$ alkyl group,
  (b) $C_{3-8}$ cycloalkyl group,
  (c) hydroxy group,
  (d) optionally halogenated $C_{1-6}$ alkoxy group,
  (e) amino group, and
  (f) mono- or di-$C_{1-6}$ alkyl-amino group,
(5) heterocyclyloxy group (preferably tetrahydropyranyloxy), or
(6) $C_{7-16}$ aralkyloxy group;

$R^1$ and $R^3$ are the same (except when $R^1$ and $R^3$ are both hydrogen atoms) or different and each is hydrogen atom, halogen atom or $C_{1-6}$ alkyl group;

$R^4$ and $R^5$ are the same or different and each is hydrogen atom or halogen atom;

$R^{10}$ and $R^{11}$ are both hydrogen atoms;

E is bond;

ring $S^1$ is benzene ring optionally further having $C_{1-6}$ alkoxy group; and R is hydroxy group or $C_{1-6}$ alkoxy group (preferably hydroxy group).

[Compound B]

A compound wherein $R^2$ is
(1) halogen atom,
(2) $C_{1-6}$ alkyl group optionally substituted by $C_{6-14}$ aryloxy group optionally substituted by halogen atom,
(3) hydroxy group,
(4) $C_{1-10}$ alkoxy group optionally substituted by 1 to 3 substituent(s) selected from
  (a) 5- to 7-membered heterocyclic group containing one or two kind(s) of 1 to 4 heteroatom(s) selected from a nitrogen atom, a sulfur atom and an oxygen atom as a ring-constituting atom, besides carbon atom (preferably, pyridyl, thiazolyl, pyrrolidinyl, oxopyrrolidinyl, tetrahydrothiopyranyl, 1,1-dioxidotetrahydrothiopyranyl), optionally substituted by 1 to 3 substituent(s) selected from optionally halogenated $C_{1-6}$ alkyl group, hydroxy group and $C_{1-6}$ alkoxy-carbonyl group,
  (b) $C_{3-8}$ cycloalkyl group,
  (c) hydroxy group, (d) optionally halogenated $C_{1-6}$ alkoxy group,
(e) amino group
(f) mono- or di-$C_{1-6}$ alkyl-amino group,
(g) N—$C_{1-6}$ alkyl-N—$C_{1-6}$ alkyl-carbonyl-amino group,
(h) $C_{7-16}$ aralkyloxy group,
(i) $C_{1-6}$ alkylthio group, and
(j) $C_{1-6}$ alkylsulfonyl group,
(5) heterocyclyloxy group (preferably tetrahydropyranyloxy, pyridyloxy, tetrahydrothiopyranyloxy, 1,1-dioxidotetrahydrothiopyranyloxy), optionally substituted by an optionally halogenated $C_{1-6}$ alkyl group,
(6) $C_{7-16}$ aralkyloxy group,
(7) silyloxy group optionally substituted by 1 to 3 $C_{1-6}$ alkyl group(s),
(8) $C_{1-6}$ alkylsulfonyloxy group, or
(9) heterocyclylsulfonyloxy group (preferably thienylsulfonyloxy, furylsulfonyloxy);

$R^1, R^3, R^4, R^5, R^{10}, R^{11}, E,$ ring $S^1$ and R are as defined for the aforementioned [Compound A].

[Compound C]
A compound wherein
$R^2$ is
(1) halogen atom,
(2) $C_{1-6}$ alkyl group optionally substituted by $C_{6-14}$ aryloxy group optionally substituted by halogen atom,
(3) hydroxy group,
(4) $C_{1-10}$ alkoxy group optionally substituted by 1 to 3 substituent(s) selected from
  (a) 4- to 7-membered heterocyclic group containing one or two kind(s) of 1 to 4 heteroatom(s) selected from a nitrogen atom, a sulfur atom and an oxygen atom as a ring-constituting atom, besides carbon atom (preferably, pyridyl, thiazolyl, pyrrolidinyl, oxopyrrolidinyl, tetrahydropyranyl, tetrahydrothiopyranyl, 1-oxidotetrahydrothiopyranyl, 1,1-dioxidotetrahydrothiopyranyl, oxetanyl), optionally substituted by 1 to 3 substituent(s) selected from optionally halogenated $C_{1-6}$ alkyl group, hydroxy group and $C_{1-6}$ alkoxy-carbonyl group,
  (b) $C_{3-8}$ cycloalkyl group,
  (c) hydroxy group,
  (d) optionally halogenated $C_{1-6}$ alkoxy group,
  (e) amino group
  (f) mono- or di-$C_{1-6}$ alkyl-amino group,
  (g) N—$C_{1-6}$ alkyl-N—$C_{1-6}$ alkyl-carbonyl-amino group,
  (h) $C_{7-16}$ aralkyloxy group,
  (i) $C_{1-6}$ alkylthio group,
  (j) $C_{1-6}$ alkylsulfinyl group,
  (k) $C_{1-6}$ alkylsulfonyl group, and
  (l) mono- or di-$C_{1-6}$ alkyl-phosphono group,
(5) heterocyclyloxy group (preferably tetrahydropyranyloxy, pyridyloxy, tetrahydrothiopyranyloxy, 1-oxidotetrahydrothiopyranyloxy, 1,1-dioxidotetrahydrothiopyranyloxy), optionally substituted by optionally halogenated $C_{1-6}$ alkyl group,
(6) $C_{7-16}$ aralkyloxy group,
(7) silyloxy group optionally substituted by 1 to 3 $C_{1-6}$ alkyl group(s),
(8) $C_{1-6}$ alkylsulfonyloxy group, or
(9) heterocyclylsulfonyloxy group (preferably thienylsulfonyloxy, furylsulfonyloxy);

$R^1, R^3, R^4, R^5, R^{10}, R^{11}, E,$ ring $S^1$ and R are as defined for the aforementioned [Compound A]. In the present compound, $R^1$ and $R^3$ are preferably the same or different and each is a $C_{1-6}$ alkyl group.

[Compound D]
3-[4-[[4'-(benzyloxy)-2',6'-dimethylbiphenyl-3-yl]methoxy]phenyl]propanoic acid (Example 39);
3-(4-{[4'-(2-ethoxyethoxy)-2',6'-dimethylbiphenyl-3-yl]methoxy}phenyl)-2,2-difluoropropanoic acid (Example 75);
3-[4-({4'-[2-(ethylsulfonyl)ethoxy]-2',6'-dimethylbiphenyl-3-yl}methoxy)-2-fluorophenyl]propanoic acid (Example 86);
3-[4-({2',6'-dimethyl-4'-[3-(2-oxopyrrolidin-1-yl)propoxy]biphenyl-3-yl}methoxy)-2-fluorophenyl]propanoic acid (Example 90);
3-[4-({2',6'-dimethyl-4'-[(6-methylpyridin-2-yl)methoxy]biphenyl-3-yl}methoxy)-2-fluorophenyl]propanoic acid (Example 97);
3-[2-fluoro-4-({4'-[(4-hydroxy-1,1-dioxidotetrahydro-2H-thiopyran-4-yl)methoxy]-2',6'-dimethylbiphenyl-3-yl}methoxy)phenyl]propanoic acid (Example 100);
3-[4-({2',6'-dimethyl-4'-[(methylsulfonyl)oxy]biphenyl-3-yl}methoxy)-2-fluorophenyl]propanoic acid (Example 102);
3-[4-({4'-[(1,1-dioxidotetrahydro-2H-thiopyran-4-yl)oxy]-2',6'-dimethylbiphenyl-3-yl}methoxy)-2-fluorophenyl]propanoic acid (Example 114);
3-[4-({2',6'-dimethyl-4'-[(3-methyloxetan-3-yl)methoxy]biphenyl-3-yl}methoxy)-2-fluorophenyl]propanoic acid (Example 116);
3-(4-{[2',6'-dimethyl-4'-(tetrahydro-2H-pyran-4-yloxy)biphenyl-3-yl]methoxy}-2-fluorophenyl)propanoic acid (Example 118);
3-[4-({4'-[3-(diethoxyphosphoryl)propoxy]-2',6'-dimethylbiphenyl-3-yl}methoxy)-2-fluorophenyl]propanoic acid (Example 121);
3-[2-fluoro-4-({6-isopropoxy-2',6'-dimethyl-4'-[(3-methyloxetan-3-yl)methoxy]biphenyl-3-yl}methoxy)phenyl]propanoic acid (Example 125);

or a salt thereof (preferably hydrochloride etc.).

As a salt of a compound used in the present invention, for example, metal salts, ammonium salts, salts with organic bases, salts with inorganic acids, salts with organic acids, salts with basic or acidic amino acids and the like. Preferable examples of the metal salt include alkali metal salts such as sodium salt, potassium salt and the like; alkaline earth metal salts such as calcium salt, magnesium salt, barium salt and the like; aluminum salt, and the like. Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N-dibenzylethylenediamine and the like. Preferable examples of the salt with inorganic acid include a salt with hydrochloric acid, hydrobromic acid, nitric acid, sulfuric acid, phosphoric acid and the like. Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include a salt with arginine, lysin, ornithine and the like. Preferable examples of the salt with acidic amino acid include a salt with aspartic acid, glutamic acid and the like.

Of these, a pharmacologically acceptable salt is preferable. For example, when the compound has an acidic functional group, metal salts such as alkali metal salts (e.g., sodium salt, potassium salt etc.), alkaline earth metal salts (e.g., calcium salt, magnesium salt, barium salt etc.) and the like, ammonium salt and the like are preferable, and when the compound has basic functional group, salts with inorganic acid such as hydrochloric acid, hydrobromic acid, nitric acid, sulfuric acid, phosphoric acid and the like; or salts with organic acid such as acetic acid, phthalic acid, fumaric acid, oxalic acid, tartaric acid, maleic acid, citric acid, succinic acid, methanesulfonic acid, p-toluenesulfonic acid and the like are preferable.

A prodrug of compound (I) and a salt thereof is a compound that converts to compound (I) due to the reaction by enzyme, gastric acid and the like under the physiological conditions in the body; that is, a compound that converts to compound (I) by enzymatic oxidation, reduction, hydrolysis and the like, and a compound that converts to compound (I) by hydrolysis and the like by gastric acid and the like.

Examples of a prodrug of compound (I) include a compound wherein an amino group of compound (I) is acylated, alkylated or phosphorylated (e.g., compound where amino group of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, tert-butylated and the like); a compound wherein a hydroxy group of compound (I) is acylated, alkylated, phosphorylated or borated (e.g., a compound where a hydroxy group of compound (I) is acetylated, palmitoylated, propanoylated, pivaloylated, succinylated, fumarylated, alanylated, dimethylaminomethylcarbonylated and the like); a compound wherein a carboxyl group of compound (I) is esterified or amidated (e.g., a compound where a carboxyl group of compound (I) is $C_{1-6}$ alkyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified, methylamidated and the like) and the like. Of these, a compound wherein a carboxyl group of compound (I) is esterified by $C_{1-6}$ alkyl group such as methyl, ethyl, tert-butyl and the like is preferable. These compounds can be produced from compound (I) by a method known per se.

A prodrug of compound (I) may be a compound that converts to compound (I) under physiological conditions as described in Development of Pharmaceutical Products, vol. 7, Molecule Design, 163-198, Hirokawa Shoten (1990).

Hereinafter the production methods of the compound (I) or a salt thereof of the present invention are explained.

Each symbol of the compounds in the schematic drawings of the following reaction schemes is as defined above unless particularly described. Each compound described in the reaction schemes may form a salt as long as it does not inhibit the reaction, and as such salt, those similar to the salts of compound (I) can be mentioned.

Compound (I) can be produced, for example, according to the method shown by the following reaction schemes 1-4.

Compound (I) wherein E is $E^1$ ($E^1$ is a bond, an optionally substituted $C_{1-4}$ alkylene group, —$W^1$—$N(R^6)$— ($W^1$ and $R^6$ are as defined above) or —O—) (compounds represented by the formulas (Ia') and (Ia) (to be abbreviated as compound (Ia') and compound (Ia), respectively)) can be produced, for example, according the method shown by the following Reaction Scheme 1 or a method analogous thereto.

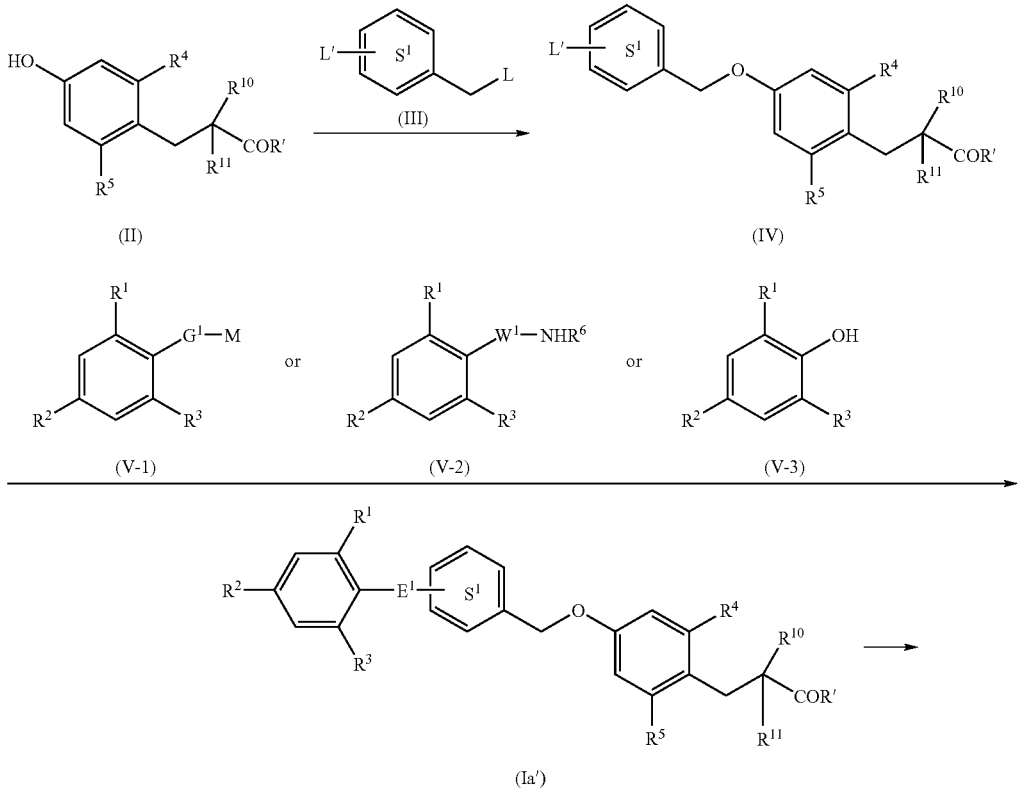

-continued

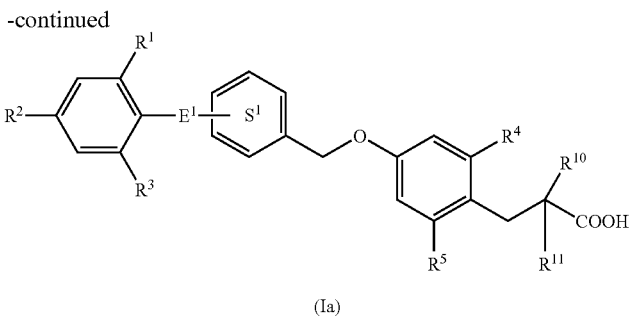

(Ia)

wherein R' is an optionally substituted $C_{1-6}$ alkoxy group, L is a leaving group or a hydroxy group, L' is a leaving group, M is a metal (e.g., potassium, sodium, lithium, magnesium, copper, mercury, zinc, thallium, boron, tin and the like, which may be formed into a complex), $G^1$ is a bond or an optionally substituted $C_{1-4}$ alkylene group (same as optionally substituted $C_{1-4}$ alkylene group for E), and the other symbols are as defined above.

As the "leaving group" for L and L', for example, a halogen atom (e.g., fluorine, chlorine, bromine, iodine), an optionally halogenated $C_{1-6}$ alkylsulfonyloxy group (e.g., methanesulfonyloxy, ethanesulfonyloxy, trichloromethanesulfonyloxy, trifluoromethanesulfonyloxy), a $C_{6-10}$ arylsulfonyloxy group optionally having substituent(s) (e.g., $C_{6-10}$ arylsulfonyloxy group (e.g., phenylsulfonyloxy, naphthylsulfonyloxy) optionally having 1 to 3 substituent(s) selected from $C_{1-6}$ alkyl group (e.g., methyl, ethyl), $C_{1-6}$ alkoxy group (e.g., methoxy, ethoxy) and nitro, and the like; as specific examples, phenylsulfonyloxy group, m-nitrophenylsulfonyloxy group, p-toluenesulfonyloxy group and the like) and the like can be mentioned.

The compounds represented by the formulas (II), (III), (V-1), (V-2) and (V-3) (to be abbreviated as compounds (II), (III), (V-1), (V-2) and (V-3), respectively) are commercially available, and can be also produced according a method known per se or a method analogous thereto.

A compound represented by the formula (IV) (to be abbreviated as compound (IV)) can be produced by reacting compound (II) with compound (III).

(i) When L is a hydroxy group, compound (IV) can be produced by subjecting compound (II) and compound (III) to Mitsunobu reaction (Synthesis, 1981, pages 1-27). In the reaction, compound (II) and compound (III) are reacted in the presence of azodicarboxylates such as diethyl azodicarboxylate, diisopropyl azodicarboxylate, 1,1'-(azodicarbonyl)dipiperidine and the like and phosphines such as triphenylphosphine, tributylphosphine and the like.

The reaction is advantageously carried out using a solvent inert to the reaction. While the solvent is not particularly limited as long as the reaction proceeds, for example, solvents such as ethers (e.g., diethyl ether, diisopropyl ether, diphenyl ether, tetrahydrofuran, 1,4-dioxane, 1,2-dimethoxyethane and the like); aromatic hydrocarbons (e.g., benzene, toluene and the like); saturated hydrocarbons (e.g., cyclohexane, hexane and the like); amides (e.g., N,N-dimethylformamide, N,N-dimethylacetamide, hexamethylphosphoric triamide and the like); halogenated hydrocarbons (e.g., dichloromethane, chloroform, carbon tetrachloride, 1,2-dichloroethane and the like); nitriles (e.g., acetonitrile, propionitrile and the like); ketones (e.g., acetone, ethyl methyl ketone and the like); sulfoxides (e.g., dimethyl sulfoxide and the like), and the like, or a mixed solvent thereof and the like are preferable.

The reaction time is generally about 5 min. to about 48 hrs., preferably about 10 min. to about 24 hrs. The reaction temperature is generally about −20 to about 200° C., preferably about 0 to about 100° C.

The amount of compound (III) to be used is about 1 to about 5 mol, preferably about 1 to about 2 mol relative to 1 mol of compound (II).

The amount of the "azodicarboxylate" and "phosphine" to be used is respectively about 1 to about 5 mol, preferably about 1 to about 2 mol, relative to 1 mol of compound (II).

(ii) When L is a leaving group, compound (IV) can be produced by reacting compound (II) with compound (III) in the presence of a base.

As the base, for example, alkali metal hydroxides such as sodium hydroxide, potassium hydroxide, lithium hydroxide and the like; alkaline earth metal hydroxides such as barium hydroxide and the like; alkali metal carbonates such as sodium carbonate, potassium carbonate, cesium carbonate and the like; alkali metal hydrogencarbonates such as sodium hydrogencarbonate and the like; acetates such as sodium acetate, ammonium acetate and the like; aromatic amines such as pyridine, lutidine and the like; tertiary amines such as triethylamine, tripropylamine, tributylamine, ethyldiisopropylamine, cyclohexyldimethylamine, 4-dimethylaminopyridine, N,N-dimethylaniline, N-methylpiperidine, N-methylpyrrolidine, N-methylmorpholine and the like; alkali metal hydrides such as sodium hydride, potassium hydride and the like; metal amides such as sodium amide, lithium diisopropylamide, lithium hexamethyldisilazide and the like; alkali metal alkoxides having 1 to 6 carbon atoms such as sodium methoxide, sodium ethoxide, sodium tert-butoxide, potassium tert-butoxide and the like, and the like can be mentioned.

The reaction is advantageously carried out using a solvent inert to the reaction. While the solvent is not particularly limited as long as the reaction proceeds, for example, solvents such as ethers (e.g., diethyl ether, diisopropyl ether, diphenyl ether, tetrahydrofuran, 1,4-dioxane, 1,2-dimethoxyethane and the like); aromatic hydrocarbons (e.g., benzene, toluene and the like); saturated hydrocarbons (e.g., cyclohexane, hexane and the like); amides (e.g., N,N-dimethylformamide, N,N-dimethylacetamide, hexamethylphosphoric triamide and the like); halogenated hydrocarbons (e.g., dichloromethane, chloroform, carbon tetrachloride, 1,2-dichloroethane and the like); nitriles (e.g., acetonitrile, propionitrile and the like); esters (e.g., methyl acetate, ethyl acetate, butyl acetate and the like); sulfoxides (e.g., dimethyl sulfoxide and the like); water and the like, or a mixed solvent thereof and the like are preferable.

The amount of compound (III) to be used is about 0.8 to 10 mol, preferably about 0.9 to 2 mol, relative to 1 mol of compound (II). The amount of the base to be used is about 1 to 10 mol, preferably about 1 to 3 mol, relative to 1 mol of compound (II).

The reaction time is generally about 10 min. to about 12 hrs., preferably about 20 min. to about 6 hrs. The reaction temperature is generally about −50 to about 150° C., preferably about −20 to about 100° C.

Compound (Ia') can be produced by reacting compound (IV) with compound (V-1) or compound (V-2) or compound (V-3) (unless otherwise specified, these are collectively referred to as compound (V)).

The reaction of compound (IV) with compound (V) is generally carried out in the presence of a base. As the base, alkali metal hydrides (e.g., sodium hydride, potassium hydride and the like); alkali metal hydroxides (e.g., lithium hydroxide, sodium hydroxide, potassium hydroxide and the like); alkaline earth metal hydroxides (e.g., magnesium hydroxide, calcium hydroxide and the like); alkali metal carbonates (e.g., sodium carbonate, potassium carbonate and the like); alkali metal hydrogencarbonates (e.g., sodium hydrogencarbonate, potassium hydrogencarbonate and the like); alkali metal alkoxides having 1 to 6 carbon atoms (e.g., sodium methoxide, sodium ethoxide, sodium tert-butoxide and the like); organic bases (e.g., trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like); organic lithiums (e.g., methyllithium, n-butyllithium, sec-butyllithium, tert-butyllithium and the like); lithium amides (e.g., lithium diisopropylamide and the like), and the like can be mentioned.

The reaction of compound (IV) with compound (V) is advantageously carried out using a solvent inert to the reaction. While the solvent is not particularly limited as long as the reaction proceeds, solvents such as alcohols (e.g., methanol, ethanol, propanol, isopropanol, butanol, tert-butanol and the like); ethers (e.g., 1,4-dioxane, tetrahydrofuran, diethyl ether, tert-butyl methyl ether, diisopropyl ether, ethyleneglycol-dimethylether and the like); esters (e.g., ethyl formate, ethyl acetate, n-butyl acetate and the like); halogenated hydrocarbons (e.g., dichloromethane, chloroform, carbon tetrachloride, trichloroethylene and the like); hydrocarbons (e.g., n-hexane, benzene, toluene, xylene and the like); amides (e.g., formamide, N,N-dimethylformamide, N,N-dimethylacetamide and the like); nitriles (e.g., acetonitrile, propionitrile and the like); sulfoxides (e.g., dimethyl sulfoxide and the like); sulfolane; hexamethylphosphoric triamide; water and the like, a mixed solvent thereof and the like are preferable.

The reaction of compound (IV) with compound (V) can be generally promoted by the use of a metal catalyst. As the metal catalyst, metal complexes having various ligands can be used and, for example, palladium compounds [e.g., palladium(II) acetate, tetrakis(triphenylphosphine)palladium(0), bis(triphenylphosphine)palladium(II) chloride, dichlorobis(triethylphosphine)palladium(0), tris(dibenzylideneacetone)dipalladium-2,2'-bis(diphenylphosphino)-1,1'-binaphthyl, a complex of palladium(II) acetate and 1,1'-bis(diphenylphosphino)ferrocene, and the like], nickel compounds [e.g., tetrakis(triphenylphosphine)nickel(0), bis(triethylphosphine)nickel(II) chloride, bis(triphenylphosphine)nickel(II) chloride and the like], rhodium compounds [e.g., tris(triphenylphosphine)rhodium(III) chloride and the like], cobalt compounds, copper compounds [e.g., copper oxide, copper(II) chloride and the like], platinum compounds and the like can be mentioned. Of these, palladium compounds, nickel compounds and copper compounds are preferable. The amount of the metal catalyst to be used is about 0.000001 to 5 mol, preferably about 0.0001 to 1 mol, relative to 1 mol of compound (IV). When a metal catalyst unstable to oxygen is used in this reaction, the reaction is preferably carried out in an inactive gas (e.g., argon gas or nitrogen gas) stream.

The amount of compound (V) to be used is about 0.8 to 10 mol, preferably about 0.9 to 2 mol, relative to 1 mol of compound (IV). The amount of the base to be used is about 1 to about 20 mol, preferably about 1 to about 5 mol, relative to 1 mol of compound (IV).

The reaction temperature is about −10° C. to about 250° C., preferably about 0° C. to about 150° C.

While the reaction time varies depending on the kinds of compound (IV), compound (V), metal catalyst, base and solvent, reaction temperature and the like, it is generally about 1 min. to about 200 hrs., preferably about 5 min. to about 100 hrs.

Compound (Ia) can be produced by subjecting compound (Ia') to hydrolysis reaction. The hydrolysis reaction is carried out using an acid or a base according to a conventional method.

As the acid, for example, mineral acids (e.g., hydrochloric acid, sulfuric acid and the like); Lewis acids (e.g., boron trichloride, boron tribromide and the like); organic acids (e.g., trifluoroacetic acid, p-toluenesulfonic acid and the like), and the like can be mentioned. Lewis acid can be used concurrently with thiol or sulfide.

As the base, for example, alkali metal hydroxides (e.g., sodium hydroxide, potassium hydroxide, barium hydroxide and the like); alkali metal carbonates (e.g., sodium carbonate, potassium carbonate and the like); alkali metal alkoxides having 1 to 6 carbon atoms (e.g., sodium methoxide, sodium ethoxide, potassium tert-butoxide and the like); organic bases (e.g., triethylamine, imidazole, formamidine and the like), and the like can be mentioned. The amount of the acid and base to be used is about 0.5 to 10 mol, preferably about 0.5 to 6 mol, relative to 1 mol of compound (Ia').

The hydrolysis reaction is carried out without solvent, or using a solvent inert to the reaction. While the solvent is not particularly limited as long as the reaction proceeds, for example, solvents such as alcohols (e.g., methanol, ethanol, propanol and the like); aromatic hydrocarbons (e.g., benzene, toluene and the like); saturated hydrocarbons (e.g., cyclohexane, hexane and the like); organic acids (e.g., formic acid, acetic acid and the like); ethers (e.g., tetrahydrofuran, 1,4-dioxane, 1,2-dimethoxyethane and the like); amides (e.g., N,N-dimethylformamide, N,N-dimethylacetamide and the like); halogenated hydrocarbons (e.g., dichloromethane, chloroform, carbon tetrachloride, 1,2-dichloroethane and the like); nitriles (e.g., acetonitrile, propionitrile and the like); ketones (e.g., acetone, ethyl methyl ketone and the like); sulfoxides (e.g., dimethyl sulfoxide and the like); water and the like, a mixed solvent thereof and the like are preferable.

The reaction time is generally 10 min. to 60 hrs., preferably 10 min. to 12 hrs. The reaction temperature is generally −10 to 200° C., preferably 0 to 120° C.

Compound (I) wherein R is an optionally substituted $C_{1-6}$ alkoxy group or a hydroxy group (compound represented by the formula (Ib') or (Ib) (to be abbreviated as compound (Ib') or compound (Ib), respectively)), can be produced, for example, according to the method shown by the following Reaction Scheme 2 or a method analogous thereto.

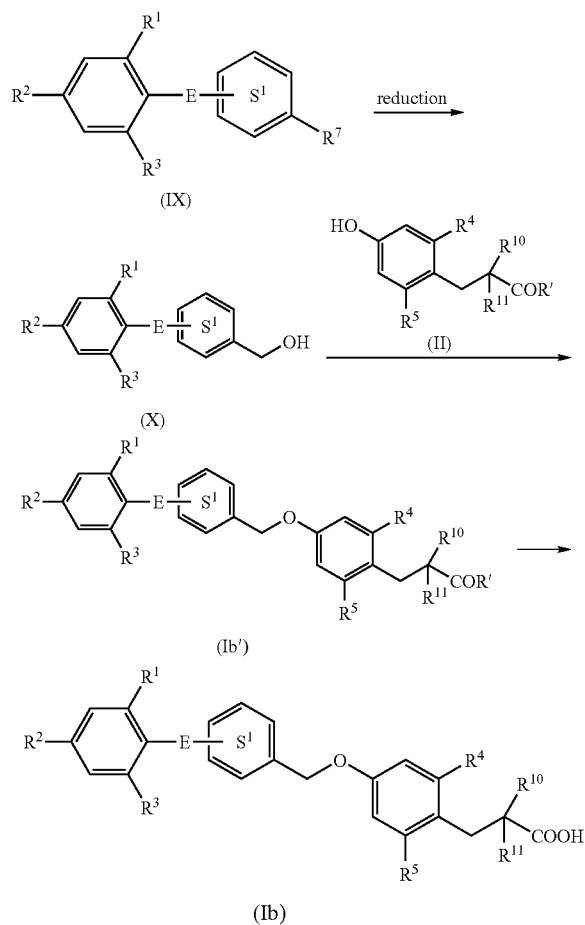

wherein $R^7$ is an optionally substituted $C_{1-4}$ alkoxy-carbonyl group or a formyl group, the other symbols are as defined above. As the "optionally substituted $C_{1-4}$ alkoxy-carbonyl group" for $R^7$, $C_{1-4}$ alkoxy-carbonyl group optionally having 1 to 3 substituent(s) such as phenyl group, halogen atom, $C_{1-6}$ alkoxy group and the like (e.g., methoxycarbonyl, ethoxycarbonyl, benzyloxycarbonyl, 2-(ethoxy)ethoxycarbonyl) and the like can be mentioned.

A compound represented by the formula (X) (to be abbreviated as compound (X)) can be produced by subjecting a compound represented by the formula (IX) (to be abbreviated as compound (IX)) to reduction reaction.

The reduction reaction is carried out using a reduction agent according to a conventional method. As the reduction agent, for example, metal hydrides (e.g., aluminum hydride, diisobutylaluminum hydride, tributyltin hydride and the like); metal hydride complexes (e.g., lithium aluminum hydride, sodium borohydride and the like); borane complexes (e.g., borane tetrahydrofuran complex, borane dimethylsulfide complex and the like); alkyl boranes (e.g., thexylborane, disiamylborane and the like); diborane; metals (e.g., zinc, aluminum, tin, iron and the like); alkali metals (e.g., sodium, lithium and the like)/liquid ammonia (Birch reduction) and the like can be mentioned. The amount of the reduction agent to be used is appropriately determined according to the kind of the reduction agent. For example, the amount of the metal hydride or metal hydride complex to be used is about 0.25 to about 10 mol, preferably about 0.5 to about 5 mol, relative to 1 mol of compound (IX), the amount of the borane complex, alkyl boran or diborane to be used is about 1 to about 10 mol, preferably about 1 to about 5 mol, relative to 1 mol of compound (IX), and the amount of the metal (containing alkali metal used for Birch reduction) to be used is about 1 to about 20 equivalents, preferably about 1 to about 5 equivalents, relative to 1 equivalent of compound (IX).

The reduction reaction is advantageously carried out using a solvent inert to the reaction. While the solvent is not particularly limited as long as the reaction proceeds, for example, solvents such as alcohols (e.g., methanol, ethanol, propanol, tert-butanol and the like); ethers (e.g., diethyl ether, diisopropyl ether, diphenyl ether, tetrahydrofuran, 1,4-dioxane, 1,2-dimethoxyethane and the like); aromatic hydrocarbons (e.g., benzene, toluene and the like); saturated hydrocarbons (e.g., cyclohexane, hexane and the like); amides (e.g., N,N-dimethylformamide, N,N-dimethylacetamide, hexamethylphosphoric triamide and the like); organic acids (e.g., formic acid, acetic acid, propionic acid, trifluoroacetic acid, methanesulfonic acid and the like), and the like, a mixed solvent thereof and the like are preferable.

While the reaction time varies depending on the kind and amount of the reducing agent or the activity and amount of the catalyst, it is generally about 1 hr to about 100 hrs., preferably about 1 hr to about 50 hrs. The reaction temperature is generally about −20 to about 120° C., preferably about 0 to about 80° C.

Compound (Ib') can be produced by reacting compound (II) and compound (X) according to a method similar to Mitsunobu reaction of compound (II) with compound (III) in the Reaction Scheme 1.

Compound (Ib) can be produced from compound (Ib') according to a method similar to the hydrolysis reaction of compound (Ia') in the Reaction Scheme 1.

Compound (IX) wherein E is $E^2$ ($E^2$ is $G^1$ ($G^1$ is as defined above), —N($R^6$)—$W^2$— ($R^6$ and $W^2$ are as defined above) or —O—), (to be abbreviated as compound (IX')), can be produced, for example, according to the method shown by the following Reaction Scheme 2' or a method analogous thereto.

The compounds represented by the formula (VII), (VIII-1), (VIII-2) and (VIII-3) (to be abbreviated as compound (VII), compound (VIII-1), compound (VIII-2) and compound (VIII-3), respectively) are commercially easily available, and can be also produced according to a method known per se or a method analogous thereto.

Reaction Scheme 2'

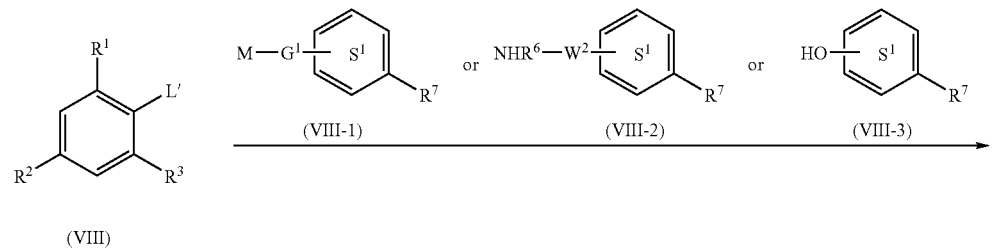

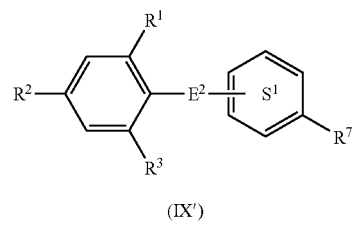

(IX')

Compound (IX') can be produced by reacting compound (VII) with compound (VIII-1), compound (VIII-2) or compound (VIII-3) (unless otherwise specified, these are collectively referred to as compound (VIII)) according to a method similar to the reaction of compound (IV) with compound (V) in the Reaction Scheme 1.

Compound (I) wherein E is $E^3$ ($E^3$ is $—W^1—O—W^2—$, $—W^1—S—W^2—$ or $—W^1—N(R^6)—W^2—$ ($W^1$, $W^2$ and $R^6$ are as defined above)), (compounds represented by the formula (Ic') and (Ic) (to be abbreviated as compound (Ic') and compound (Ic), respectively)), can be produced, for example, according to the method shown by the following Reaction Scheme 3 or a method analogous thereto.

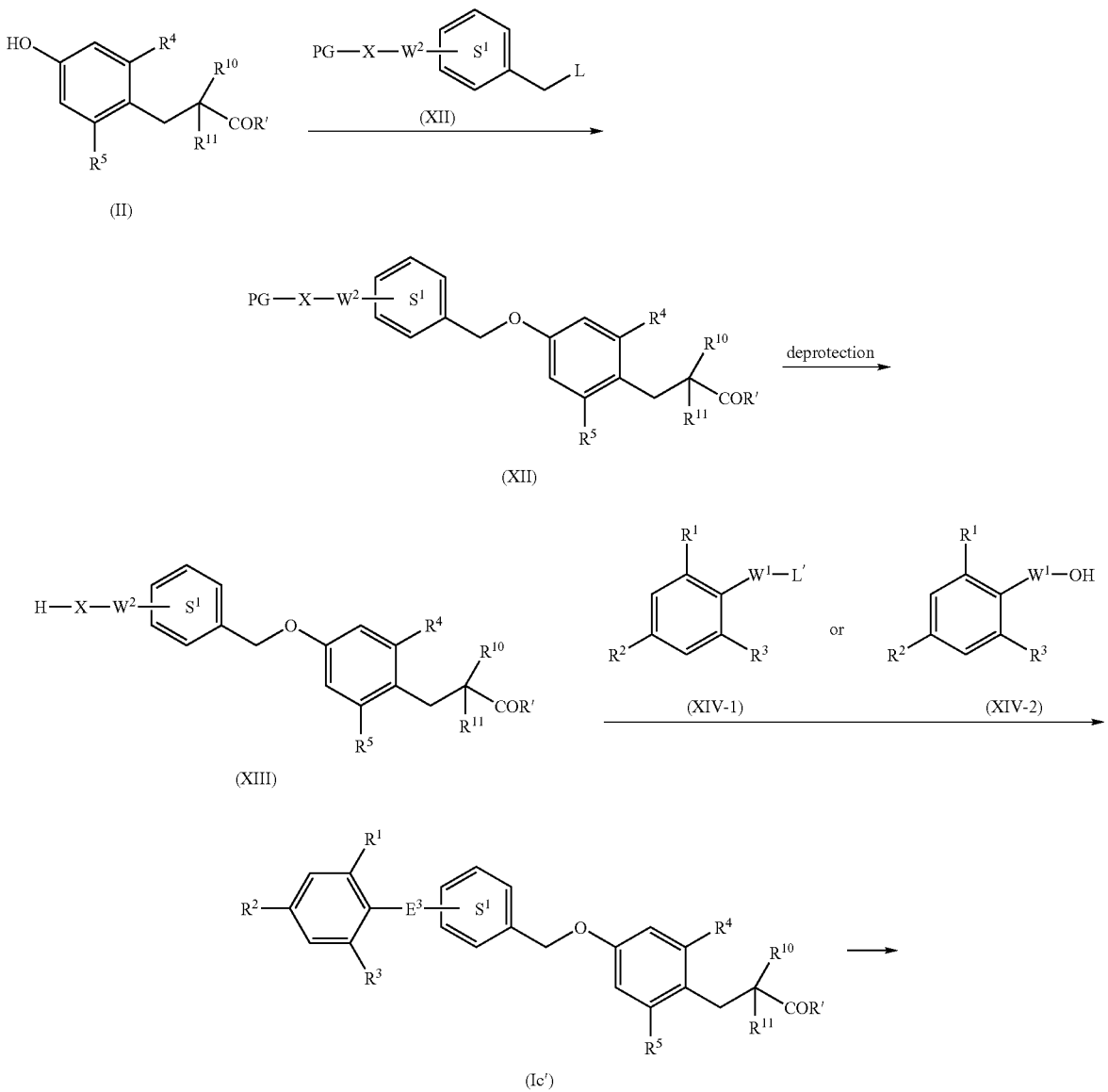

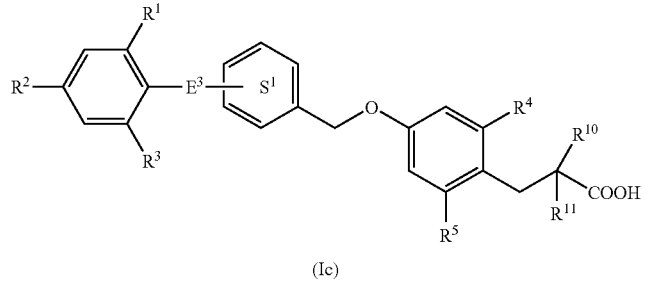

(Ic)

wherein PG is a protecting group, X is —O—, —S— or —N(R⁶)— (R⁶ is as defined above), and other symbols are as defined above.

As the protecting group for PG, the hydroxy-protecting group, amino-protecting group and mercapto-protecting group to be mentioned later can be used.

Compounds represented by the formula (XI), (XIV-1) and (XIV-2) (to be abbreviated as compound (XI), compound (XIV-1) and compound (XIV-2), respectively) are commercially easily available, and can be also produced according to a method known per se or a method analogous thereto.

A compound represented by the formula (XII) (to be abbreviated as compound (XII)) can be produced by reacting compound (II) with compound (XI) according to a method similar to the reaction of compound (II) with compound (III) in the Reaction Scheme 1.

A compound represented by the formula (XIII) (to be abbreviated as compound (XIII)) can be produced by deprotecting compound (XII) according to a deprotection reaction known per se or a method analogous thereto.

Compound (Ic') wherein $E^3$ is —$W^1$—O—$W^1$—, —$W^1$—S—$W^2$— or —$W^1$—N(R⁶)—$W^2$—, $W^2$ and R⁶ are as defined above, and $W^1$ is an optionally substituted $C_{1-3}$ alkylene group can be produced by reacting compound (XIII) with compound (XIV-1) according to a method similar to the reaction of compound (II) with compound (III) wherein L is a leaving group in the Reaction Scheme 1.

Compound (Ic') wherein $E^3$ is —$W^1$—O—$W^2$— or —$W^1$—S—$W^2$—, and at least one of $W^1$ and $W^2$ is a bond can be also produced by reacting compound (XIII) wherein X is —O— or —S— with compound (XIV-2) according to a method similar to the reaction of Mitsunobu reaction of compound (II) with compound (III) in the Reaction Scheme 1.

Compound (Ic) can be produced from compound (Ic') according to a method similar to the hydrolysis reaction of compound (Ia') in the Reaction Scheme 1.

Compound (I) wherein $R^2$ is a substituted hydroxy group, a substituted amino group or a substituted mercapto group, namely, compound (I) wherein $R^2$ is $R^{2'}$—Y— [Y is —O—, —S— or —N(R⁴)— (R⁴ is a hydrogen atom or a substituent possessed by amino group (specifically, a substituent possessed by the amino group of the "optionally substituted amino group" for $R^2$), and $R^{2'}$ is a substituent (specifically, when Y is —O—, a substituent possessed by the hydroxy group of the "optionally substituted hydroxy group" for $R^2$, when Y is —S—, a substituent possessed by the mercapto group of the "optionally substituted mercapto group" for $R^2$, when Y is —N(R⁴)—, a substituent possessed by the amino group of the "optionally substituted amino group" for $R^2$)], (compounds represented by the formula (If') and (Id) (to be abbreviated as compound (If') and compound (Id), respectively)), can be produced, for example, according to the method shown by the following Reaction Scheme 4 or a method analogous thereto.

Reaction Scheme 4

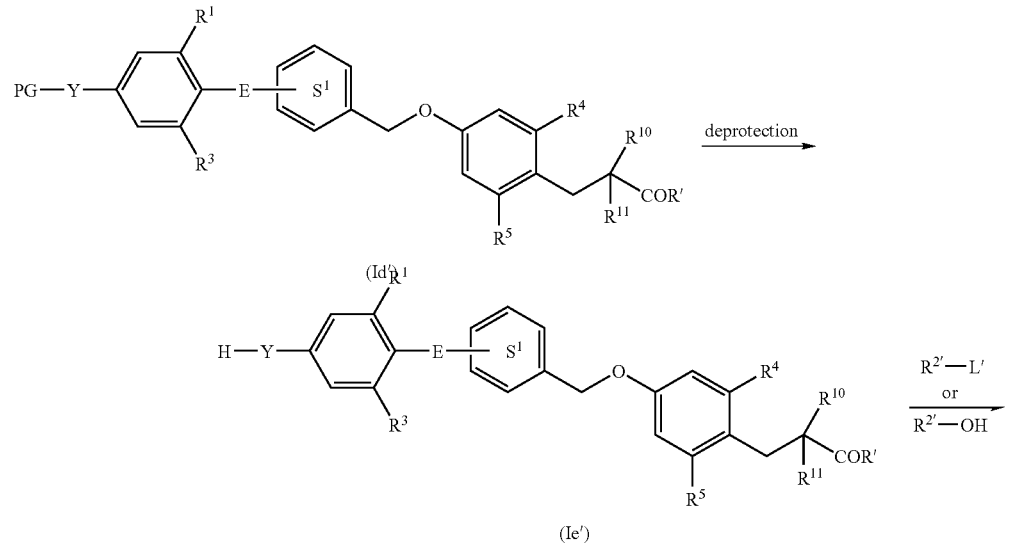

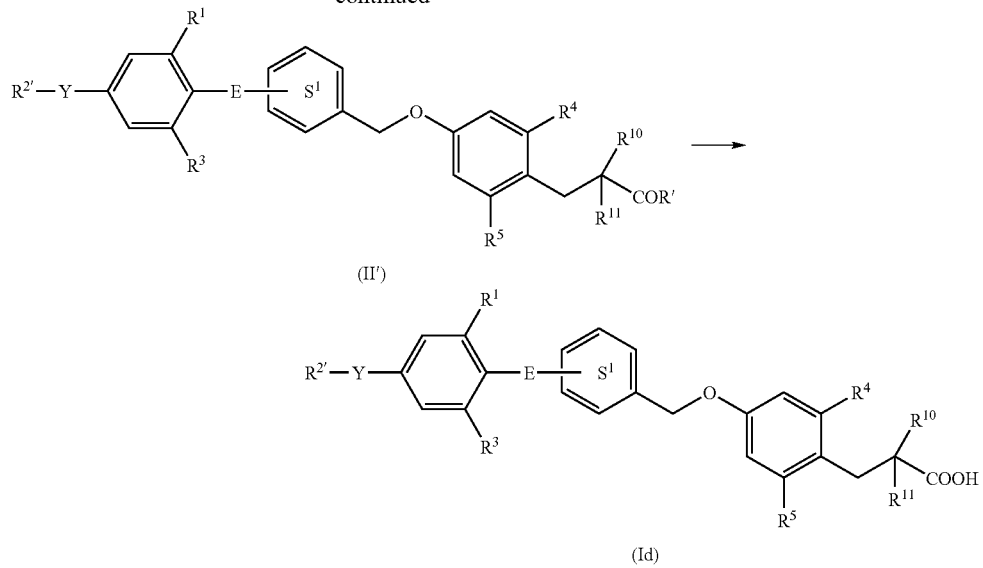

wherein each symbol is as defined above.

A compound represented by the formula (Id') (to be abbreviated as compound (Id')) can be produced according to a method similar to the aforementioned compound (Ia'), compound (Ib') or compound (Ic').

A compound represented by the formula (Ie') (to be abbreviated as compound (Ie')) can be produced by subjecting compound (Id') to a deprotection reaction known per se.

Compound (If') can be produced by reacting compound (Ie') with a compound represented by the formula: R$^{2'}$-L', according to a method similar to the reaction of compound (II) with compound (III) wherein L is a leaving group in the Reaction Scheme 1.

Compound (If') wherein Y is —O— or —S— can be also produced by reacting compound (Ie') wherein Y is —O— or —S— with a compound represented by the formula: R$^{2'}$—OH according to a method similar to Mitsunobu reaction of compound (II) with compound (III) in the Reaction Scheme 1.

Compound (Id) can be produced from compound (If') according to a method similar to the hydrolysis reaction of compound (Ia') in the Reaction Scheme 1.

In each of the aforementioned reactions, when the starting compound has amino group, carboxyl group, hydroxy group or mercapto group as a substituent, a protecting group generally used in peptide chemistry and the like may be introduced into these groups. By removing the protecting group as necessary after the reaction, the objective compound can be obtained.

As the amino-protecting group, for example, formyl group; $C_{1-6}$ alkyl-carbonyl group (e.g., acetyl, ethylcarbonyl and the like), phenylcarbonyl group, $C_{1-6}$ alkoxy-carbonyl group (e.g., methoxycarbonyl, ethoxycarbonyl, tert-butoxycarbonyl (Boc) and the like), allyloxycarbonyl (Alloc) group, phenyloxycarbonyl group, fluorenylmethoxycarbonyl (Fmoc) group, $C_{7-10}$ aralkyl-carbonyl group (e.g., benzylcarbonyl and the like), $C_{7-10}$ aralkyloxy-carbonyl group (e.g., benzyloxycarbonyl (Z) and the like), $C_{7-10}$ aralkyl group (e.g., benzyl and the like), trityl group, phthaloyl group, dithiasuccinoyl group or N,N-dimethylaminomethylene group, each of which optionally has substituent(s), can be mentioned. As the substituent, phenyl group, halogen atom, $C_{1-6}$ alkyl-carbonyl group (e.g., acetyl, ethylcarbonyl, butylcarbonyl and the like), $C_{1-6}$ alkoxy group optionally substituted by a halogen atom (e.g., methoxy, ethoxy, trifluoromethoxy and the like), nitro group and the like can be used. The number of the substituent is about 1 to 3.

As the carboxy-protecting group, for example, $C_{1-6}$ alkyl group, allyl group, benzyl group, phenyl group, trityl group or trialkylsilyl group and the like, each of which optionally has substituent(s), can be mentioned. As the substituent, halogen atom, formyl group, $C_{1-6}$ alkyl-carbonyl group (e.g., acetyl, ethylcarbonyl, butylcarbonyl and the like), $C_{1-6}$ alkoxy group optionally substituted by a halogen atom (e.g., methoxy, ethoxy, trifluoromethoxy and the like), nitro group and the like can be used. The number of the substituent is about 1 to 3.

As the hydroxy-protecting group, for example, $C_{1-6}$ alkyl group, $C_{7-20}$ aralkyl group (e.g., benzyl, trityl and the like), formyl group, $C_{1-6}$ alkyl-carbonyl group (e.g., acetyl, ethylcarbonyl and the like), benzoyl group, $C_{7-10}$ aralkyl-carbonyl group (e.g., benzylcarbonyl and the like), 2-tetrahydropyranyl group, tetrahydrofuranyl group or trialkylsilyl group (e.g., trimethylsilyl, tert-butyldimethylsilyl, diisopropylethylsilyl and the like) and the like, each of which optionally has substituent(s), can be mentioned. As the substituent, halogen atom, $C_{1-6}$ alkyl group, phenyl group, $C_{7-10}$ aralkyl group (e.g., benzyl and the like), $C_{1-6}$ alkoxy group, nitro group and the like can be used. The number of the substituent is about 1 to 4.

As the mercapto-protecting group, for example, $C_{1-6}$ alkyl group, $C_{1-6}$ alkyl-carbonyl group (e.g., acetyl, ethylcarbonyl and the like), $C_{7-20}$ aralkyl group (e.g., benzyl, trityl and the like) and the like, each of which optionally has substituent(s), can be mentioned. As the substituent, halogen atom, $C_{1-6}$ alkyl group, phenyl group, $C_{7-10}$ aralkyl group (e.g., benzyl and the like), $C_{1-6}$ alkoxy group, nitro group and the like can be used. The number of the substituent is about 1 to 4.

For elimination of the protecting group, a method known per se or a method analogous thereto is used. For example, treatment with acid, base, reduction, ultraviolet rays, hydrazine, phenylhydrazine, sodium N-methyldithiocarbamate, tetrabutylammonium fluoride, palladium acetate and the like are used.

Compound (I) obtained in this manner, other reaction intermediates and starting material compounds thereof can be isolated or purified from the reaction mixture by a method known per se, such as extraction, concentration, neutralization, filtration, distillation, recrystallization, column chromatography, thin layer chromatography, preparative high pressure liquid chromatography (preparative HPLC), intermediate pressure preparative liquid chromatography (intermediate pressure preparative LC) and the like.

The salt of compound (I) can be produced according to a method known per se. For example, when compound (I) is a basic compound, the salt can be produced by adding an inorganic acid or an organic acid, or when compound (I) is an acidic compound, by adding an organic base or an inorganic base.

When compound (I) has optical isomers, these respective optical isomers and mixtures thereof are naturally encompassed in the scope of the present invention, and where desired, these isomers can be also subjected to optical resolution or individually produced according to a method known per se.

When compound (I) is present as a configurational isomer (stereoisomer), diastereomer, conformer or the like, each can be isolated by the above separation and purification methods on demand. In addition, when compound (I) is in the form of racemates, they can be separated into S- and R-forms by any conventional optical resolution.

When compound (I) includes stereoisomers, both the isomers alone and mixtures of each isomers are included in the scope of the present invention.

In addition, compound (I) may be a hydrate or non-hydrate.

Compound (I) may be labeled with an isotope (e.g., $^{3}H$, $^{14}C$, $^{35}S$ and the like) or the like.

Compound (I), a salt thereof and a prodrug thereof (hereinafter sometimes to be abbreviated as the compound of the present invention) show GPR40 receptor function modulating action (GPR40 receptor agonist activity and GPR40 receptor antagonist activity), particularly GPR40 receptor agonist activity, show low toxicity and a fewer side effects (e.g., acute toxicity, chronic toxicity, genotoxicity, developmental toxicity, cardiac toxicity, drug interaction, cancinogenicity). Therefore, they are useful as a safe GPR40 receptor function modulator, preferably GPR40 agonist.

A pharmaceutical agent containing the compound of the present invention shows a superior GPR40 receptor function modifying action in mammal (e.g., mouse, rat, hamster, rabbit, cat, dog, bovine, sheep, monkey, human etc.), and is useful as a modulator of physiological function in which GPR40 receptor is involved or an agent for the prophylaxis or treatment of disease state or disease in which GPR40 receptor is involved.

To be specific, the pharmaceutical agent containing the compound of the present invention is useful as an insulin secretion modulator (preferably insulin secretagogue), hypoglycemic drug and pancreatic β cell protector.

Moreover, the pharmaceutical agent containing the compound of the present invention is useful as an agent for the prophylaxis or treatment of diseases such as diabetes, impaired glucose tolerance, ketosis, acidosis, diabetic neuropathy, diabetic nephropathy, diabetic retinopathy, macular edema, hyperlipidemia, genital disorder, skin disease, arthropathy, osteopenia, arteriosclerosis, thrombotic disease, dyspepsia, memory and learning disorder, depression, depression and mania, schizophrenia, attention deficit hyperactivity disorder, visual disorder, appestat disorder (e.g., hyperorexia), obesity, hypoglycemia, hypertension, edema, insulin resistance, unstable diabetes, fatty atrophy, insulin allergy, insulinoma, lipotoxicity, pancreatic fatigue, hyperinsulinemia, cancers (e.g., breast cancer), metabolic syndrome, immune diseases (e.g., immunodeficiency), inflammatory disease (e.g., enteritis, arthritis, allergy), multiple sclerosis, acute kidney failure and the like; particularly, diseases such as diabetes, impaired glucose tolerance, ketosis, acidosis, diabetic neuropathy, diabetic nephropathy, diabetic retinopathy, macular edema, hyperlipidemia, genital disorder, skin disease, arthropathy, osteopenia, arteriosclerosis, thrombotic disease, dyspepsia, memory and learning disorder and the like. Here, diabetes includes type 1 diabetes, type 2 diabetes and pregnancy diabetes can be mentioned. In addition, hyperlipidemia includes hypertriglyceridemia, hypercholesterolemia, hypoHDL-emia, postprandial hyperlipidemia and the like.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) reported new diagnostic criteria of diabetes in 1997 and WHO in 1998.

According to these reports, diabetes is a condition showing a fasting blood glucose level (glucose concentration of intravenous plasma) of not less than 126 mg/dl and a 75 g oral glucose tolerance test 2 h level (glucose concentration of intravenous plasma) of not less than 200 mg/dl.

According to the above-mentioned reports, impaired glucose tolerance is a condition showing a fasting blood glucose level (glucose concentration of intravenous plasma) of less than 126 mg/dl and a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 h level (glucose concentration of intravenous plasma) of less than 140 mg/dl is called IFG (Impaired Fasting Glycemia).

The compound of the present invention can be also used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycemia) into diabetes.

The compound of the present invention is also useful as a therapeutic agent for diabetes with sulfonylurea secondary failure and affords a superior insulin secretion effect and a hypoglycemic effect for diabetic patients for whom sulfonylurea compounds and fast-acting insulin secretagogues fail to provide an insulin secretion effect, and therefore, fail to provide a sufficient hypoglycemic effect.

As the sulfonylurea compound here, a compound having a sulfonylurea skeleton or a derivative thereof (e.g., tolbutamide, glibenclamide, gliclazide, chlorpropamide, tolazamide, acetohexamide, glyclopyramide, glimepiride, glipizide, glybuzole and the like) can be mentioned.

As the fast-acting insulin secretagogue, a compound that promotes insulin secretion from pancreatic β cell in the same manner as a sulfonylurea compound, though it does not have a sulfonylurea skeleton, such as glinide compounds (e.g., repaglinide, senaglinide, nateglinide, mitiglinide, a calcium salt hydrate thereof etc.), and the like, can be mentioned.

The pharmaceutical agent comprising the compound of the present invention shows low toxicity and can be safely administered orally or parenterally (e.g., topical, rectal, intravenous administration etc.) in the form of the compound of the present invention as it is or after admixing with a pharmacologically acceptable carrier to give a pharmaceutical preparation according to a method known per se used for the general production method for pharmaceutical preparations.

The dosage form of the aforementioned pharmaceutical preparation is, for example, an oral agent such as tablets (inclusive of sublingual tablets and orally disintegrable tablets), capsules (inclusive of soft capsules and micro capsules), granules, powders, troches, syrups, emulsions, suspensions and the like; or a parenteral agent such as injections (e.g., subcutaneous injections, intravenous injections, intramuscular injections, intraperitoneal injections, drip infusions etc.), external agents (e.g., transdermal preparations, ointments etc.), suppositories (e.g., rectal suppositories, vaginal suppositories etc.), pellets, nasal preparations, pulmonary preparations (inhalations), ophthalmic preparations and the like.

These agents may be controlled-release preparations such as rapid-release preparations and sustained-release preparations (e.g., sustained-release microcapsules).

The content of the compound of the present invention in a pharmaceutical preparation of the present invention is about 0.01 to about 100% by weight relative to the whole preparation. The dose of the compound of the present invention varies depending on administration subjects, administration route, diseases, condition and the like. When the compound is orally administered to an adult patient with diabetes (body weight about 60 kg), about 0.01 to about 30 mg/kg body weight per day, preferably about 0.1 to about 20 mg/kg body weight per day, more preferably about 1 to about 20 mg/kg body weight per day, which may be given at once or several portions a day.

Various organic or inorganic carriers conventionally used as materials for pharmaceutical preparations are used as a pharmacologically acceptable carrier, which are added as excipient, lubricant, binder and disintegrant for solid preparations; and solvent, dissolution aids, suspending agent, isotonicity agent, buffer and soothing agent and the like for liquid preparations. Where necessary, additive such as preservative, antioxidant, coloring agent, sweetening agent, adsorbing agent, wetting agent and the like can be used.

As the excipient, for example, lactose, sucrose, D-mannitol, starch, corn starch, crystalline cellulose, light silicic anhydride and the like can be mentioned.

As the lubricant, for example, magnesium stearate, calcium stearate, talc, colloidal silica and the like can be mentioned.

As the binder, for example, crystalline cellulose, sucrose, D-mannitol, dextrin, hydroxypropylcellulose, hydroxypropylmethylcellulose, polyvinylpyrrolidone, starch, sucrose, gelatin, methylcellulose, carboxymethylcellulose sodium and the like can be mentioned.

As the disintegrant, for example, starch, carboxymethylcellulose, carboxymethylcellulose calcium, carboxymethylstarch sodium, L-hydroxypropylcellulose and the like can be mentioned.

As the solvent, for example, water for injection, alcohol, propyleneglycol, macrogol, sesame oil, corn oil, olive oil and the like can be mentioned.

As the dissolution aids, for example, polyethylene glycol, propyleneglycol, D-mannitol, benzyl benzoate, ethanol, trisaminomethane, cholesterol, triethanolamine, sodium carbonate, sodium citrate and the like can be mentioned.

As the suspending agent, for example, surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like, and the like can be mentioned.

As an isotonicity agent, for example, glucose, D-sorbitol, sodium chloride, glycerin, D-mannitol and the like can be mentioned.

As the buffer, for example, buffers such as phosphate, acetate, carbonate, citrate and the like, and the like can be mentioned.

As the soothing agent, for example, benzyl alcohol and the like can be mentioned.

As the preservative, for example, p-hydroxybenzoates, chlorobutanol, benzyl alcohol, phenethyl alcohol, dehydroacetic acid, sorbic acid and the like can be mentioned.

As the antioxidant, for example, sulfite, ascorbic acid, α-tocopherol and the like can be mentioned.

As the coloring agent, for example, water-soluble edible tar pigments (e.g., foodcolors such as Food Color Red Nos. 2 and 3, Food Color Yellow Nos. 4 and 5, Food Color Blue Nos. 1 and 2 and the like), water insoluble lake pigments (e.g., aluminum salt of the aforementioned water-soluble edible tar pigment and the like), natural pigments (e.g., β-carotene, chlorophil, red iron oxide etc.) and the like can be mentioned.

As the sweetening agent, for example, saccharin sodium, dipotassium glycyrrhizinate, aspartame, stevia and the like can be mentioned.

The compound of the present invention can be used in combination with drugs such as a therapeutic agent of diabetes, a therapeutic agent of diabetic complications, a therapeutic agent of hyperlipidemia, an antihypertensive agent, an antiobestic agent, a diuretic, a chemotherapeutic agent, an immunotherapeutic agent, an antiinflammatory drug, an antithrombotic agent, a therapeutic agent of osteoporosis, a vitamin, an antidementia agent, a therapeutic agent for incontinentia or pollakiuria, a therapeutic agent for dysurea and the like (hereinafter to be referred to as drug X).

As the therapeutic agent for diabetes, insulin preparations (e.g., animal insulin preparations extracted from the pancreas of bovine and pig; human insulin preparations genetically synthesized using *Escherichia coli*, yeast; zinc insulin; protamine zinc insulin; fragment or derivative of insulin (e.g., INS-1 etc.), oral insulin preparation and the like), insulin sensitizers (e.g., Pioglitazone or a salt thereof (preferably hydrochloride), Rosiglitazone or a salt thereof (preferably maleate), Reglixane (JTT-501), Netoglitazone (MCC-555), GI-262570, FK-614, Rivoglitazone (CS-011), Muraglitazar (BMS-298585), compounds described in WO99/58510 (e.g., (E)-4-[4-(5-methyl-2-phenyl-4-oxazolylmethoxy)benzyloxyimino]-4-phenylbutyric acid), compounds described in WO01/38325, Tesaglitazar (AZ-242), BM-13-1258, LM-4156, MBX-102, LY-519818, MX-6054, LY-510929, Balaglitazone (NN-2344), T-131 or a salt thereof, THR-0921 etc.), α-glucosidase inhibitors (e.g., voglibose, acarbose, miglitol, emiglitate etc.), biguanides (e.g., phenformin, metformin, buformin or salts thereof (e.g., hydrochloride, fumarate, succinate) etc.), insulin secretagogues [sulfonylurea (e.g., tolbutamide, glibenclamide, gliclazide, chlorpropamide, tolazamide, acetohexamide, glyclopyramide, glimepiride etc.), repaglinide, senaglinide, mitiglinide or calcium salt hydrate thereof, nateglinide, etc.], GLP-1 receptor agonists [e.g., GLP-1, GLP-1MR agent, NN-2211, AC-2993 (exendin-4), BIM-51077, Aib(8,35)hGLP-1(7,37)NH$_2$, CJC-1131 etc.], dipeptidyl peptidase IV inhibitor (e.g., NVP-DPP-278, PT-100, P32/98, P93/01, NVP-DPP-728, LAF237, TS-021 etc.), β3 agonist (e.g., CL-316243, SR-58611-A, UL-TG-307, AJ-9677, AZ40140 etc.), amylin agonists (e.g., pramlintide etc.), phosphotyrosine phosphatase inhibitors (e.g., sodium vanadate etc.), gluconeogenesis inhibitors (e.g., glycogen phosphorylase inhibitor, glucose-6-phosphatase inhibitor, glucagon antagonist etc.), SGLT (sodium-glucose cotransporter) inhibitors (e.g., T-1095 etc.), 11β-hydroxysteroid dehydrogenase inhibitors (e.g., BVT-3498 etc.), adiponectin or agonist thereof, IKK inhibitors (e.g., AS-2868 etc.), leptin resistance improving drugs, somatostatin receptor agonists (compounds described in WO01/25228, WO03/42204, WO98/44921, WO98/45285, WO99/22735 etc.), glucokinase activators (e.g., Ro-28-1675) and the like can be mentioned.

Examples of the therapeutic agent for diabetic complications include aldose reductase inhibitors (e.g., Tolrestat, Epalrestat, Zenarestat, Zopolrestat, Fidarestat (SNK-860), AS-3201, Minalrestat (ARI-509), CT-112 etc.), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy)propyl]oxazole etc.) and the like), protein kinase C (PKC) inhibitors (e.g., ruboxistaurin mesylate; LY-333531 etc.), AGE inhibitors (e.g., ALT-945, pimagedine, pyratoxanthine, N-phenacylthiazolium bromide (ALT-766), EXO-226, ALT-711, Pyridorin, Pyridoxamine etc.), active oxygen scavengers (e.g., thioctic acid etc.), cerebral vasodilators (e.g., tiapride etc.), somatostatin receptor agonists (BIM23190) and apoptosis signal regulating kinase-1 (ASK-1) inhibitors.

Examples of the therapeutic agent of hyperlipidemia include HMG-CoA reductase inhibitor (e.g., pravastatin, simvastatin, lovastatin, atorvastatin, fluvastatin, pitavastatin, rosuvastatin and salts thereof (e.g., sodium salt, calcium salt) etc.), squalene synthase inhibitors (e.g., compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid etc.), fibrate compounds (e.g., bezafibrate, clofibrate, simfibrate, clinofibrate etc.), antioxidant (e.g., lipoic acid, probucol) and the like.

Examples of the antihypertensive agent include angiotensin converting enzyme inhibitors (e.g., captopril, enalapril, delapril etc.), angiotensin II receptor antagonists (e.g., losartan, candesartan cilexetil, eprosartan, valsartan, telmisartan, irbesartan, olmesartan medoxomil, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid etc.), calcium channel blockers (e.g., manidipine, nifedipine, amlodipine, efonidipine, nicardipine etc.), Clonidine and the like.

Examples of the antiobestic agent include antiobestic agents acting on the central nervous system (e.g., Dexfenfluramine, fenfluramine, phentermine, Sibutramine, amfepramone, dexamphetamine, Mazindol, phenylpropanolamine, clobenzorex; MCH receptor antagonists (e.g., SB-568849; SNAP-7941; compounds encompassed in WO01/82925 and WO01/87834 etc.); neuropeptide Y antagonists (e.g., CP-422935 etc.); cannabinoid receptor antagonists (e.g., SR-141716, SR-147778 etc.); ghrelin antagonist; 11β-hydroxysteroid dehydrogenase inhibitors (e.g., BVT-3498 etc.) and the like), pancreatic lipase inhibitors (e.g., orlistat, ATL-962 etc.), β3 agonists (e.g., CL-316243, SR-58611-A, UL-TG-307, AJ-9677, AZ40140 etc.), peptidic anorexiants (e.g., leptin, CNTF (Ciliary Neurotropic Factor) etc.), cholecystokinin agonists (e.g., lintitript, FPL-15849 etc.), feeding deterrent (e.g., P-57 etc.) and the like.

Examples of the diuretic include xanthine derivatives (e.g., sodium salicylate and theobromine, calcium salicylate and theobromine etc.), thiazide preparations (e.g., ethiazide, cyclopenthiazide, trichloromethyazide, hydrochlorothiazide, hydroflumethiazide, benzylhydrochlorothiazide, penflutizide, polythiazide, methyclothiazide etc.), antialdosterone preparations (e.g., spironolactone, triamterene etc.), carbonate dehydratase inhibitors (e.g., acetazolamide and the like), chlorobenzenesulfonamide preparations (e.g., chlortalidone, mefruside, indapamide etc.), azosemide, isosorbide, etacrynic acid, piretanide, bumetanide, furosemide and the like.

Examples of the chemotherapeutic agent include alkylation agents (e.g., cyclophosphamide, ifosfamide etc.), metabolic antagonists (e.g., methotrexate, 5-fluorouracil or its derivative, etc.), anti-cancer antibiotics (e.g., mitomycin, adriamycin etc.), plant-derived anti-cancer agents (e.g., vincristin, vindesine, taxol etc.), cisplatin, carboplatin, etoposide and the like. Of these, furtulon and neofurtulon, which are 5-fluorouracil derivatives, and the like are preferable.

Examples of the immunotherapeutic agent include microorganism or bacterial components (e.g., muramyl dipeptide derivative, picibanil etc.), polysaccharides having immunity potentiating activity (e.g., lentinan, sizofuran, krestin etc.), cytokines obtained by genetic engineering techniques (e.g., interferon, interleukin (IL) etc.), colony stimulating factors (e.g., granulocyte colony stimulating factor, erythropoietin etc.) and the like, with preference given to interleukins such as IL-1, IL-2, IL-12 and the like.

As the antiinflammatory drug, for example, non-steroidal antiinflammatory agents such as aspirin, acetoaminofen, indomethacin and the like can be mentioned.

Examples of the antithrombotic agent include heparin (e.g., heparin sodium, heparin calcium, dalteparin sodium etc.), warfarin (e.g., warfarin potassium etc.), anti-thrombin drugs (e.g., aragatroban etc.), thrombolytic agents (e.g., urokinase, tisokinase, alteplase, nateplase, monteplase, pamiteplase etc.), platelet aggregation inhibitors (e.g., ticlopidine hydrochloride, cilostazol, ethyl icosapentate, beraprost sodium, sarpogrelate hydrochloride etc.) and the like.

Examples of the therapeutic agent of osteoporosis include alfacalcidol, calcitriol, elcatonin, calcitonin salmon, estriol, ipriflavone, risedronate disodium, pamidronate disodium, alendronate sodium hydrate, incadronate disodium and the like.

As the vitamin, for example, vitamin $B_1$, vitamin $B_{12}$ and the like can be mentioned.

Examples of the antidementia agent include tacrine, donepezil, rivastigmine, galanthamine and the like.

Examples of the therapeutic agent for incontinentia or pollakiuria include flavoxate hydrochloride, oxybutynin hydrochloride, propiverine hydrochloride and the like.

Examples of the therapeutic agent for dysurea include acetylcholine esterase inhibitors (e.g., distigmine) and the like can be mentioned.

Furthermore, drugs having a cachexia-improving action established in animal models and clinical situations, such as cyclooxygenase inhibitors (e.g., Indometacin etc.), Progesterone derivatives (e.g., Megesterol acetate), glucosteroid (e.g., dexamethasone etc.), metoclopramide agents, tetrahydrocannabinol agents, fat metabolism improving agents (e.g., eicosapentaenoic acid etc.), growth hormones, IGF-1, or antibodies to a cachexia-inducing factor such as TNF-α, LIF, IL-6, Oncostatin M and the like, can be used in combination with the compound of the present invention.

Further, glycosylation inhibitors (e.g., ALT-711, etc.), nerve regeneration promoting drugs (e.g., Y-128, VX853, prosaptide, etc.), antidepressants (e.g., desipramine, amitriptyline, imipramine, etc.), anticonvulsants (e.g., lamotrigine, Trileptal, Keppra, Zonegran, Pregabalin, Harkoseride, carbamazepine), antiarrhythmic drugs (e.g., mexiletine), acetylcholine receptor ligands (e.g., ABT-594), endothelin receptor antagonists (e.g., ABT-627), monoamine uptake inhibitors (e.g., tramadol), narcotic analgesics (e.g., morphine), GABA receptor agonists (e.g., gabapentin, gabapentin MR agent), $\alpha_2$ receptor agonists (e.g., clonidine), local analgesics (e.g., capsaicin), antianxiety drugs (e.g., benzothiazepines), phosphodiesterase inhibitors (e.g., sildenafil), dopamine receptor agonists (e.g., apomorphine) and the like can be also used in combination with the compound of the present invention.

Two or more kinds of the above-mentioned drug X may be used in an appropriate combination.

By combining the compound of the present invention and a drug X, a superior effect such as
(1) the dose of the compound of the present invention or a drug X can be reduced as compared to single administration of the compound of the present invention or a drug X,
(2) the period of treatment can be set longer by selecting a drug X having different action and mechanism from those of the compound of the present invention,
(3) a sustained treatment effect can be designed by selecting a drug X having different action and mechanism from those of the compound of the present invention,
(4) a synergistic effect can be afforded by a combined use of the compound of the present invention and a drug X, and the like, can be achieved.

When the compound of the present invention and a drug X are used in combination, the administration time of the compound of the present invention and the drug X is not restricted, and the compound of the present invention and the drug X can be administered to an administration subject simultaneously, or may be administered at staggered times. The dosage of the drug X may be determined according to the dose clinically used, and can be appropriately selected depending on an administration subject, administration route, disease, combination and the like.

The administration mode of the compound of the present invention and drug X is not particularly restricted, as long as the compound of the present invention and the drug X are combined in administration. Examples of such administration mode include the following methods: (1) The compound of the present invention and the drug X are simultaneously formulated to give a single preparation which is administered. (2) The compound of the present invention and the drug X are separately formulated to give two kinds of preparations which are administered simultaneously by the same administration route. (3) The compound of the present invention and the drug X are separately formulated to give two kinds of preparations which are administered by the same administration route at staggered times. (4) The compound of the present invention and the drug X are separately formulated to give two kinds of preparations which are administered simultaneously by the different administration routes. (5) The compound of the present invention and the drug X are separately formulated to give two kinds of preparations which are administered by the different administration routes at staggered times (for example, the compound of the present invention and the drug X are administered in this order, or in the reverse order), and the like.

EXAMPLES

The present invention is further explained in detail by referring to the following Reference Examples, Examples, Formulation Examples and Experimental Example, which are mere working examples not to be construed as limitative and may be changed without departing from the scope of the present invention.

The term "room temperature" in the following Reference Examples and Examples indicates the range of generally from about 10° C. to about 35° C. As for "%", the yield is in mol/mol %, the solvent used for chromatography is in % by volume and other "%" is in % by weight. OH proton, NH proton etc. that could not be confirmed due to broad peak by proton NMR spectrum are not included in the data.

The other symbols used herein mean the following:
s: singlet
d: doublet
t: triplet
q: quartet
m: multiplet
br: broad
J: coupling constant
Hz: Hertz
$CDCl_3$: deuterated chloroform
$^1$H NMR: proton nuclear magnetic resonance In the following Reference Examples and Examples, mass spectrum (MS) and nuclear magnetic resonance spectrum (NMR) were measured under the following conditions.
MS measurement tools: Waters Corporation ZMD, Waters Corporation ZQ2000 or Micromass Ltd., platform II.
ionization method: Electron Spray Ionization (ESI) or Atmospheric Pressure Chemical Ionization (APCI). Unless specifically indicated, ESI was used.
NMR measurement tools: Varian Gemini 200 (200 MHz), Varian Gemini 300 (300 MHz), Varian, AVANCE 300, Bruker BioSpin Corp.

In Reference Examples and Examples, purification by preparative HPLC was performed under the following conditions.
preparative HPLC tools: Gilson, Inc., high through-put purification system
column: YMC Combiprep ODS-A S-5 μm, 20×50 mm
solvent:
  Solution A; 0.1% trifluoroacetic acid-containing water,
  Solution B; 0.1% trifluoroacetic acid-containing acetonitrile
gradient cycle A: 0.00 min (Solution A/Solution B=90/10), 1.20 min (Solution A/Solution B=90/10), 4.75 min (Solution A/Solution B=0/100), 7.30 min (Solution A/Solution B=0/100) 7.40 min (Solution A/Solution B=90/10), 7.50 min (Solution A/Solution B=90/10).
gradient cycle B: 0.00 min (Solution A/Solution B=95/5), 1.00 min (Solution A/Solution B=95/5), 5.20 min (Solution A/Solution B=5/95), 6.40 min (Solution A/Solution B=5/95), 6.50 min (Solution A/Solution B=95/5), 6.60 min (Solution A/Solution B=95/5).

flow rate: 25 ml/min, detection method: UV 220 nm

In the present specification, the melting point (m.p.) refers to that measured using, for example, micromelting point measuring apparatus (Büchi, B-545) and the like.

In general, melting points vary depending on measurement apparatuses, measurement conditions and the like. The crystal in the present specification may show a different melting point from that described in the present specification, as long as it is within general error range.

Reference Example 1

2-(4-bromo-3-methylphenoxy)tetrahydro-2H-pyran

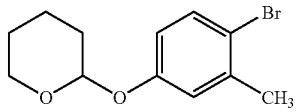

A solution of 4-bromo-3-methylphenol (4.72 g, 25.2 mmol), 3,4-dihydro-2H-pyran (3.18 g, 37.8 mmol) and pyridinium p-toluenesulfonate (0.628 g, 2.50 mmol) in dichloromethane (100 mL) was stirred at room temperature for 24 hrs. The reaction mixture was washed with water, and dried over anhydrous sodium sulfate. The solvent was evaporated under reduced pressure to give the title compound (7.11 g, including unreacted 3,4-dihydro-2H-pyran) as a yellow oil.

$^1$H NMR (CDCl$_3$) δ: 1.58-2.06(6H, m), 2.35(3H, s), 3.56-3.63(1H, m), 3.83-3.91(1H, m), 5.37(1H, t, J=3.1 Hz), 6.77 (1H, dd, J=8.8, 3.0 Hz), 6.95(1H, d, J=3.0 Hz), 7.39(1H, d, j=8.8 Hz).

Reference Example 2

2'-methyl-4'-(tetrahydro-2H-pyran-2-yloxy)biphenyl-3-carbaldehyde

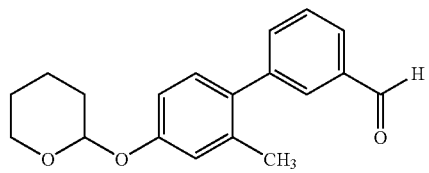

2-(4-Bromo-3-methylphenoxy)tetrahydro-2H-pyran (7.11 g, 25.2 mmol, including 3,4-dihydro-2H-pyran) and (3-formylphenyl)boronic acid (4.50 g, 30.0 mmol) were dissolved in a mixture of 1 M aqueous sodium carbonate solution (60 mL), ethanol (30 mL) and toluene (60 mL), and after argon substitution, tetrakis(triphenylphosphine)palladium(0) (1.73 g, 1.50 mmol) was added. The reaction mixture was stirred under an argon atmosphere at 80° C. for 15 hrs. The reaction mixture was cooled, water and ethyl acetate were added, and insoluble material was filtered off through celite. The organic layer of the filtrate was washed with saturated brine, dried over anhydrous sodium sulfate and concentrated under reduced pressure. The residue was purified by silica gel column chromatography (5%-30% ethyl acetate/hexane) to give the title compound (6.16 g, yield 82%, 2 steps) as a pale-yellow oil.

$^1$H NMR (CDCl$_3$) δ: 1.53-1.77(3H, m), 1.86-1.91(2H, m), 1.98-2.09(1H, m), 2.25(3H, s), 3.61-3.68(1H, m), 3.91-3.99 (1H, m), 5.48(1H, t, J=3.2 Hz), 6.95-7.00(2H, m), 7.15(1H, d, J=8.3 Hz), 7.53-7.60(2H, m), 7.82-7.86(2H, m), 10.06(1H, s).

Reference Example 3

[2'-methyl-4'-(tetrahydro-2H-pyran-2-yloxy)biphenyl-3-yl]methanol

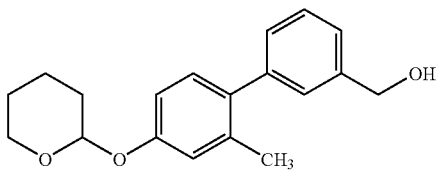

2'-Methyl-4'-(tetrahydro-2H-pyran-2-yloxy)biphenyl-3-carbaldehyde (13.6 g, 45.9 mmol) was dissolved in a mixture of 1,2-dimethoxyethane (70 mL) and tetrahydrofuran (70 mL), and sodium borohydride (0.870 g, 23.0 mmol) was added under ice-cooling. The mixture was stirred at the same temperature for 3 hrs. To the reaction mixture was added aqueous ammonium chloride solution, and the mixture was extracted with ethyl acetate. The extract was washed with saturated brine, dried over anhydrous sodium sulfate and concentrated under reduced pressure. The residue was purified by silica gel column chromatography (15%-50% ethyl acetate/hexane) to give the title compound (12.2 g, yield 89%) as a colorless oil.

$^1$H NMR (CDCl$_3$) δ: 1.59-1.76(4H, m), 1.85-1.90(2H, m), 1.97-2.11(1H, m), 2.25(3H, s), 3.60-3.67(1H, m), 3.91-3.99 (1H, m), 4.73(2H, d, J=5.8 Hz), 5.46(1H, t, J=3.1 Hz), 6.92-6.97(2H, m), 7.14(1H, d, J=8.1 Hz), 7.22-7.41(4H, m).

Reference Example 4

2-(4-bromo-3,5-dimethylphenoxy)tetrahydro-2H-pyran

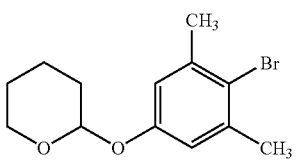

A solution of 4-bromo-3,5-dimethylphenol (10.5 g, 52.2 mmol), 3,4-dihydro-2H-pyran (8.83 g, 105 mmol) and pyridinium p-toluenesulfonate (2.64 g, 10.5 mmol) in dichloromethane (160 mL) was stirred at room temperature for 80 hrs. The solvent was evaporated under reduced pressure and the residue was purified by silica gel column chromatography (hexane-20% ethyl acetate/hexane) to give the title compound (11.5 g, yield 77%) as a colorless oil.

$^1$H NMR (CDCl$_3$) δ: 1.56-1.75(3H, m), 1.80-2.07(3H, m), 2.37(6H, s), 3.55-3.64(1H, m), 3.83-3.93(1H, m), 5.37(1H, t, J=3.1 Hz), 6.80(2H, s).

Reference Example 5

2',6'-dimethyl-4'-(tetrahydro-2H-pyran-2-yloxy)biphenyl-3-carbaldehyde

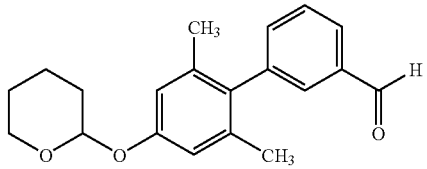

The title compound was obtained as a yellow oil from 2-(4-bromo-3,5-dimethylphenoxy)tetrahydro-2H-pyran and (3-formylphenyl)boronic acid according to a method similar to the method of Reference Example 2 (yield 83%).

$^1$H NMR (CDCl$_3$) δ: 1.57-1.78(3H, m), 1.82-1.93(2H, m), 1.99(6H, s), 2.04(1H, m), 3.65(1H, m), 3.97(1H, m), 5.47 (1H, t, J=3.0 Hz), 6.84(2H, s), 7.42(1H, m), 7.58(1H, t, J=7.5 Hz), 7.67(1H, s), 7.86(1H, m), 10.05(1H, s).

Reference Example 6

[2',6'-dimethyl-4'-(tetrahydro-2H-pyran-2-yloxy)biphenyl-3-yl]methanol

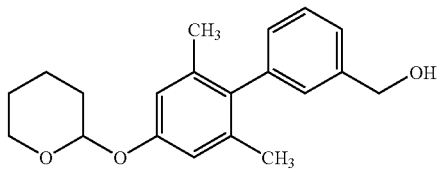

The title compound was obtained as a colorless oil from 2',6'-dimethyl-4'-(tetrahydro-2H-pyran-2-yloxy)biphenyl-3-carbaldehyde according to a method similar to the method of Reference Example 3 (yield 83%).

$^1$H NMR (CDCl$_3$) δ: 1.55-1.79(4H, m), 1.80-1.93(2H, m), 2.00(6H, s), 2.03(1H, m), 3.64(1H, m), 3.97(1H, m), 4.73 (2H, d, J=5.7 Hz), 5.45(1H, t, J=3.0 Hz), 6.81(2H,s), 7.07(1H, d, J=7.5 Hz), 7.13(1H, s), 7.33(1H, d, J=7.5 Hz), 7.40(1H, t, J=7.8 Hz).

Reference Example 7

2,6-dimethyl-3'-[(tetrahydro-2H-pyran-2-yloxy)methyl]biphenyl-4-ol

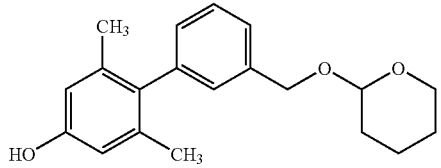

2',6'-Dimethyl-4'-(tetrahydro-2H-pyran-2-yloxy)biphenyl-3-carbaldehyde (9.05 g, 29.2 mmol) was dissolved in a mixture of 1,2-dimethoxyethane (50 mL) and tetrahydrofuran (50 mL), and sodium borohydride (0.567 g, 15.0 mmol) was added under ice-cooling. The mixture was stirred at the same temperature for 3 hrs. 10% Aqueous citric acid solution was added to the reaction mixture and the mixture was extracted with ethyl acetate. The extract was washed with saturated brine, dried over anhydrous sodium sulfate and concentrated under reduced pressure. The residue was purified by silica gel column chromatography (15%-50% ethyl acetate/hexane) to give the title compound (3.24 g, yield 36%) as colorless crystals.

$^1$H NMR (CDCl$_3$) δ: 1.47-1.93(6H, m), 1.98(3H, s), 1.99 (3H, s), 3.50-3.58(1H, m), 3.88-3.96(1H, m), 4.54(1H, d, J=12.1 Hz), 4.68(1H, s), 4.73(1H, t, J=3.4 Hz), 4.83(1H, d, J=12.1 Hz), 6.59(2H, s), 7.04(1H, d, J=7.3 Hz), 7.13(1H, s), 7.30-7.34(1H, m), 7.38(1H, t, J=7.3 Hz).

Reference Example 8

2-{[4'-(benzyloxy)-2',6'-dimethylbiphenyl-3-yl]methoxy}tetrahydro-2H-pyran

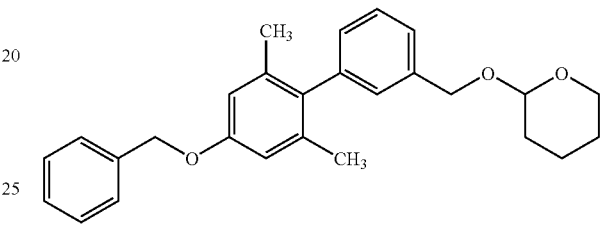

A solution of 2,6-dimethyl-3'-[(tetrahydro-2H-pyran-2-yloxy)methyl]biphenyl-4-ol (1.78 g, 5.70 mmol), benzyl alcohol (0.885 mL, 8.55 mmol) and tributylphosphine (2.13 mL, 8.55 mmol) in toluene (80 mL) was stirred under ice-cooling, and 1,1'-(azodicarbonyl)dipiperidine (2.16 g, 8.55 mmol) was added by small portions. The mixture was warmed to room temperature and stirred for 24 hrs. Hexane (40 mL) was added to the reaction mixture and the precipitated insoluble material was filtered off. The filtrate was concentrated under reduced pressure, and the residue was purified by silica gel column chromatography (hexane-10% ethyl acetate/hexane) to give the title compound as a colorless oil (1.71 g, yield 75%).

$^1$H NMR (CDCl$_3$) δ: 1.47-1.93(6H, m), 2.01(3H, s), 2.02 (3H, s), 3.50-3.57(1H, m), 3.88-3.96(1H, m), 4.54(1H, d, J=12.2 Hz), 4.73(1H, t, J=3.5 Hz), 4.83(1H, d, J=12.2 Hz), 5.07(2H, s), 6.75(2H, s), 7.05(1H, d, J=7.2 Hz), 7.14(1H, s), 7.30-7.48(7H, m).

Reference Example 9

[4'-(benzyloxy)-2',6'-dimethylbiphenyl-3-yl]methanol

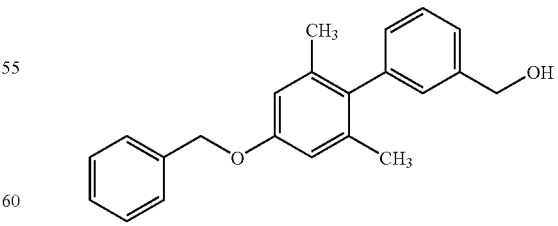

A solution of 2-{[4'-(benzyloxy)-2',6'-dimethylbiphenyl-3-yl]methoxy}tetrahydro-2H-pyran (1.71 g, 4.25 mmol) and p-toluenesulfonic acid monohydrate (80.8 mg, 0.425 mmol) in methanol (15 mL) was stirred at room temperature for 20 hrs. The reaction solvent was evaporated under reduced pressure and the residue was diluted with ethyl acetate, washed with saturated brine, dried over anhydrous magnesium sulfate and concentrated under reduced pressure. The residue was purified by silica gel column chromatography (20%-50% ethyl acetate/hexane) to give the title compound (1.13 g, yield 84%) as a colorless oil.

$^1$H NMR (CDCl$_3$) δ: 1.65(1H, t, J=5.9 Hz), 2.01(6H, s), 4.73(2H, d, J=5.9 Hz), 5.07(2H, s), 6.75(2H, s), 7.07(1H, d, J=7.3 Hz), 7.13(1H, s), 7.30-7.48(7H, m).

Reference Example 10

2-{[4'-(2-ethoxyethoxy)-2',6'-dimethylbiphenyl-3-yl]methoxy}tetrahydro-2H-pyran

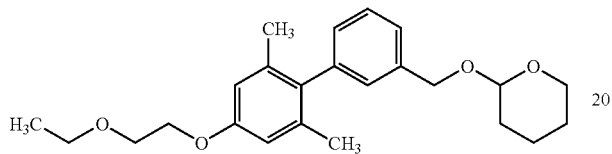

The title compound was obtained as a colorless oil from 2,6-dimethyl-3'-[(tetrahydro-2H-pyran-2-yloxy)methyl]biphenyl-4-ol and 2-ethoxyethanol according to a method similar to the method of Reference Example 8 (yield 74%).

$^1$H NMR (CDCl$_3$) δ: 1.25(3H, t, J=7.1 Hz), 1.48-1.94(6H, m), 2.00(3H, s), 2.01(3H, s), 3.50-3.57(1H, m), 3.62(2H, q, J=7.1 Hz), 3.80(2H, t, J=5.0 Hz), 3.88-3.96(1H, m), 4.14(2H, t, J=5.0 Hz), 4.54(1H, d, J=12.1 Hz), 4.72(1H, t, J=3.5 Hz), 4.82(1H, d, J=12.1 Hz), 6.69(2H, s), 7.04(1H, d, J=7.3 Hz), 7.13(1H, s), 7.32(1H, d, J=7.3 Hz), 7.38(1H, t, J=7.3 Hz).

Reference Example 11

[4'-(2-ethoxyethoxy)-2',6'-dimethylbiphenyl-3-yl]methanol

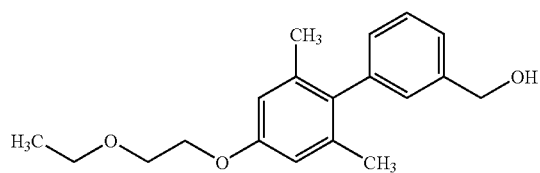

The title compound was obtained as a colorless oil from 2-{[4'-(2-ethoxyethoxy)-2',6'-dimethylbiphenyl-3-yl]methoxy}tetrahydro-2H-pyran according to a method similar to the method of Reference Example 9 (yield 82%).

MS m/z 301(MH$^+$)

Reference Example 12 ethyl (2E)-3-(2-fluoro-4-methoxyphenyl)acrylate

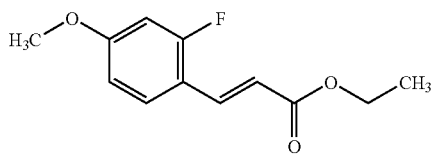

To an ice-cooled solution of ethyl diethylphosphonoacetate (9.45 g, 42.1 mmol) in tetrahydrofuran (50 mL) was added sodium hydride (60% oil suspension, 1.54 g, 38.5 mmol) and the mixture was stirred for 15 min. A solution of 2-fluoro-4-methoxybenzaldehyde (5.00 g, 32.4 mmol) in tetrahydrofuran (30 mL) was added dropwise. The mixture was stirred at room temperature for 2 hrs. and water was added. The mixture was extracted with ethyl acetate. The extract was washed with saturated brine, dried over anhydrous magnesium sulfate and concentrated under reduced pressure. The residue was purified by silica gel column chromatography (20% ethyl acetate/hexane) to give the title compound (7.07 g, yield 97%) as a colorless oil.

$^1$H NMR (CDCl$_3$) δ: 1.33(3H, t, J=7.1 Hz), 3.83(3H, s), 4.26(2H, q, J=7.1 Hz), 6.41(1H, d, J=16.2 Hz), 6.61-6.73(2H, m), 7.45(1H, t, J=8.6 Hz), 7.75(1H, d, J=16.2 Hz).

Reference Example 13 ethyl 3-(2-fluoro-4-methoxyphenyl)propanoate

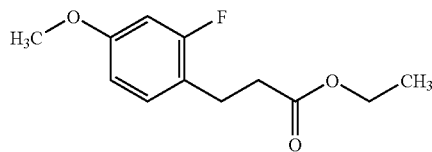

A mixture of ethyl (2E)-3-(2-fluoro-4-methoxyphenyl)acrylate (7.07 g, 31.5 mmol), tetrahydrofuran (50 mL), ethanol (5 mL) and platinum oxide (300 mg) was stirred overnight under a hydrogen atmosphere at room temperature. The catalyst was filtered off and the filtrate was concentrated. The residue was purified by silica gel column chromatography (20% ethyl acetate/hexane) to give the title compound (5.97 g, yield 84%) as a colorless oil.

$^1$H NMR (CDCl$_3$) δ: 1.23(3H, t, J=7.2 Hz), 2.58(2H, t, J=7.6 Hz), 2.90(2H, t, J=7.6 Hz), 3.77(3H, s), 4.12(2H, q, J=7.2 Hz), 6.57-6.63(2H, m), 7.07-7.13(1H, m).

Reference Example 14 ethyl 3-(2-fluoro-4-hydroxyphenyl)propanoate

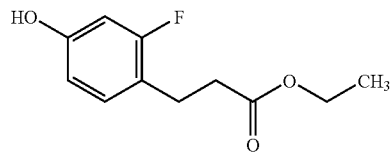

To a solution of ethyl 3-(2-fluoro-4-methoxyphenyl)propanoate (57.4 g, 254 mmol) and aluminum chloride (101 g, 761 mmol) in dichloromethane (250 mL) was added dropwise 1-octanethiol (74.3 g, 508 mmol) and the mixture was stirred at room temperature for 2 hrs. The reaction mixture was poured into ice water and the mixture was stirred for 30 min. The organic layer was separated, washed with saturated brine, dried over anhydrous magnesium sulfate and concentrated under reduced pressure. The residue was purified by silica gel column chromatography (20% ethyl acetate/hexane) to give the title compound (44.6 g, yield 83%) as a colorless oil.

$^1$H NMR (CDCl$_3$) δ: 1.23(3H, t, J=7.2 Hz), 2.58(2H, t, J=8.1 Hz), 2.89(2H, t, J=8.1 Hz), 4.12(2H, q, J=7.2 Hz), 6.51-6.56(2H, m), 7.01-7.06(1H, m).

Reference Example 15 ethyl 2',4'-dimethylbiphenyl-3-carboxylate

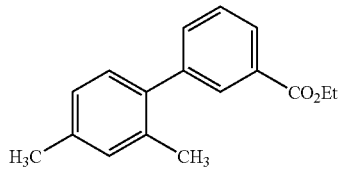

(2,4-Dimethylphenyl)boronic acid (3.0 g, 20.0 mmol), ethyl 3-bromobenzoate (4.3 g, 18.8 mmol) and cesium carbonate (9.8 g, 30.0 mmol) were added to a mixture of ethanol (20 mL) and toluene (80 mL), and after argon substitution, tetrakis(triphenylphosphine)palladium(0) (0.30 g, 0.26 mmol) was added. The reaction mixture was stirred under an argon atmosphere at 70° C. for 18 hrs. The reaction mixture was cooled and insoluble material was filtered off through celite. The filtrate was concentrated under reduced pressure and the residue was purified by silica gel column chromatography (ethyl acetate:hexane=1:10) to give the title compound (5.0 g, yield 100%) as a colorless oil.
$^1$H NMR (CDCl$_3$) δ: 1.39(3H, t, J=7.0 Hz), 2.23(3H, s), 2.37(3H, s), 4.38(2H, q, J=7.0 Hz), 7.02-7.54(5H, m), 8.00-8.05(2H, m).

Reference Example 16

(2',4'-dimethylbiphenyl-3-yl)methanol

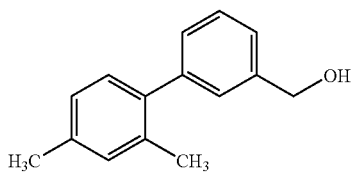

To a solution of ethyl 2',4'-dimethylbiphenyl-3-carboxylate (5.0 g, 19.7 mmol) in anhydrous tetrahydrofuran (50 mL) was added lithium aluminum hydride (0.91 g, 24.0 mmol) under ice-cooling and the mixture was stirred at room temperature for 3 hrs. The reaction solution was ice-cooled and sodium sulfate 10 hydrate (8.0 g, 24.8 mmol) was added. The mixture was stirred at room temperature for 1 hr. The precipitated insoluble material was filtered off through celite, and the filtrate was concentrated under reduced pressure to give the title compound as a colorless oil (yield 96%).
$^1$H NMR (CDCl$_3$) δ: 2.24(3H, s), 2.36(3H, s), 4.73(2H, d, J=6.0 Hz), 7.00-7.45(7H, m).

Reference Example 17

2',4',6'-trimethylbiphenyl-3-carbaldehyde

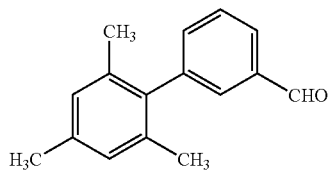

The title compound was obtained as a colorless oil from (2,4,6-trimethylphenyl)boronic acid and 3-bromobenzaldehyde according to a method similar to the method of Reference Example 15 (yield 76%).
MS m/z 225(MH$^+$)

Reference Example 18

(2',4',6'-trimethylbiphenyl-3-yl)methanol

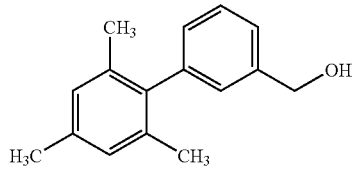

2',4',6'-Trimethylbiphenyl-3-carbaldehyde (2.36 g, 10.5 mmol) was dissolved in ethanol (20 mL), and sodium borohydride (0.40 g, 10.6 mmol) was added to the solution. After stirring under ice-cooling for 3 hrs., aqueous citric acid solution was added to the reaction solution. The mixture was extracted with ethyl acetate, washed with saturated brine, dried over magnesium sulfate, and concentrated under reduced pressure. The obtained residue was purified by silica gel column chromatography (ethyl acetate:hexane=1:5-1:2) to give the title compound (1.66 g, yield 70%) as a colorless oil.
$^1$H NMR (CDCl$_3$) δ: 2.00(6H, s), 2.33(3H, s), 4.73(2H, d, J=6.2 Hz), 6.94(2H, s), 7.00-7.42(4H, m).

Reference Example 19

6-methoxy-2',4'-dimethylbiphenyl-3-carbaldehyde

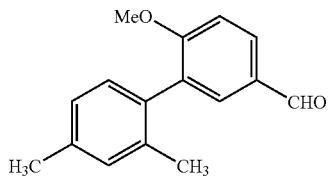

The title compound was obtained as a colorless oil from 1-bromo-2,4-dimethylbenzene and (5-formyl-2-methoxyphenyl)boronic acid according to a method similar to the method of Reference
Example 15 (yield 87%).
MS m/z 241(MH$^+$)

Reference Example 20

(6-methoxy-2',4'-dimethylbiphenyl-3-yl)methanol

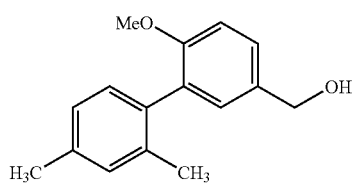

The title compound was obtained as a colorless oil from 6-methoxy-2',4'-dimethylbiphenyl-3-carbaldehyde according to a method similar to the method of Reference Example 18 (yield 88%).

¹H NMR (CDCl₃) δ: 2.01(6H, s), 3.74(3H, s), 4.65(2H, d, J=5.2 Hz), 6.97(1H, d, J=8.4 Hz), 7.03(1H, d, J=2.2 Hz), 7.06-7.24(3H, m), 7.35(1H, dd, J=2.6, 8.4 Hz).

Reference Example 21 ethyl 2',4',6'-trimethylbiphenyl-3-carboxylate

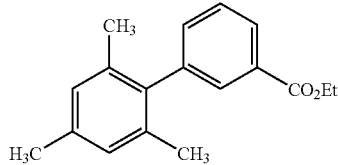

The title compound was obtained as a colorless oil from (2,4,6-trimethylphenyl)boronic acid and ethyl 3-bromobenzoate according to a method similar to the method of Reference Example 15 (yield 80%).

MS m/z 269(MH⁺)

Reference Example 22 ethyl 4'-bromomethyl-2',6'-dimethylbiphenyl-3-carboxylate and ethyl 2'-bromomethyl-4',6'-dimethylbiphenyl-3-carboxylate Mixture of

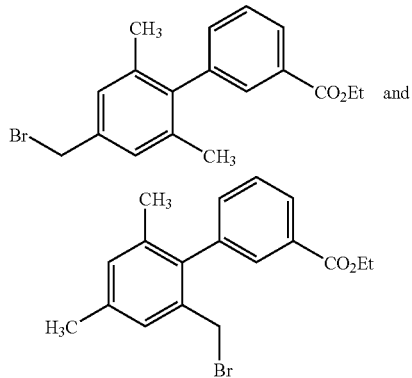

A solution of ethyl 2',4',6'-trimethylbiphenyl-3-carboxylate (1.0 g, 3.73 mmol), N-bromosuccinimide (0.70 g, 3.93 mmol) and 2,2'-azobis(isobutyronitrile) (65 mg, 0.40 mmol) in carbon tetrachloride (30 mL) was stirred at 80° C. for 5 hrs. The reaction solution was cooled to room temperature, and the precipitated insoluble material was filtered off. The filtrate was concentrated under reduced pressure, and the obtained residue was purified by silica gel column chromatography (ethyl acetate:hexane=1:10-1:5) to give a mixture (0.82 g, yield 64%) of the title compounds as a colorless oil. The mixture was used for the next reaction without separation.

MS m/z 348(MH⁺)

Reference Example 23

[4'-[(4-fluorophenoxy)methyl]-2',6'-dimethylbiphenyl-3-yl]methanol and [2'-[(4-fluorophenoxy)methyl]-4',6'-dimethylbiphenyl-3-yl]methanol Mixture of

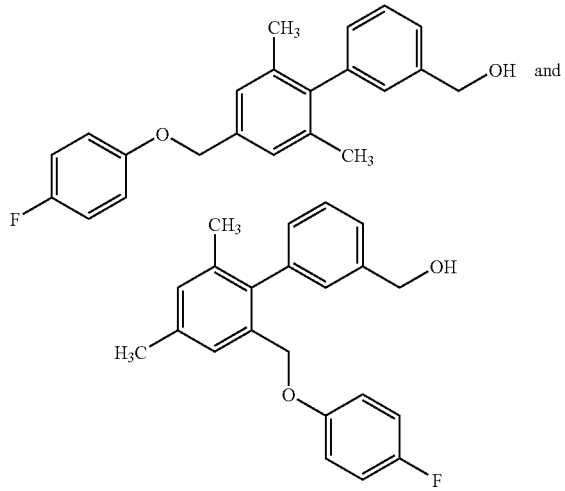

A mixed solution of p-fluorophenol (0.32 g, 2.85 mmol) and sodium hydride (89 mg, 2.60 mmol) in anhydrous tetrahydrofuran (20 mL)-N,N-dimethylformamide (10 mL) was stirred under ice-cooling for 20 min. To the solution was added the mixture (0.82 g, 2.36 mmol) obtained in Reference Example 22 and the mixture was stirred at room temperature for 18 hrs. The reaction solution was diluted with ethyl acetate, washed successively with aqueous citric acid solution, water and saturated brine, dried over magnesium sulfate, and concentrated under reduced pressure. The obtained pale-yellow oil was dissolved in anhydrous tetrahydrofuran (30 mL) and the mixture was ice-cooled. To the solution was added dropwise 1.5 mol/l diisobutylaluminum hydride toluene solution (5.0 mL, 7.5 mmol). The solution was stirred under ice-cooling for 5 hrs. and dilute hydrochloric acid was added to the reaction solution. The mixture was extracted with ethyl acetate, washed with saturated brine, dried over magnesium sulfate, and concentrated under reduced pressure. The obtained residue was purified by silica gel column chromatography (ethyl acetate:hexane=1:10-1:5-1:3-1:1) to give a mixture (0.74 g, yield 93%) of the title compounds as a colorless oil. The mixture was used for the next reaction without separation.

MS m/z 319(M–OH)

Reference Example 24 methyl 3-[4-[(3-bromobenzyl)oxy]phenyl]propanoate

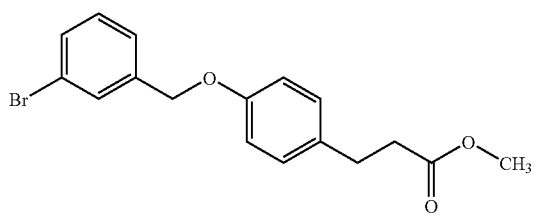

To a solution of methyl 3-(4-hydroxyphenyl)propanoate (0.3 g, 1.67 mmol) in N,N-dimethylformamide (4.0 mL) was added 60% sodium hydride (0.073 g, 1.83 mmol) at 0° C. with stirring, and the mixture was stirred at the same temperature for 15 min. Then, 3-bromobenzylbromide (0.44 g, 1.75 mmol) was added to the mixture at 0° C. with stirring, and the mixture was stirred at room temperature for 2 hrs. The reaction mixture was diluted with ethyl acetate and washed with 5% aqueous potassium hydrogensulfate solution and saturated brine. The ethyl acetate layer was dried over magnesium sulfate and concentrated under reduced pressure to give the title compound (0.84 g, yield 72%) as a colorless powder.

$^1$H NMR (CDCl$_3$) δ: 2.60(2H, t, J=7.8 Hz), 2.90(2H, t, J=7.8 Hz), 3.67(3H, s), 5.01(2H, s), 6.88(2H, d, J=8.4 Hz), 7.12(2H, d, J=8.4 Hz), 7.25(1H, m), 7.35(1H, d, J=7.5 Hz), 7.45(1H, d, J=7.5 Hz), 7.59(1H, s).

Reference Example 25

4'-(methoxymethoxy)-2',6'-dimethylbiphenyl-3-carbaldehyde

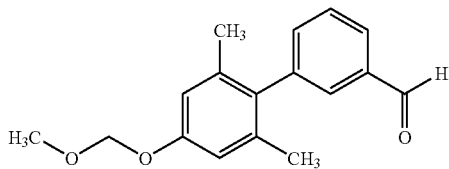

A mixture of 4'-hydroxy-2',6'-dimethylbiphenyl-3-carbaldehyde (4.5 g, 19.9 mmol), chloromethyl methyl ether (2.3 mL, 30.3 mmol), potassium carbonate (5.5 g, 39.8 mmol) and potassium iodide (0.66 g, 3.98 mmol) in N,N-dimethylformamide (50 mL) was stirred at 70° C. for 20 hrs. The reaction solution was diluted with ethyl acetate, washed successively with aqueous citric acid solution, water and saturated brine, dried over magnesium sulfate, and concentrated under reduced pressure. The obtained residue was purified by silica gel column chromatography (ethyl acetate:hexane=3:97-1:9) to give the title compound (1.7 g, yield 32%) as a colorless oil.

MS m/z 271 (MH+)

Reference Example 26

[4'-(methoxymethoxy)-2',6'-dimethylbiphenyl-3-yl]methanol

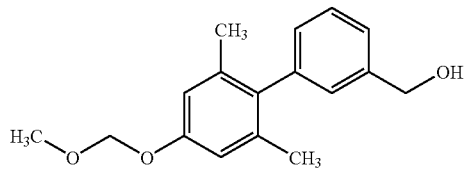

The title compound was obtained as a colorless oil from 4'-(methoxymethoxy)-2',6'-dimethylbiphenyl-3-carbaldehyde according to a method similar to the method of Reference Example 3 (yield 89%).

MS m/z 255 (MH+)

Reference Example 27 ethyl 2,2-difluoro-3-(4-hydroxyphenyl)propanoate

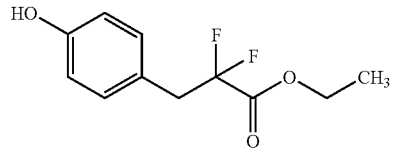

To a solution of ethyl 2,2-difluoro-3-(4-methoxyphenyl)propanoate (1.72 g, 7.05 mmol) synthesized according to the method described in Synthesis, vol. 13, pp. 1917-1924 (2000) and aluminum chloride (2.82 g, 21.2 mmol) in dichloromethane (50 mL) was added dropwise 1-octanethiol (2.06 g, 14.1 mmol) and the mixture was stirred at room temperature for 2 hrs. The reaction mixture was poured into ice water and the mixture was stirred for 30 min. The organic layer was separated, washed with saturated brine, dried over anhydrous magnesium sulfate and concentrated under reduced pressure. The residue was purified by silica gel column chromatography (8%-60% ethyl acetate/hexane) to give the title compound (0.90 g, yield 56%) as a colorless oil.

$^1$H NMR (CDCl$_3$) δ: 1.26(3H, t, J=7.1 Hz), 3.30(2H, t, J=16.3 Hz), 4.25(2H, q, J=7.2 Hz), 4.84(1H, s), 6.74-6.82 (2H, m), 7.13(2H, d, J=8.3 Hz).

Reference Example 28

2-(4-bromo-3,5-dimethylphenoxy)-6-methylpyridine

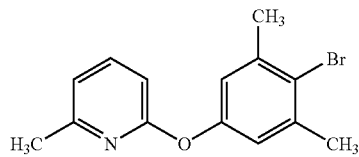

To a solution of sodium hydroxide (0.23 g, 5.81 mmol) in methanol (50 mL) was added 4-bromo-3,5-dimethylphenol (1.17 g, 5.81 mmol) and the mixture was left standing at room temperature for 10 min. and concentrated to dryness to give 4-bromo-3,5-dimethylphenol sodium salt (1.30 g). Then, a mixture of the obtained 4-bromo-3,5-dimethylphenol sodium salt (1.30 g), 2-bromo-6-methylpyridine (1.0 g, 5.81 mmol) and copper powder (11 mg, 0.17 mmol) was stirred at 185° C. for 1 hr. The reaction mixture was cooled, diluted with ethyl acetate, washed with water and saturated brine, dried and concentrated under reduced pressure. The residue was purified by silica gel column chromatography (hexane-hexane/ethyl acetate=5/1) to give the title compound (1.25 g, yield 74%) as a pale-yellow oil.

MS (ESI+): 292 (M+H), 294

Reference Example 29

2',6'-dimethyl-4'-[(6-methylpyridin-2-yl)oxy]biphenyl-3-carbaldehyde

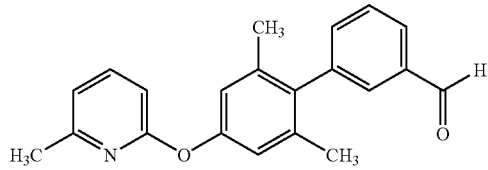

The title compound was obtained as a colorless oil from 2-(4-bromo-3,5-dimethylphenoxy)-6-methylpyridine and (3-formylphenyl)boronic acid according to a method similar to the method of Reference Example 2 (yield 94%).

MS (ESI+): 318 (M+H)

Reference Example 30

{2',6'-dimethyl-4'-[(6-methylpyridin-2-yl)oxy]biphenyl-3-yl}methanol

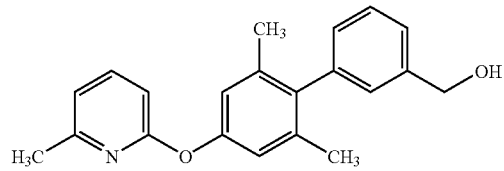

The title compound was obtained as a colorless oil from 2',6'-dimethyl-4'-[(6-methylpyridin-2-yl)oxy]biphenyl-3-carbaldehyde according to a method similar to the method of Reference Example 3 (yield 98%).

MS(ESI+): 320 (M+H)

Reference Example 31

2-bromo-5-(2-ethoxyethoxy)-1,3-dimethylbenzene

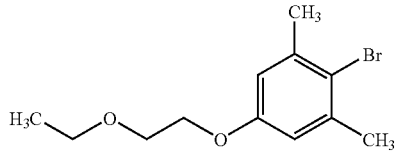

To a solution of 4-bromo-3,5-dimethylphenol (12 g, 59.7 mmol), potassium iodide (1.5 g, 9.0 mmol) and potassium carbonate (9.9 g, 71.6 mmol) in N,N-dimethylformamide (80 mL) was added 2-chloroethyl ethyl ether (9.7 g, 89.3 mmol) at room temperature with stirring and the mixture was stirred at 70° C. for 2 days. The reaction mixture was cooled and concentrated under reduced pressure. The residue was partitioned between ethyl acetate and water. The organic layer was washed with saturated brine, dried over magnesium sulfate, and concentrated under reduced pressure. The residue was purified by silica gel column chromatography (hexane/ethyl acetate=19/1) to give the title compound (15.9 g, yield 98%) as a yellow oil.

MS (ESI+): 274 (M+H)

Reference Example 32

[4-(2-ethoxyethoxy)-2,6-dimethylphenyl]boronic acid

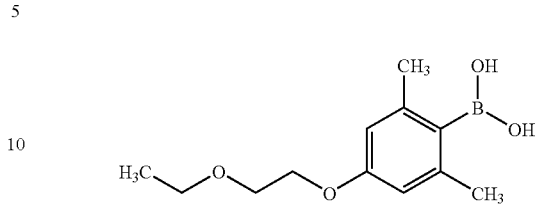

To a solution of 2-bromo-5-(2-ethoxyethoxy)-1,3-dimethylbenzene (10.0 g, 36.6 mmol) in tetrahydrofuran (100 mL) was added n-butyllithium hexane solution (1.6 M, 25.1 mL, 40.2 mmol) at −78° C. with stirring. The reaction mixture was stirred at the same temperature for 30 min. and triisopropyl borate (10.5 mL, 45.5 mmol) was added. The reaction mixture was warmed to room temperature and stirred for 3 hrs. 5 N Hydrochloric acid (20 mL) was added to the reaction mixture and the mixture was partitioned between ethyl acetate and water. The organic layer was dried over magnesium sulfate and concentrated under reduced pressure. The residue was washed with hexane/diethyl ether and dried to give the title compound (5.9 g, yield 68%) as pale-yellow crystals.

$^1$H NMR (CDCl$_3$) δ: 1.24 (3H, t, J=7.0 Hz), 2.36 (6H, s), 3.60 (2H, q, J=7.0 Hz), 3.77 (2H, t, J=5.0 Hz), 4.09 (2H, t, J=5.0 Hz), 4.52 (2H, s), 6.58 (2H, s).

Reference Example 33 methyl 4'-(2-ethoxyethoxy)-6-methoxy-2',6'-dimethylbiphenyl-3-carboxylate

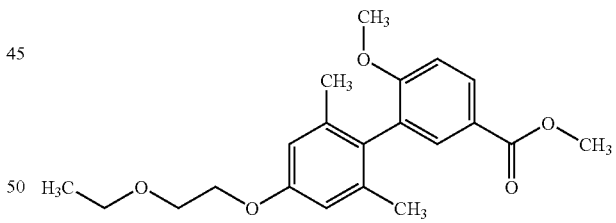

A mixture of methyl 3-bromo-4-methoxybenzoate (0.90 g, 3.67 mmol), [4-(2-ethoxyethoxy)-2,6-dimethylphenyl]boronic acid (0.87 g, 3.67 mmol), tris(dibenzylideneacetone)dipalladium(0) (0.13 g, 0.15 mmol), 2-(dicyclohexylphosphino)biphenyl (79 mg, 0.22 mmol), tripotassium phosphate (1.56 g, 7.34 mmol) and toluene (20 mL) was stirred under a nitrogen atmosphere at 90° C. for 18 hrs. The reaction mixture was cooled and insoluble material was filtered off. The filtrate was concentrated under reduced pressure and the residue was purified by silica gel column chromatography (hexane/ethyl acetate=9/1-hexane/ethyl acetate=1/1) to give the title compound (0.71 g, yield 54%) as a yellow oil.

MS (ESI+): 359 (M+H)

Reference Example 34

[4'-(2-ethoxyethoxy)-6-methoxy-2',6'-dimethylbiphenyl-3-yl]methanol

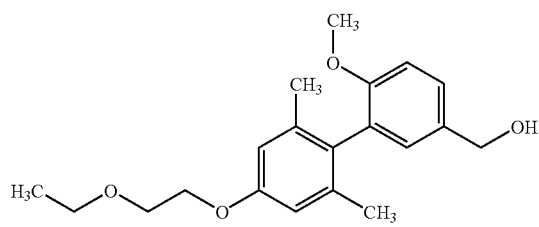

The title compound was obtained as a colorless oil from methyl 4'-(2-ethoxyethoxy)-6-methoxy-2',6'-dimethylbiphenyl-3-carboxylate according to a method similar to the method of Reference Example 16 (yield 100%).

MS(ESI+):331 (M+H)

Reference Example 35

4'-hydroxy-2',6'-dimethylbiphenyl-3-carbaldehyde

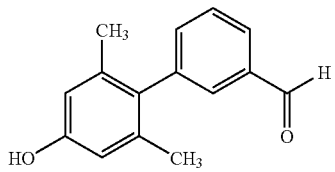

The title compound was obtained as pale-yellow crystals from 4-bromo-3,5-dimethylphenol and (3-formylphenyl)boronic acid according to a method similar to the method of Reference Example 2 (yield 83%).

MS (ESI+): 227 (M+H)

Reference Example 36

4'-{[tert-butyl(dimethyl)silyl]oxy}-2',6'-dimethylbiphenyl-3-carbaldehyde

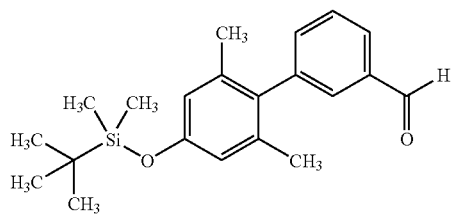

To a solution of 4'-hydroxy-2',6'-dimethylbiphenyl-3-carbaldehyde (9.0 g, 39.8 mmol) and imidazole (2.98 g, 43.8 mmol) in N,N-dimethylformamide (100 mL) was added tert-butyldimethylchlorosilane (6.6 g, 43.8 mmol) at room temperature with stirring, and the mixture was stirred at room temperature for 4 hrs. The reaction mixture was diluted with ethyl acetate, washed with water and saturated brine, dried and concentrated under reduced pressure. The residue was purified by silica gel column chromatography (hexane/ethyl acetate=10/1-hexane/ethyl acetate=4/1) to give the title compound (10.5 g, yield 77%) as a yellow oil.

$^1$H NMR (CDCl$_3$) δ: 0.25 (6H, s), 1.02 (9H, s), 1.97 (6H, s), 6.62 (2H, s), 7.44 (1H, dt, J=1.5, 7.5 Hz), 7.59 (1H, t, J=7.5 Hz), 7.68 (1H, t, J=1.5 Hz), 7.86 (1H, dt, J=1.5, 7.5 Hz), 10.06 (1H, s).

Reference Example 37

(4'-{[tert-butyl(dimethyl)silyl]oxy}-2',6'-dimethylbiphenyl-3-yl)methanol

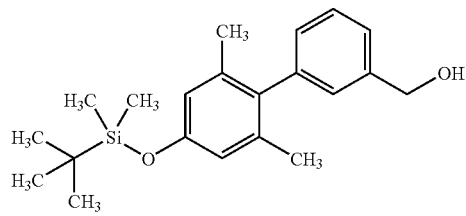

The title compound was obtained as colorless crystals from 4'-{[tert-butyl(dimethyl)silyl]oxy}-2',6'-dimethylbiphenyl-3-carbaldehyde according to a method similar to the method of Reference Example 3 (yield 89%).

$^1$H NMR (CDCl$_3$) δ: 0.23 (6H, s), 1.00 (9H, s), 1.96 (6H, s), 4.73 (2H, s), 6.58 (2H, s), 7.07 (1H, d, J=7.5 Hz), 7.13 (1H, s), 7.32 (1H, d, J=7.5 Hz), 7.40 (1H, t, J=7.5 Hz).

Reference Example 38 tert-butyl (2E)-3-[4-(benzyloxy)phenyl]acrylate

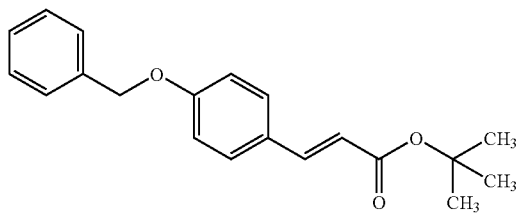

The title compound was obtained as colorless crystals from 4-(benzyloxy)benzaldehyde and tert-butyl diethylphosphonoacetate according to a method similar to the method of Reference Example 12 (yield 94%).

$^1$H NMR (CDCl$_3$) δ: 1.53 (9H, s), 5.09 (2H, s), 6.24 (1H, d, J=15.9 Hz), 6.96 (2H, d, J=9.0 Hz), 7.32-7.49 (7H, m), 7.54 (1H, d, J=15.9 Hz).

Reference Example 39 tert-butyl 3-(4-hydroxyphenyl)propanoate

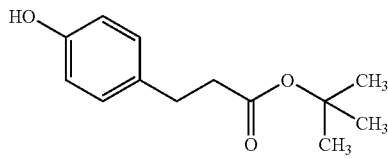

A mixture of tert-butyl (2E)-3-[4-(benzyloxy)phenyl]acrylate (13.3 g, 42.8 mmol), 10% palladium carbon (1.3 g), ethanol (100 mL) and ethyl acetate (30 mL) was stirred under a hydrogen atmosphere at room temperature for 19 hrs. The catalyst was filtered off and the filtrate was concentrated under reduced pressure to give the title compound (7.5 g, yield 79%) as colorless crystals.

¹H NMR (CDCl₃) δ: 1.41 (9H, s), 2.50 (2H, t, J=7.8 Hz), 2.83 (2H, t, J=7.8 Hz), 6.74 (2H, d, J=8.7 Hz), 7.06 (2H, d, J=8.7 Hz).

Reference Example 40

2,6-dimethyl-4-nitrophenyl trifluoromethanesulfonate

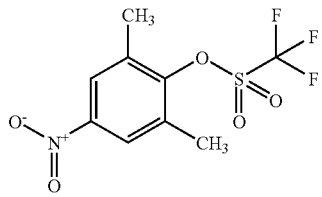

To a solution of 2,6-dimethyl-4-nitrophenol (5.0 g, 29.9 mmol) in N,N-dimethylformamide (50 mL) was added sodium hydride (60%, 1.44 g, 35.9 mmol) at 0° C. with stirring and the mixture was stirred for 10 min. N-phenylbis(trifluoromethanesulfonimide) (12.8 g, 35.9 mmol) was added and the mixture was stirred at the same temperature for 2 hrs. The reaction mixture was diluted with ethyl acetate, washed with water and saturated brine, dried and concentrated under reduced pressure. The residue was purified by silica gel column chromatography (hexane/ethyl acetate=10/1-hexane/ethyl acetate=5/1) to give the title compound (9.2 g, yield 100%) as a yellow oil.

¹H NMR (CDCl₃) δ: 2.50 (6H, s), 8.03 (2H, s).

Reference Example 41

(2',6'-dimethyl-4'-nitrobiphenyl-3-yl)methanol

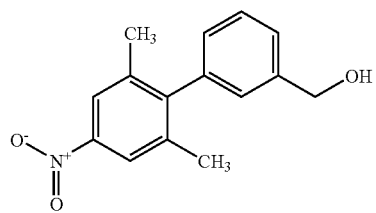

A mixture of 2,6-dimethyl-4-nitrophenyl trifluoromethanesulfonate (9.2 g, 29.9 mmol), 3-(formylphenyl)boronic acid (4.7 g, 31.4 mmol), tris(dibenzylideneacetone)dipalladium(0) (1.10 g, 1.20 mmol), rac-2,2'-bis(diphenylphosphino)-1,1'-binaphthyl (1.12 g, 1.80 mmol), cesium carbonate (14.6 g, 44.9 mmol) and toluene (150 mL) was stirred under a nitrogen atmosphere at 90° C. for 18 hrs. The reaction mixture was cooled and the insoluble material was filtered off. The filtrate was concentrated under reduced pressure and the residue was purified by silica gel column chromatography (hexane/ethyl acetate=9/1-hexane/ethyl acetate=2/1) to give a yellow oil (1.0 g). To a mixture of the obtained yellow oil (1.0 g), methanol (10 mL) and tetrahydrofuran (10 mL) was added sodium borohydride (74 mg, 1.96 mmol) at 0° C. with stirring and the mixture was stirred at the same temperature for 2 hrs. Water and ethyl acetate were added to the reaction mixture to partition the mixture. The organic layer was dried over magnesium sulfate and concentrated under reduced pressure. The residue was purified by silica gel column chromatography (hexane/ethyl acetate=4/1-hexane/ethyl acetate=1/1) to give the title compound (0.44 g, yield 6%) as pale-yellow crystals.

¹H NMR (CDCl₃) δ: 1.74 (1H, t, J=5.7 Hz), 2.11(6H, s), 4.77 (2H, d, J=5.7 Hz), 7.04 (1H, m), 7.12 (1H, s), 7.41 (1H, d, J=7.8 Hz), 7.48 (1H, t, J=7.5 Hz), 7.97 (2H, s).

Reference Example 42

1-oxa-6-thiaspiro[2.5]octane

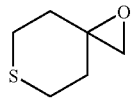

To a suspension of trimethylsulfoxonium iodide (37.1 g, 165.1 mmol) in dimethyl sulfoxide (120 mL) was slowly added sodium hydride (6.10 g, 152.4 mmol) under a nitrogen atmosphere at room temperature, and after stirring for 1 hr., a solution of tetrahydro-4H-thiopyran-4-one (14.8 g, 127.0 mmol) in dimethyl sulfoxide (60 mL) was added dropwise over 20 min. The reaction solution was further stirred at room temperature for 14 hrs., diluted with water and extracted with diethyl ether. The organic layer was washed with water and saturated brine, dried over anhydrous sodium sulfate and concentrated under reduced pressure. The residue was stood at room temperature and the obtained crystals were washed with a small amount of hexane and dried to give the title compound (8.22 g, yield 50%) as colorless needle crystals.

¹H NMR (CDCl₃) δ: 1.69-1.82(2H, m), 1.93-2.09(2H, m), 2.56-2.73(4H, m), 2.85-3.01(2H, m).

Reference Example 43

4'-[(4-hydroxytetrahydro-2H-thiopyran-4-yl)methoxy]-2',6'-dimethylbiphenyl-3-carbaldehyde

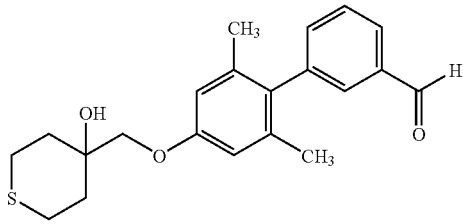

To a solution of 1-oxa-6-thiaspiro[2.5]octane (6.33 g, 48.6 mmol) and 4'-hydroxy-2',6'-dimethylbiphenyl-3-carbaldehyde (10.0 g, 44.2 mmol) in N,N-dimethylformamide (150 mL) was added potassium carbonate (6.11 g, 44.2 mmol) at room temperature with stirring and the mixture was stirred at 100° C. for 12 hrs. The reaction mixture was concentrated under reduced pressure. To the residue was added 1 M hydrochloric acid to neutralize the solution and the mixture was extracted with ethyl acetate. The extract was dried over anhydrous sodium sulfate, concentrated under reduced pressure and crystallized by adding diisopropyl ether to the obtained oil. The crystals were collected by filtration to give the title compound (12.3 g, yield 78%) as colorless crystals.

¹H NMR (CDCl₃) δ: 1.76-1.91(2H, m), 2.00(6H, s), 2.06-2.17(2H, m), 2.19(1H, s), 2.41-2.55(2H, m), 3.03-3.19(2H, m), 3.81(2H, s), 6.69(2H, s), 7.37-7.46(1H, m), 7.55-7.71 (2H, m), 7.83-7.92(1H, m), 10.05(1H, s).

Reference Example 44

4-({[3'-(hydroxymethyl)-2,6-dimethylbiphenyl-4-yl]oxy}methyl)tetrahydro-2H-thiopyran-4-ol

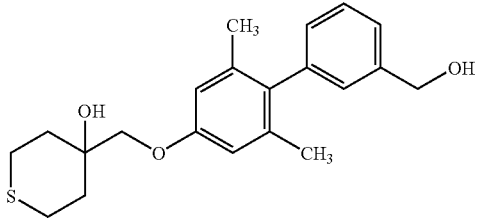

The title compound was obtained as colorless crystals from 4'-[(4-hydroxytetrahydro-2H-thiopyran-4-yl)methoxy]-2',6'-dimethylbiphenyl-3-carbaldehyde according to a method similar to the method of Reference Example 3 (yield 100%).

$^1$H NMR (CDCl$_3$) δ: 1.70(1H, t, J=5.8 Hz), 1.76-1.90(2H, m), 2.01(6H, s), 2.05-2.16(2H, m), 2.20(1H, s), 2.40-2.53 (2H, m), 3.03-3.18(2H, m), 3.80(2H, s), 4.73(2H, d, J=5.8 Hz), 6.67(2H, s), 7.02-7.09(1H, m), 7.12(1H, s), 7.31-7.37 (1H, m), 7.41(1H, t, J=7.4 Hz).

Reference Example 45 methyl 3-bromo-4-hydroxybenzoate

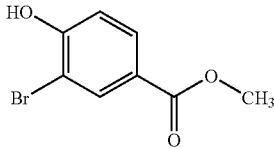

A solution of 3-bromo-4-hydroxybenzoic acid (50.4 g, 232 mmol) and conc. sulfuric acid (17 mL) in methanol (330 mL) was heated under reflux for 24 hrs. The reaction mixture was neutralized with aqueous sodium hydroxide solution. Methanol was removed under reduced pressure and the residue was extracted with ethyl acetate. The extract was washed with aqueous sodium hydrogen carbonate and saturated brine, dried over anhydrous sodium sulfate and concentrated under reduced pressure. The obtained crystals were washed with diethyl ether/hexane to give the title compound (45.5 g, yield 85%) as pale-pink crystals.

MS m/z 231 (MH$^+$)

Reference Example 46 methyl 3-bromo-4-isopropoxybenzoate

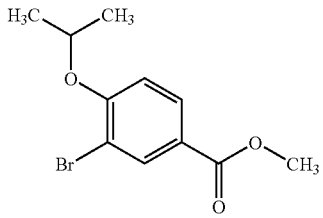

To a solution of methyl 3-bromo-4-hydroxybenzoate (15.0 g, 64.9 mmol), 2-bromopropane (7.68 mL, 77.9 mmol) and potassium iodide (1.0 g, 6.49 mmol) in N,N-dimethylformamide (200 mL) was added potassium carbonate (13.5 g, 97.4 mmol) and the mixture was stirred at 80° C. for 2 hrs. The reaction mixture was concentrated under reduced pressure. Brine was added to the obtained residue and the mixture was extracted with ethyl acetate. The extract was dried over anhydrous sodium sulfate and concentrated under reduced pressure. The residue was purified by silica gel chromatography (hexane-hexane/ethyl acetate=9/1) to give the title compound (14.6 g, yield 83%) as a colorless oil.

$^1$H NMR (CDCl$_3$) δ: 1.41(6H, d, J=6.0 Hz), 3.89(3H, s), 4.59-4.75(1H, m), 6.90(1H, d, J=8.9 Hz), 7.94(1H, dd, J=8.7, 2.1 Hz), 8.23(1H, d, J=2.1 Hz).

Reference Example 47

(4-bromo-3,5-dimethylphenoxy)(tert-butyl)dimethylsilane

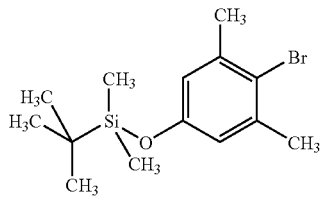

The title compound was obtained as a colorless oil from 4-bromo-3,5-dimethylphenol according to a method similar to the method of Reference Example 36 (yield 97%).

$^1$H NMR (CDCl$_3$) δ: 0.18(6H, s), 0.97(9H, s), 2.34(6H, s), 6.57(2H, s).

Reference Example 48

(4-{[tert-butyl(dimethyl)silyl]oxy}-2,6-dimethylphenyl)boronic acid

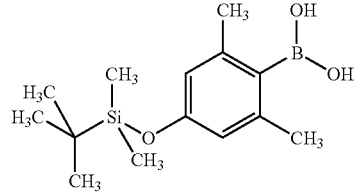

The title compound was obtained as pale-yellow prism crystals from (4-bromo-3,5-dimethylphenoxy)(tert-butyl)dimethylsilane according to a method similar to the method of Reference Example 32 (yield 53%).

$^1$H NMR (CDCl$_3$) δ: 0.19(6H, s), 0.98(9H, s), 2.32(6H, s), 4.58(2H, s), 6.47(2H, s).

Reference Example 49 methyl 4'-{[tert-butyl(dimethyl)silyl]oxy}-6-isopropoxy-2',6'-dimethylbiphenyl-3-carboxylate

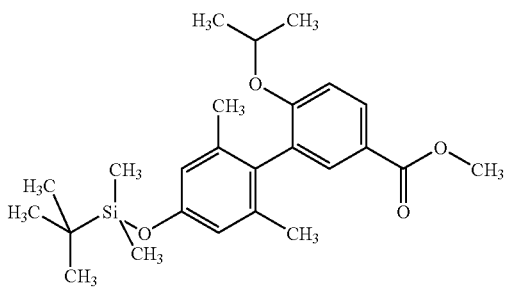

A mixture of (4-{[tert-butyl(dimethyl)silyl]oxy}-2,6-dimethylphenyl)boronic acid (500 mg, 1.83 mmol) and methyl 3-bromo-4-isopropoxybenzoate (667 mg, 2.38 mmol) was dissolved in a mixture of 2 M aqueous sodium carbonate solution (2.38 mL) and toluene (20 mL), and after argon substitution, 2-dicyclohexylphosphino-2'-(N,N-dimethylamino)biphenyl (118 mg, 0.29 mmol) and tris(dibenzylideneacetone)dipalladium(0) (67.0 mg, 0.07 mmol) were added. The reaction mixture was heated under reflux under an argon atmosphere for 1 day. The reaction mixture was cooled, and brine was added. The mixture was extracted with ethyl acetate and the organic layer was dried over anhydrous sodium sulfate and concentrated under reduced pressure. The residue was purified by silica gel chromatography (hexane-hexane/ethyl acetate=10/1) to give the title compound (642 mg, yield 82%) as a yellow oil.

$^1$H NMR (CDCl$_3$) δ: 0.19-0.26(6H, m), 1.00(9H, s), 1.17 (6H, d, J=6.0 Hz), 1.92(6H, s), 3.87(3H, s), 4.42-4.57(1H, m), 6.57(2H, s), 6.95(1H, d, J=8.7 Hz), 7.74(1H, d, J=2.3 Hz), 7.99(1H, dd, J=8.7, 2.4 Hz).

Reference Example 50

(4'-{[tert-butyl(dimethyl)silyl]oxy}-6-isopropoxy-2',6'-dimethylbiphenyl-3-yl)methanol

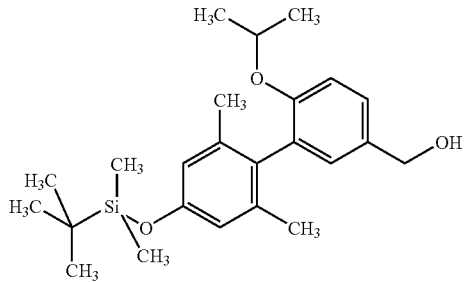

The title compound was obtained as a colorless oil from methyl 4'-{[tert-butyl(dimethyl)silyl]oxy}-6-isopropoxy-2',6'-dimethylbiphenyl-3-carboxylate according to a method similar to the method of Reference Example 16 (yield 85%).

$^1$H NMR (CDCl$_3$) δ: 0.22(6H, s), 1.00(9H, s), 1.10(6H, d, J=6.2 Hz), 1.94-1.98(6H, m), 4.16-4.31(1H, m), 4.64(2H, d, J=3.6 Hz), 6.57(2H, s), 6.94(1H, d, J=8.5 Hz), 7.04(1H, d, J=2.1 Hz), 7.24-7.31(1H, m).

Example 1 methyl 3-(4-{[2'-methyl-4'-(tetrahydro-2H-pyran-2-yloxy)biphenyl-3-yl]methoxy}phenyl)propanoate

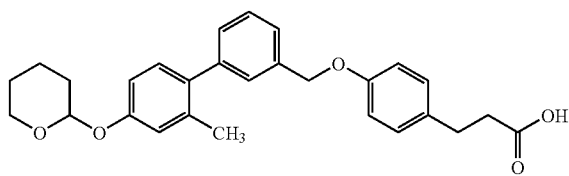

A solution of methyl 3-(4-hydroxyphenyl)propanoate (1.43 g, 7.94 mmol), [2'-methyl-4'-(tetrahydro-2H-pyran-2-yloxy)biphenyl-3-yl]methanol (2.37 g, 7.94 mmol) and tributylphosphine (2.97 mL, 11.9 mmol) in toluene (120 mL) was stirred under ice-cooling and 1,1'-(azodicarbonyl)dipiperidine (3.00 g, 11.9 mmol) was added by small portions. The mixture was warmed to room temperature and stirred for 24 hrs. Hexane (60 mL) was added to the reaction mixture and the precipitated insoluble material was filtered off. The filtrate was concentrated under reduced pressure and the residue was purified by silica gel column chromatography (hexane-20% ethyl acetate/hexane) to give the title compound as a colorless oil (3.05 g, yield 83%).

$^1$H NMR (CDCl$_3$) δ: 1.58-1.75(3H, m), 1.85-1.90(2H, m), 1.97-2.08(1H, m), 2.23(3H, s), 2.60(2H, t, J=7.8 Hz), 2.89 (2H, t, J=7.8 Hz), 3.61-3.66(4H, m), 3.91-3.99(1H, m), 5.07 (2H, s), 5.46(1H, t, J=3.1 Hz), 6.88-6.97(4H, m), 7.08-7.16 (3H, m), 7.24-7.27(1H, m), 7.35-7.43(3H, m).

Example 2

3-(4-{[2'-methyl-4'-(tetrahydro-2H-pyran-2-yloxy)biphenyl-3-yl]methoxy}phenyl)propanoic acid

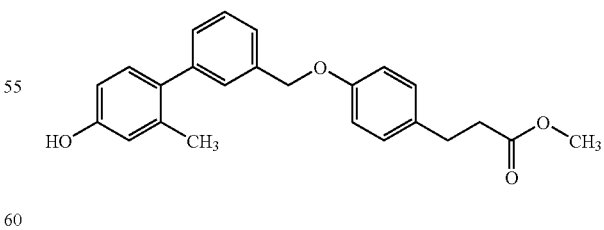

To a solution of methyl 3-(4-{[2'-methyl-4'-(tetrahydro-2H-pyran-2-yloxy)biphenyl-3-yl]methoxy}phenyl)propanoate (0.599 g, 1.30 mmol) in methanol (6 mL) and tetrahydrofuran (6 mL) was added 2 M aqueous sodium hydroxide solution (2 mL) and the mixture was stirred at room temperature for 24 hrs. Water was added to the reaction mixture, and the mixture was neutralized with 10% aqueous citric acid solution and extracted with ethyl acetate. The extract was washed with saturated brine, dried over anhydrous sodium sulfate and concentrated under reduced pressure. The residue was recrystallized from ethyl acetate-hexane to give the title compound (0.436 g, yield 75%) as colorless needle crystals.

$^1$H NMR (CDCl$_3$) δ: 1.58-1.76(3H, m), 1.85-1.90(2H, m), 1.97-2.10(1H, m), 2.23(3H, s), 2.65(2H, t, J=7.6 Hz), 2.91 (2H, t, J=7.6 Hz), 3.60-3.66(1H, m), 3.91-3.99(1H, m), 5.08 (2H, s), 5.46(1H, t, J=3.1 Hz), 6.89-6.97(4H, m), 7.11-7.16 (3H, m), 7.24-7.27(1H, m), 7.35-7.43(3H, m).

Example 3 methyl 3-{4-[(4'-hydroxy-2'-methylbiphenyl-3-yl)methoxy]phenyl}propanoate

A solution of methyl 3-(4-{[2'-methyl-4'-(tetrahydro-2H-pyran-2-yloxy)biphenyl-3-yl]methoxy}phenyl)propanoate (3.78 g, 8.21 mmol) and p-toluenesulfonic acid monohydrate (0.156 g, 0.821 mmol) in methanol (60 mL) was stirred at room temperature for 2 hrs. The reaction solvent was evaporated under reduced pressure, and the residue was diluted with ethyl acetate, washed with saturated brine, dried over anhydrous magnesium sulfate and concentrated under reduced pressure. The residue was purified by silica gel column chromatography (20%-60% ethyl acetate/hexane) to give the title compound (3.04 g, yield 98%) as a colorless viscous oil.

MS m/z 377 (MH⁺)

Example 4

3-{4-[(4'-hydroxy-2'-methylbiphenyl-3-yl)methoxy]phenyl}propanoic acid

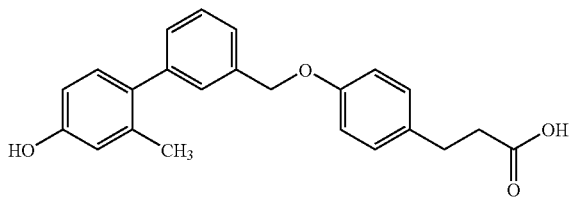

The title compound was obtained as colorless prism crystals from methyl 3-{4-[(4'-hydroxy-2'-methylbiphenyl-3-yl)methoxy]phenyl}propanoate according to a method similar to the method of Example 2 (yield 31%, recrystallized from hexane-ethyl acetate).

$^1$H NMR (CDCl$_3$) δ: 2.21(3H, s), 2.65(2H, t, J=7.7 Hz), 2.91(2H, t, J=7.7 Hz), 5.07(2H, s), 6.69-6.75(2H, m), 6.92(2H, d, J=8.7 Hz), 7.09-7.15(3H, m), 7.23-7.26(1H, m), 7.35-7.43(3H, m).

Example 5 methyl 3-{4-[(4'-methoxy-2'-methylbiphenyl-3-yl)methoxy]phenyl}propanoate

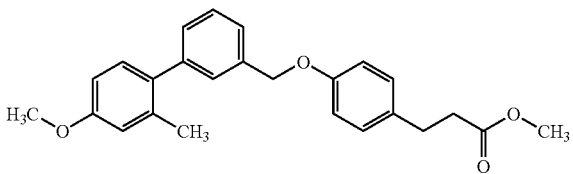

The title compound was obtained as a pale-yellow oil from methyl 3-{4-[(4'-hydroxy-2'-methylbiphenyl-3-yl)methoxy]phenyl}propanoate and methanol according to a method similar to the method of Example 1 (yield 92%).

$^1$H NMR (CDCl$_3$) δ: 2.24(3H, s), 2.60(2H, t, J=7.8 Hz), 2.89(2H, t, J=7.8 Hz), 3.66(3H, s), 3.83(3H, s), 5.07(2H, s), 6.77-6.82(2H, m), 6.91(2H, d, J=8.7 Hz), 7.10-7.17(3H, m), 7.24-7.27(1H, m), 7.35-7.43(3H, m).

Example 6

3-{4-[(4'-methoxy-2'-methylbiphenyl-3-yl)methoxy]phenyl}propanoic acid

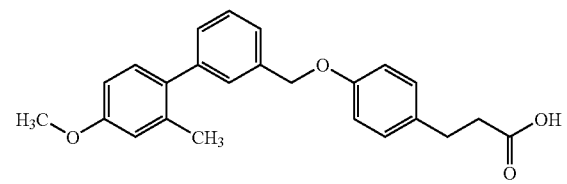

The title compound was obtained as colorless needle crystals from methyl 3-{4-[(4'-methoxy-2'-methylbiphenyl-3-yl)methoxy]phenyl}propanoate according to a method similar to the method of Example 2 (yield 56%, recrystallized from hexane-ethyl acetate).

$^1$H NMR (CDCl$_3$) δ: 2.24(3H, s), 2.65(2H, t, J=7.7 Hz), 2.91(2H, t, J=7.7 Hz), 3.83(3H, s), 5.08(2H, s), 6.77-6.81(2H, m), 6.92(2H, d, J=8.7 Hz), 7.11-7.18(3H, m), 7.24-7.27(1H, m), 7.36-7.44(3H, m).

Example 7 methyl 3-(4-{[4'-(cyclopropylmethoxy)-2'-methylbiphenyl-3-yl]methoxy}phenyl)propanoate

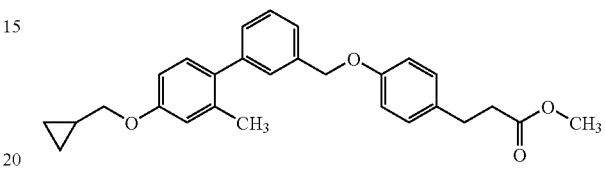

The title compound was obtained as a colorless oil from methyl 3-{4-[(4'-hydroxy-2'-methylbiphenyl-3-yl)methoxy]phenyl}propanoate and cyclopropylmethanol according to a method similar to the method of Example 1 (yield 85%).

MS m/z 431(MH⁺)

Example 8

3-(4-{[4'-(cyclopropylmethoxy)-2'-methylbiphenyl-3-yl]methoxy}phenyl)propanoic acid

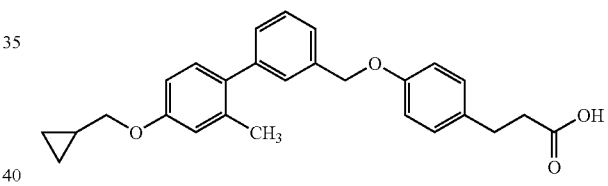

The title compound was obtained as colorless needle crystals from methyl 3-(4-{[4'-(cyclopropylmethoxy)-2'-methylbiphenyl-3-yl]methoxy}phenyl)propanoate according to a method similar to the method of Example 2 (yield 43%, recrystallized from hexane-ethyl acetate).

MS m/z 417(MH⁺)

Example 9 methyl 3-{4-[(4'-isopropoxy-2'-methylbiphenyl-3-yl)methoxy]phenyl}propanoate

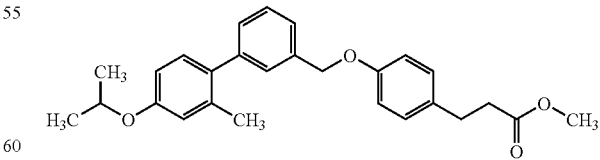

The title compound was obtained as a colorless oil from methyl 3-{4-[(4'-hydroxy-2'-methylbiphenyl-3-yl)methoxy]phenyl}propanoate and 2-propanol according to a method similar to the method of Example 1 (yield 78%).

MS m/z 419(MH⁺)

Example 10

3-{4-[(4'-isopropoxy-2'-methylbiphenyl-3-yl)methoxy]phenyl}propanoic acid

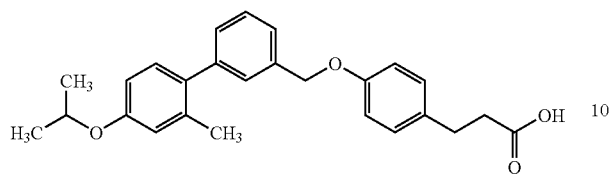

The title compound was obtained as colorless needle crystals from methyl 3-{4-[(4'-isopropoxy-2'-methylbiphenyl-3-yl)methoxy]phenyl}propanoate according to a method similar to the method of Example 2 (yield 56%, recrystallized from hexane-ethyl acetate)

MS m/z 405(MH$^+$).

Example 11 methyl 3-(4-{[4'-(benzyloxy)-2'-methylbiphenyl-3-yl]methoxy}phenyl)propanoate

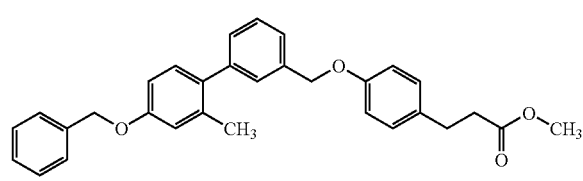

The title compound was obtained as a colorless oil from methyl 3-{4-[(4'-hydroxy-2'-methylbiphenyl-3-yl)methoxy]phenyl}propanoate and benzyl alcohol according to a method similar to the method of Example 1 (yield 79%).

MS m/z 467(MH$^+$)

Example 12

3-(4-{[4'-(benzyloxy)-2'-methylbiphenyl-3-yl]methoxy}phenyl)propanoic acid

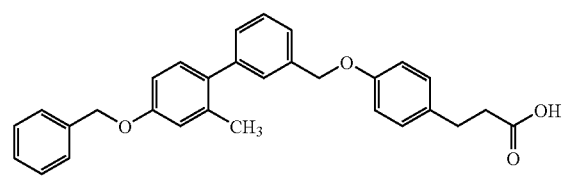

The title compound was obtained as colorless needle crystals from methyl 3-(4-{[4'-(benzyloxy)-2'-methylbiphenyl-3-yl]methoxy}phenyl)propanoate according to a method similar to the method of Example 2 (yield 45%, recrystallized from hexane-ethyl acetate).

MS m/z 453(MH$^+$)

Example 13 methyl 3-[4-({2'-methyl-4'-[2-(4-methyl-1,3-thiazol-5-yl)ethoxy]biphenyl-3-yl}methoxy)phenyl]propanoate

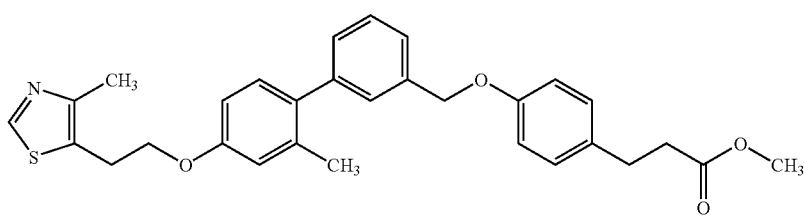

The title compound was obtained as a brown oil from methyl 3-{4-[(4'-hydroxy-2'-methylbiphenyl-3-yl)methoxy]phenyl}propanoate and 2-(4-methyl-1,3-thiazol-5-yl)ethanol according to a method similar to the method of Example 1 (yield 62%).

MS m/z 502(MH$^+$)

Example 14

3-[4-({2'-methyl-4'-[2-(4-methyl-1,3-thiazol-5-yl)ethoxy]biphenyl-3-yl}methoxy)phenyl]propanoic acid

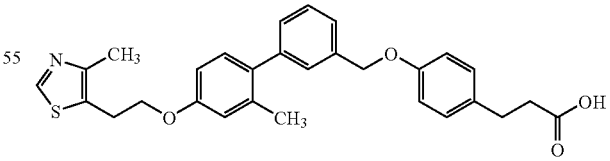

The title compound was obtained as colorless plate crystals from methyl 3-[4-({2'-methyl-4'-[2-(4-methyl-1,3-thiazol-5-yl)ethoxy]biphenyl-3-yl}methoxy)phenyl]propanoate according to a method similar to the method of Example 2 (yield 77%, recrystallized from hexane-ethyl acetate).

MS m/z 488(MH$^+$)

Example 15 methyl 3-(4-{[2'-methyl-4'-(3-(pyridin-2-yl)propoxy)biphenyl-3-yl]methoxy}phenyl)propanoate

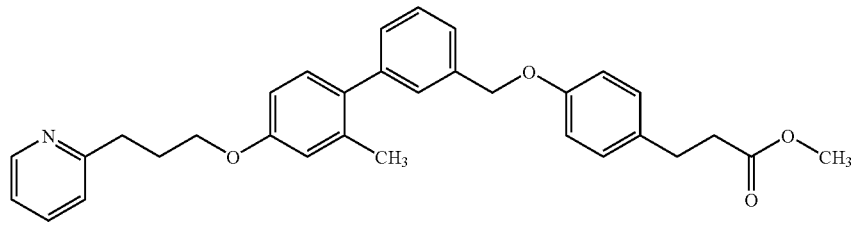

A solution of methyl 3-{4-[(4'-hydroxy-2'-methylbiphenyl-3-yl)methoxy]phenyl}propanoate (0.602 g, 1.60 mmol), 3-(pyridin-2-yl)propan-1-ol (0.822 g, 6.00 mmol) and triphenylphosphine (1.57 g, 6.00 mmol) in tetrahydrofuran (20 mL) under ice-cooling was stirred and diethyl azodicarboxylate (40% toluene solution, 2.72 mL, 6.00 mmol) was added. The mixture was warmed to room temperature and stirred for 42 hrs. The reaction mixture was concentrated under reduced pressure and the residue was purified by silica gel column chromatography (20%-60% ethyl acetate/hexane) and preparative HPLC to give the title compound as a yellow viscous oil (0.446 g, yield 56%).

MS m/z 496(MH$^+$)

Example 16

3-(4-{[2'-methyl-4'-(3-(pyridin-2-yl)propoxy)biphenyl-3-yl]methoxy}phenyl)propanoic acid

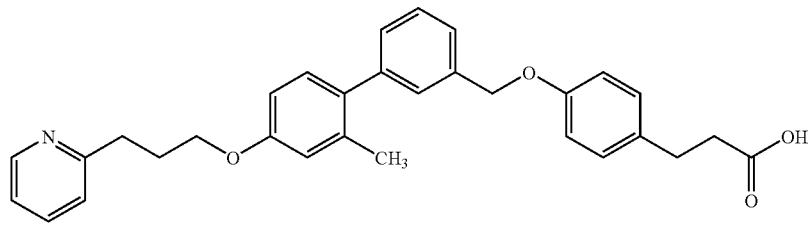

A solution of methyl 3-(4-{[2'-methyl-4'-(3-(pyridin-2-yl)propoxy)biphenyl-3-yl]methoxy}phenyl)propanoate (0.401 g, 0.809 mmol) in methanol (5 mL) and tetrahydrofuran (5 mL) was added 2 M aqueous sodium hydroxide solution (1.5 mL) and the mixture was stirred at room temperature for 75 hrs. Water was added to the reaction mixture, and the mixture was neutralized with 10% aqueous citric acid solution and extracted with ethyl acetate. The extract was washed with saturated brine, dried over anhydrous sodium sulfate and concentrated under reduced pressure. The residue was purified by silica gel column chromatography (50% ethyl acetate/hexane-ethyl acetate) and recrystallized from ethyl acetate-hexane to give the title compound (0.186 g, yield 48%) as colorless prism crystals.

MS m/z 482(MH$^+$)

Example 17 methyl 3-(4-{[2'-methyl-4'-(1-propylbutoxy)biphenyl-3-yl]methoxy}phenyl)propanoate

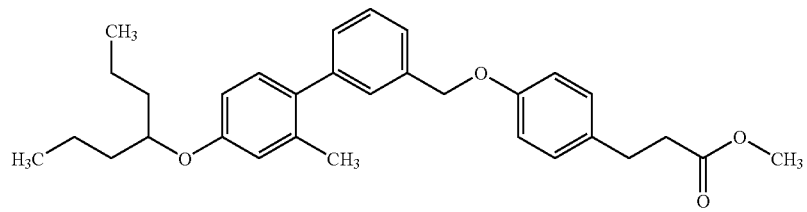

The title compound was obtained as a colorless oil from methyl 3-{4-[(4'-hydroxy-2'-methylbiphenyl-3-yl)methoxy]phenyl}propanoate and 4-heptanol according to a method similar to the method of Example 1 (yield 65%).

$^1$H NMR (CDCl$_3$) δ: 0.94(6H, t, J=7.2 Hz), 1.31-1.81(8H, m), 2.22(3H, s), 2.60(2H, t, J=7.8 Hz), 2.89(2H, t, J=7.8 Hz), 3.66(3H, s) 4.23-4.31(1H, m), 5.07(2H, s), 6.74-6.80(2H, m), 6.88-6.93(2H, m), 7.10-7.16(3H, m), 7.25-7.28(1H, m), 7.36-7.43(3H, m).

Example 18

3-(4-{[2'-methyl-4'-(1-propylbutoxy)biphenyl-3-yl]methoxy}phenyl)propanoic acid

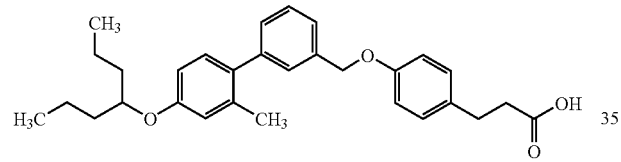

The title compound was obtained as colorless needle crystals from methyl 3-(4-{[2'-methyl-4'-(1-propylbutoxy)biphenyl-3-yl]methoxy}phenyl)propanoate according to a method similar to the method of Example 2 (yield 77%, recrystallized from hexane-ethyl acetate).

$^1$H NMR (CDCl$_3$) δ: 0.94(6H, t, J=7.3 Hz), 1.33-1.76(8H, m), 2.22(3H, s), 2.65(2H, t, J=7.7 Hz), 2.91(2H, t, J=7.7 Hz), 4.23-4.31(1H, m), 5.07(2H, s), 6.73-6.80(2H, m), 6.92(2H, d, J=8.6 Hz), 7.13(3H, d, J=8.6 Hz), 7.24-7.28(1H, m), 7.35-7.43(3H, m).

Example 19 ethyl 3-(4-{[4'-(benzyloxy)-2',6'-dimethylbiphenyl-3-yl]methoxy}-2-fluorophenyl)propanoate

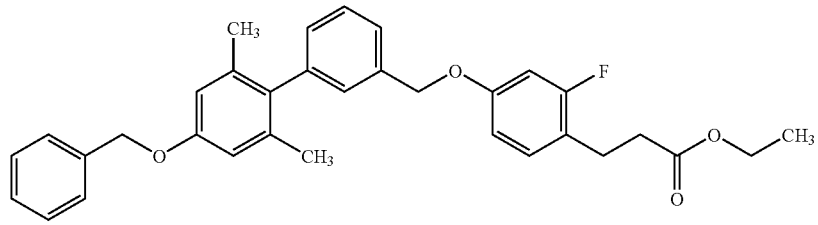

The title compound was obtained as a colorless oil from ethyl 3-(2-fluoro-4-hydroxyphenyl)propanoate and [4'-(benzyloxy)-2',6'-dimethylbiphenyl-3-yl]methanol according to a method similar to the method of Example 1 (yield 76%).

MS m/z 513(MH$^+$)

Example 20

3-(4-{[4'-(benzyloxy)-2',6'-dimethylbiphenyl-3-yl]methoxy}-2-fluorophenyl)propanoic acid

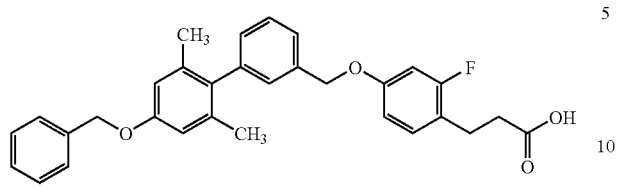

The title compound was obtained as colorless prism crystals from ethyl 3-(4-{[4'-(benzyloxy)-2',6'-dimethylbiphenyl-3-yl]methoxy}-2-fluorophenyl)propanoate according to a method similar to the method of Example 2 (yield 57%, recrystallized from heptane-ethyl acetate).

MS m/z 485(MH$^+$)

Example 21 ethyl 3-(4-{[4'-(2-ethoxyethoxy)-2',6'-dimethylbiphenyl-3-yl]methoxy}-2-fluorophenyl)propanoate

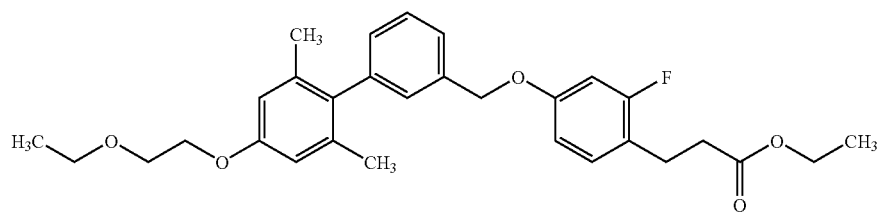

The title compound was obtained as a colorless oil from ethyl 3-(2-fluoro-4-hydroxyphenyl)propanoate and [4'-(2-ethoxyethoxy)-2',6'-dimethylbiphenyl-3-yl]methanol according to a method similar to the method of Example 1 (yield 93%).

MS m/z 495(MH$^+$)

Example 22

3-(4-{[4'-(2-ethoxyethoxy)-2',6'-dimethylbiphenyl-3-yl]methoxy}-2-fluorophenyl)propanoic acid

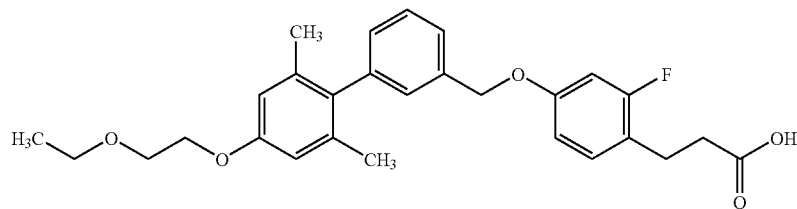

The title compound was obtained as colorless prism crystals from ethyl 3-(4-{[4'-(2-ethoxyethoxy)-2',6'-dimethylbiphenyl-3-yl]methoxy}-2-fluorophenyl)propanoate according to a method similar to the method of Example 2 (yield 77%, recrystallized from hexane-ethyl acetate).

MS m/z 467(MH$^+$)

Example 23 ethyl 3-(4-{[2',6'-dimethyl-4'-(tetrahydro-2H-pyran-2-yloxy)biphenyl-3-yl]methoxy}-2-fluorophenyl)propanoate

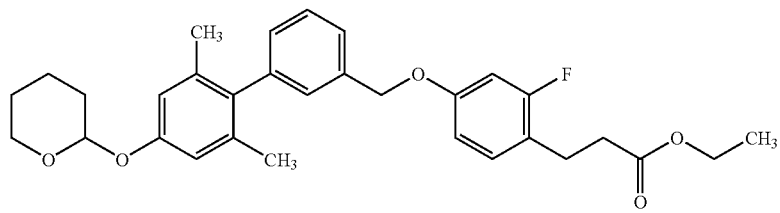

The title compound was obtained as a colorless oil from ethyl 3-(2-fluoro-4-hydroxyphenyl)propanoate and [2',6'-dimethyl-4'-(tetrahydro-2H-pyran-2-yloxy)biphenyl-3-yl]methanol according to a method similar to the method of Example 1 (yield 89%).
MS m/z 507(MH$^+$)

Example 24 ethyl 3-{2-fluoro-4-[(4'-hydroxy-2',6'-dimethylbiphenyl-3-yl)methoxy]phenyl}propanoate

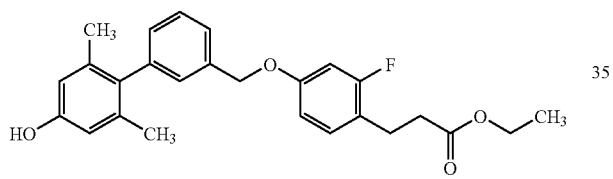

The title compound was obtained as a colorless oil from ethyl 3-(4-{[2',6'-dimethyl-4'-(tetrahydro-2H-pyran-2-yloxy)biphenyl-3-yl]methoxy}-2-fluorophenyl)propanoate according to a method similar to the method of Example 3 (yield 97%).
MS m/z 423(MH$^+$)

Example 25

3-{2-fluoro-4-[(4'-hydroxy-2',6'-dimethylbiphenyl-3-yl)methoxy]phenyl}propanoic acid

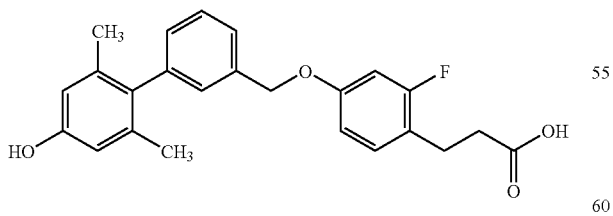

The title compound was obtained as colorless prism crystals from ethyl 3-{2-fluoro-4-[(4'-hydroxy-2',6'-dimethylbiphenyl-3-yl)methoxy]phenyl}propanoate according to a method similar to the method of Example 2 (yield 82%, recrystallized from hexane-ethyl acetate).
MS m/z 395(MH$^+$)

Example 26 ethyl 3-(4-{[2',6'-dimethyl-4'-(1-propylbutoxy)biphenyl-3-yl]methoxy}-2-fluorophenyl)propanoate

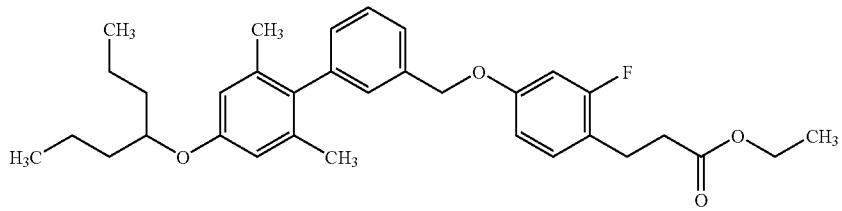

The title compound was obtained as a colorless oil from ethyl 3-{2-fluoro-4-[(4'-hydroxy-2',6'-dimethylbiphenyl-3-yl)methoxy]phenyl}propanoate and 4-heptanol according to a method similar to the method of Example 1 (yield 88%).

$^1$H NMR (CDCl$_3$) δ: 0.94(6H, t, J=7.2 Hz), 1.23(3H, t, J=7.2 Hz), 1.33-1.76(8H, m), 1.98(6H, s), 2.57(2H, t, J=7.6 Hz), 2.89(2H, t, J=7.6 Hz), 4.12(2H, q, J=7.2 Hz), 4.21-4.29 (1H, m), 5.06(2H, s), 6.62-6.70(4H, m), 7.05-7.12(2H, m), 7.18(1H, s), 7.33-7.38(1H, m), 7.42(1H, t, J=7.5 Hz).

Example 27

3-(4-{[2',6'-dimethyl-4'-(1-propylbutoxy)biphenyl-3-yl]methoxy}-2-fluorophenyl)propanoic acid

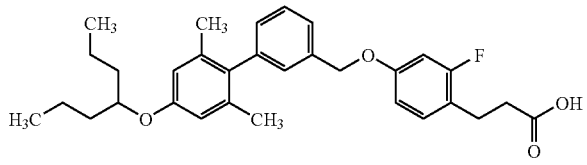

The title compound was obtained as colorless needle crystals from ethyl 3-(4-{[2',6'-dimethyl-4'-(1-propylbutoxy)biphenyl-3-yl]methoxy}-2-fluorophenyl)propanoate according to a method similar to the method of Example 2 (yield 62%, recrystallized from heptane-ethyl acetate).

$^1$H NMR (CDCl$_3$) δ: 0.94(6H, t, J=7.3 Hz), 1.33-1.76(8H, m), 1.97(6H, s), 2.64(2H, t, J=7.6 Hz), 2.91(2H, t, J=7.6 Hz), 4.21-4.29(1H, m), 5.06(2H, s), 6.63-6.71(4H, m), 7.06-7.13 (2H, m), 7.18(1H, s), 7.33-7.38(1H, m), 7.42(1H, t, J=7.4 Hz).

Example 28 methyl 3-[4-[[2',6'-dimethyl-4'-(tetrahydro-2H-pyran-2-yloxy)biphenyl-3-yl]methoxy]phenyl]propanoate

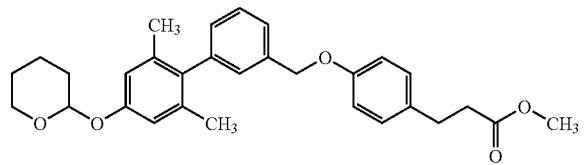

To a solution of methyl 3-(4-hydroxyphenyl)propanoate (3.28 g, 18.2 mmol), [2',6'-dimethyl-4'-(tetrahydro-2H-pyran-2-yloxy)biphenyl-3-yl]methanol (5.15 g, 16.5 mmol) and triphenylphosphine (5.63 g, 21.5 mmol) in tetrahydrofuran (100 mL) was added dropwise diethyl azodicarboxylate (40% toluene solution, 9.7 mL) at 0° C. with stirring, and the mixture was stirred at room temperature for 48 hrs. The reaction mixture was concentrated under reduced pressure and the residue was purified by silica gel column chromatography (hexane/ethyl acetate=10/1-hexane/ethyl acetate=3/1) to give the title compound (2.92 g, yield 37%) as a yellow oil.

$^1$H NMR (CDCl$_3$) δ: 1.57-1.78(3H, m), 1.82-1.90(2H, m), 1.98(6H, s), 2.02(1H, m), 2.59(2H, t, J=7.8 Hz), 2.89(2H, t, J=7.8 Hz), 3.62(1H, m), 3.66(3H, s), 3.97(1H, m), 5.08(2H, s), 5.45(1H, t, J=3.0 Hz), 6.81(2H, s), 6.89(2H, d, J=8.4 Hz), 7.05-7.14(3H, m), 7.18(1H, s), 7.34-7.47(2H, m).

Example 29 methyl 3-[4-[(4'-hydroxy-2',6'-dimethylbiphenyl-3-yl)methoxy]phenyl]propanoate

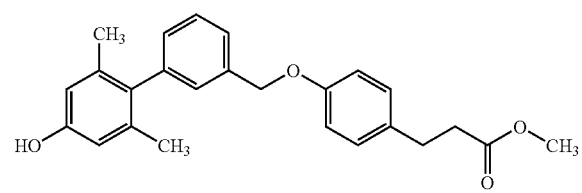

A mixture of methyl 3-[4-[[2',6'-dimethyl-4'-(tetrahydro-2H-pyran-2-yloxy)biphenyl-3-yl]methoxy]phenyl]propanoate (2.92 g, 6.15 mmol), p-toluenesulfonic acid monohydrate (0.12 g, 0.62 mmol) and methanol (60 mL) was stirred at room temperature for 2 hrs., and the mixture was concentrated under reduced pressure. The residue was purified by silica gel column chromatography (hexane/ethyl acetate=10/1-hexane/ethyl acetate=1/2) to give the title compound (2.12 g, yield 88%) as a red oil.

$^1$H NMR (CDCl$_3$) δ: 1.96(6H, s), 2.59(2H, t, J=7.8 Hz), 2.89(2H, t, J=7.8 Hz), 3.66(3H, s), 4.63(1H, s), 5.08(2H, s), 6.59(2H, s), 6.89(2H, d, J=8.7 Hz), 7.05-7.13(3H, m), 7.17 (1H, s), 7.35-7.45(2H, m).

Example 30

3-[4-[(4'-methoxy-2',6'-dimethylbiphenyl-3-yl)methoxy]phenyl]propanoic acid

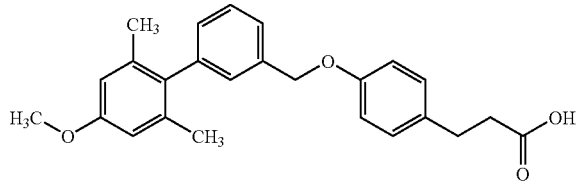

To a solution of methyl 3-[4-[(4'-hydroxy-2',6'-dimethylbiphenyl-3-yl)methoxy]phenyl]propanoate (0.20 g, 0.51 mmol), methanol (0.041 mL, 1.02 mmol) and triphenylphosphine (0.18 g, 0.67 mmol) in tetrahydrofuran (4.0 mL) was added dropwise diethyl azodicarboxylate (40% toluene solution, 0.30 mL) at 0° C. with stirring and the mixture was stirred at room temperature for 12 hrs. The reaction mixture was concentrated under reduced pressure and the residue was purified by silica gel column chromatography (hexane/ethyl acetate=10/1-hexane/ethyl acetate=3/1) to give a yellow oil (0.13 g, yield 65%).

To a mixture of the product obtained, methanol (2 mL) and tetrahydrofuran (4 mL) was added 1 N aqueous sodium hydroxide solution (0.66 mL) at room temperature with stirring and the mixture was stirred at the same temperature for 1 hr. The reaction mixture was adjusted to pH3 with 1 N hydrochloric acid, and the mixture was extracted with ethyl acetate. The ethyl acetate layer was washed with water and saturated brine, dried over anhydrous magnesium sulfate, and concentrated under reduced pressure. The residue was purified by silica gel column chromatography (hexane/ethyl acetate=4/1-hexane/ethyl acetate=1/2) to give the title compound (0.12 g, yield 89%) as colorless crystals.

MS(APCI-): 389 (M-H)

Example 31

3-[4-[(4'-hydroxy-2',6'-dimethylbiphenyl-3-yl)methoxy]phenyl]propanoic acid

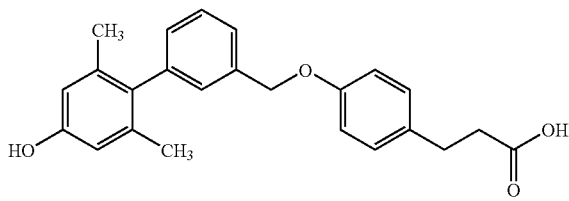

To a solution of methyl 3-[4-[(4'-hydroxy-2',6'-dimethylbiphenyl-3-yl)methoxy]phenyl]propanoate (0.18 g, 0.46 mmol) in methanol (2 mL) and tetrahydrofuran (4 mL) was added 1 N aqueous sodium hydroxide solution (0.91 mL) and the mixture was stirred at room temperature for 1 hr. The reaction mixture was concentrated and the residue was diluted with ethyl acetate, washed with 1 N hydrochloric acid and saturated brine, dried and concentrated under reduced pressure. The residue was crystallized from hexane/ethyl acetate=4/1 to give the title compound (0.13 g, yield 74%) as colorless crystals.

MS(APCI-): 375(M-H)

Example 32 methyl 3-[4-[(4'-chloro-2'-methylbiphenyl-3-yl)methoxy]phenyl]propanoate

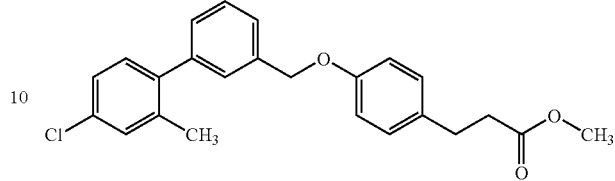

A mixture of methyl 3-[4-[(3-bromobenzyl)oxy]phenyl]propanoate (0.5 g, 1.43 mmol), 4-chloro-2-methylphenylboronic acid (0.30 g, 1.72 mmol), tetrakis(triphenylphosphine)palladium(0) (0.083 g, 0.072 mmol), sodium carbonate (0.46 g, 4.29 mmol), water (5 mL), ethanol (5 mL) and toluene (25 mL) was stirred under an argon atmosphere at 90° C. for 16 hrs. The reaction mixture was cooled, diluted with ethyl acetate, washed with water and saturated brine, dried and concentrated under reduced pressure. The residue was purified by silica gel column chromatography (hexane/ethyl acetate=10/1-4/1) to give the title compound (0.50 g, yield 88%) as a colorless oil.

$^1$H NMR (CDCl$_3$) δ: 2.22(3H, s), 2.60(2H, t, J=7.8 Hz), 2.90(2H, t, J=7.8 Hz), 3.66(3H, s), 5.08(2H, s), 6.91(2H, d, J=8.7 Hz), 7.08-7.28(6H, m), 7.34(1H, br), 1.38-7.46(2H, m).

Example 33

3-[4-[(4'-chloro-2'-methylbiphenyl-3-yl)methoxy]phenyl]propanoic acid

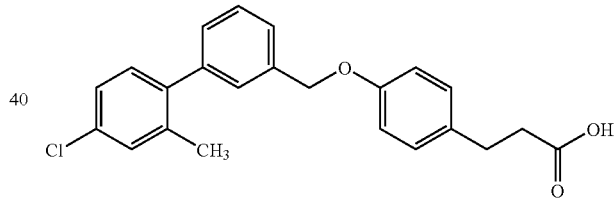

The title compound was obtained as colorless crystals from methyl 3-[4-[(4'-chloro-2'-methylbiphenyl-3-yl)methoxy]phenyl]propanoate according to a method similar to the method of Example 31 (yield 73%).

MS(APCI-): 379(M-H), 381

Example 34 methyl 3-[4-[(4'-fluoro-2'-methylbiphenyl-3-yl)methoxy]phenyl]propanoate

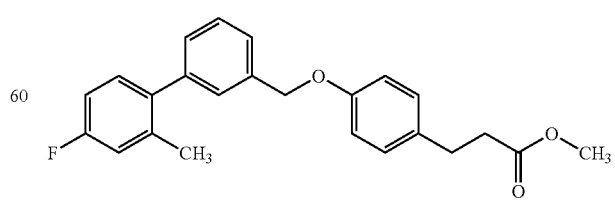

The title compound was obtained as colorless crystals from methyl 3-[4-[(3-bromobenzyl)oxy]phenyl]propanoate and 4-fluoro-2-methylphenylboronic acid according to a method similar to the method of Example 32 (yield 94%).

¹H NMR (CDCl₃) δ: 2.23(3H, s), 2.60(2H, t, J=7.8 Hz), 2.90(2H, t, J=7.8 Hz), 3.66(3H, s), 5.08(2H, s), 6.86-7.00(4H, m), 7.07-7.28(4H, m), 7.31-7.46(3H, m).

Example 35

3-[4-[(4'-fluoro-2'-methylbiphenyl-3-yl)methoxy]phenyl]propanoic acid

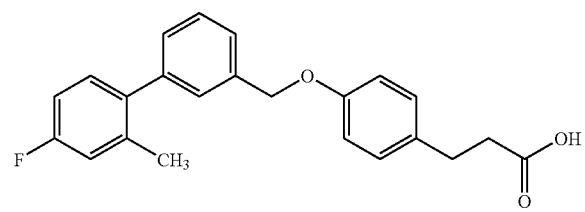

The title compound was obtained as colorless crystals from methyl 3-[4-[(4'-fluoro-2'-methylbiphenyl-3-yl)methoxy]phenyl]propanoate according to a method similar to the method of Example 31 (yield 81%).

MS(APCI-): 363(M-H)

Example 36 methyl 3-[4-[[4'-(2-ethoxyethoxy)-2',6'-dimethylbiphenyl-3-yl]methoxy]phenyl]propanoate

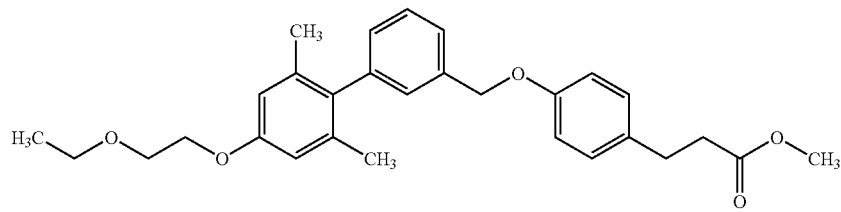

To a solution of methyl 3-[4-[(4'-hydroxy-2',6'-dimethylbiphenyl-3-yl)methoxy]phenyl]propanoate (0.20 g, 0.51 mmol), 2-ethoxyethanol (0.099 mL, 1.02 mmol) and triphenylphosphine (0.18 g, 0.67 mmol) in tetrahydrofuran (4.0 mL) was added dropwise diethyl azodicarboxylate (40% toluene solution, 0.30 mL) at 0° C. with stirring and the mixture was stirred at room temperature for 12 hrs. The reaction mixture was concentrated under reduced pressure and the residue was purified by silica gel column chromatography (hexane/ethyl acetate=10/1-hexane/ethyl acetate=3/1) to give the title compound (0.12 g, yield 51%) as a colorless oil.

¹H NMR (CDCl₃) δ: 1.25(3H, t, J=6.9 Hz), 1.98(6H, s), 2.59(2H, t, J=7.8 Hz), 2.89(2H, t, J=7.8 Hz), 3.62(2H, q, J=6.9 Hz), 3.66(3H, s), 3.80(2H, t, J=5.1 Hz), 4.14(2H, t, J=5.1 Hz), 5.08(2H, s), 6.68(2H, s), 6.89(2H, d, J=8.4 Hz), 7.04-7.14(3H, m), 7.17(1H, s), 7.35-7.45(2H, m).

Example 37

3-[4-[[4'-(2-ethoxyethoxy)-2',6'-dimethylbiphenyl-3-yl]methoxy]phenyl]propanoic acid

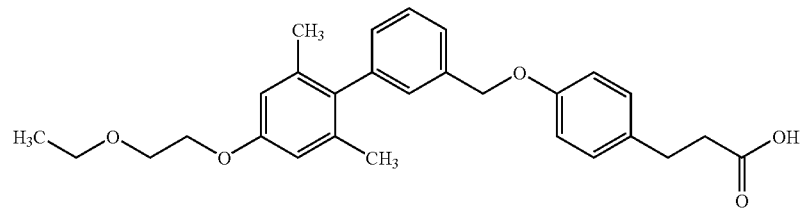

Methyl 3-[4-[[4'-(2-ethoxyethoxy)-2',6'-dimethylbiphenyl-3-yl]methoxy]phenyl]propanoate (0.12 g, 0.26 mmol) was dissolved in a mixed solution of methanol (2 mL) and tetrahydrofuran (4 mL), and 1 N aqueous sodium hydroxide solution (0.52 mL) was added at room temperature with stirring. The mixture was stirred at the same temperature for 2 hrs. After the completion of the reaction, the reaction mixture was diluted with ethyl acetate, washed successively with 1 N hydrochloric acid, water and saturated brine, dried and concentrated under reduced pressure. The residue was crystallized from hexane/ethyl acetate=4/1 to give the title compound (0.087 g, yield 75%) as colorless crystals.

MS(APCI-): 447(M-H)

Example 38 methyl 3-[4-[[4'-(benzyloxy)-2',6'-dimethylbiphenyl-3-yl]methoxy]phenyl]propanoate

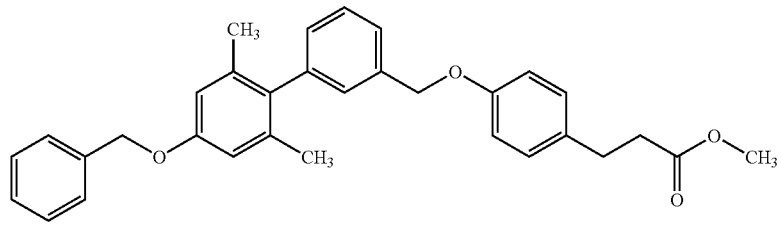

The title compound was obtained as a colorless oil from methyl 3-[4-[(4'-hydroxy-2',6'-dimethylbiphenyl-3-yl)methoxy]phenyl]propanoate and benzyl alcohol according to a method similar to the method of Example 36 (yield 63%).

$^1$H NMR (CDCl$_3$) δ: 1.99(6H, s), 2.59(2H, t, J=7.8 Hz), 2.89(2H, t, J=7.8 Hz), 3.66(3H, s), 5.07(2H, s), 5.08(2H, s), 6.75(2H, s), 6.89(2H, d, J=8.7 Hz), 7.05-7.13(3H, m), 7.18 (1H, s), 7.30-7.49(7H, m).

Example 39

3-[4-[[4'-(benzyloxy)-2',6'-dimethylbiphenyl-3-yl]methoxy]phenyl]propanoic acid

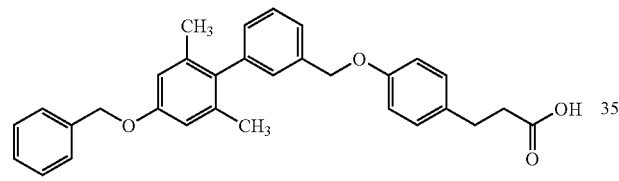

The title compound was obtained as colorless crystals from methyl 3-[4-[[4'-(benzyloxy)-2',6'-dimethylbiphenyl-3-yl]methoxy]phenyl]propanoate according to a method similar to the method of Example 37 (yield 91%).

MS(APCI−): 465(M−H).
m.p.: 123° C.

Example 40 methyl 3-[4-[[4'-(cyclopropylmethoxy)-2',6'-dimethylbiphenyl-3-yl]methoxy]phenyl]propanoate

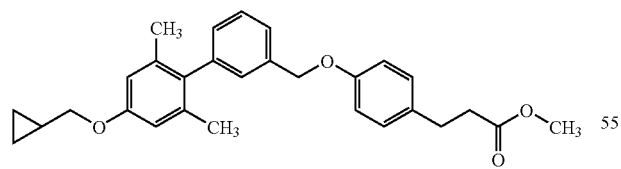

The title compound was obtained as a colorless oil from methyl 3-[4-[(4'-hydroxy-2',6'-dimethylbiphenyl-3-yl)methoxy]phenyl]propanoate and cyclopropylmethanol according to a method similar to the method of Example 36 (yield 69%).

$^1$H NMR (CDCl$_3$) δ: 0.31-0.39(2H, m), 0.60-0.69(2H, m), 1.27(1H, m), 1.98(6H, s), 2.59(2H, t, J=7.8 Hz), 2.89(2H, t, J=7.8 Hz), 3.66(3H, s), 3.81(2H, d, J=6.9 Hz), 5.08(2H, s), 6.66(2H, s), 6.89(2H, d, J=8.7 Hz), 7.05-7.13(3H, m), 7.18 (1H, s), 7.35-7.45(2H, m).

Example 41

3-[4-[[4'-(cyclopropylmethoxy)-2',6'-dimethylbiphenyl-3-yl]methoxy]phenyl]propanoic acid

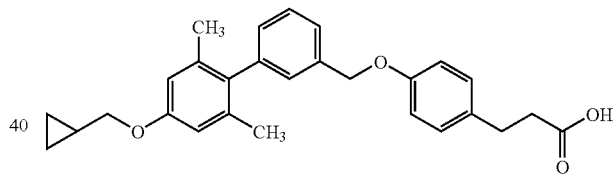

The title compound was obtained as colorless crystals from methyl 3-[4-[[4'-(cyclopropylmethoxy)-2',6'-dimethylbiphenyl-3-yl]methoxy]phenyl]propanoate according to a method similar to the method of Example 37 (yield 76%).

MS (APCI−): 429(M−H)

Example 42 methyl 3-[4-[[4'-[2-(dimethylamino)ethoxy]-2',6'-dimethylbiphenyl-3-yl]methoxy]phenyl]propanoate

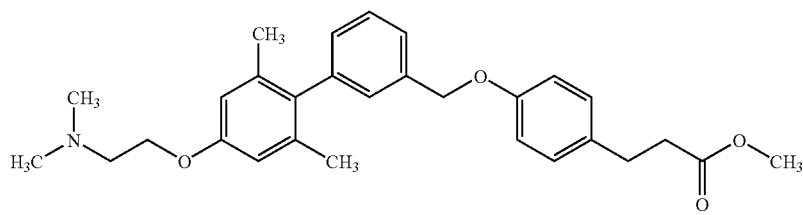

The title compound was obtained as a colorless oil from methyl 3-[4-[(4'-hydroxy-2',6'-dimethylbiphenyl-3-yl)methoxy]phenyl]propanoate and N,N-dimethylethanolamine according to a method similar to the method of Example 36 (yield 38%).

$^1$H NMR (CDCl$_3$) δ: 1.98(6H, s), 2.35(6H, s), 2.59(2H, t, J=7.8 Hz), 2.75(2H, t, J=5.7 Hz), 2.89(2H, t, J=7.8 Hz), 3.66(3H, s), 4.09(2H, t, J=5.7 Hz), 5.08(2H, S), 6.68(2H, s), 6.89(2H, d, J=8.7 Hz), 7.05-7.13(3H, m), 7.18(1H, s), 7.35-7.45(2H, m).

Example 43

3-[4-[[4'-[2-(dimethylamino)ethoxy]-2',6'-dimethylbiphenyl-3-yl]methoxy]phenyl]propanoic acid trifluoroacetate

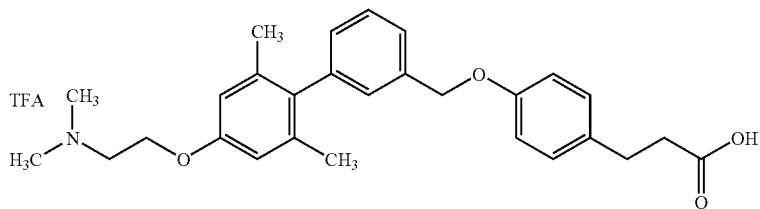

The title compound was obtained as colorless crystals from methyl 3-[4-[[4'-[2-(dimethylamino)ethoxy]-2',6'-dimethylbiphenyl-3-yl]methoxy]phenyl]propanoate according to a method similar to the method of Example 37 (yield 87%). This compound was purified by preparative HPLC.

MS(APCI−): 446(M−H, as a free form)

Example 44 methyl 3-{4-[(2',4'-dimethylbiphenyl-3-yl)methoxy]phenyl}propanoate

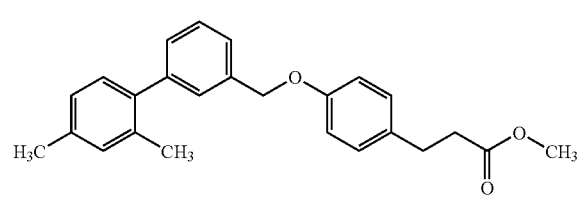

The title compound was obtained from methyl 3-(4-hydroxyphenyl)propanoate and (2',4'-dimethylbiphenyl-3-yl)methanol according to a method similar to the method of Example 1 (yield 83%).

MS m/z 375 (MH$^+$)

Example 45

3-{4-[(2',4'-dimethylbiphenyl-3-yl)methoxy]phenyl}propanoic acid

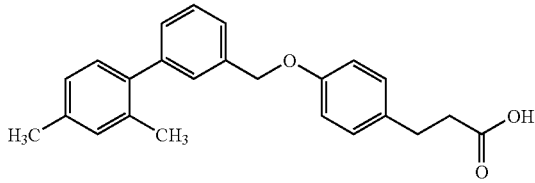

The title compound was obtained from methyl 3-{4-[(2',4'-dimethylbiphenyl-3-yl)methoxy]phenyl}propanoate according to a method similar to the method of Example 2 (yield 91%).

$^1$H NMR (CDCl$_3$) δ: 2.22(3H, s), 2.36(3H, s), 2.65(2H, t, J=7.6 Hz), 2.91(2H, t, J=7.6 Hz), 5.08(2H, s), 6.91(2H, d, J=8.4 Hz), 7.00-7.46(9H, m).

Example 46 methyl 3-{4-[(2',4',6'-trimethylbiphenyl-3-yl)methoxy]phenyl}propanoate

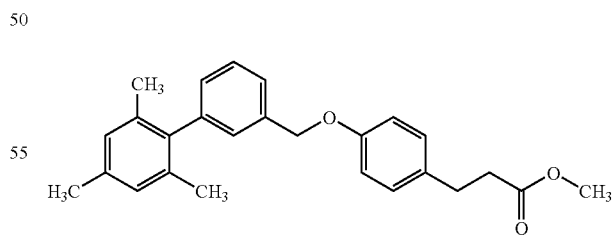

The title compound was obtained from methyl 3-(4-hydroxyphenyl)propanoate and (2',4',6'-trimethylbiphenyl-3-yl)methanol according to a method similar to the method of Example 1 (yield 71%).

$^1$H NMR (CDCl$_3$) δ: 1.98(6H, s), 2.32(3H, s), 2.59(2H, t, J=7.6 Hz), 2.89(2H, t, J=7.6 Hz), 3.66(3H, s), 5.08(2H, s), 6.88(2H, d, J=8.8 Hz), 6.93(2H, s), 7.05-7.48(6H, m).

Example 47

3-{4-[(2',4',6'-trimethylbiphenyl-3-yl)methoxy]phenyl}propanoic acid

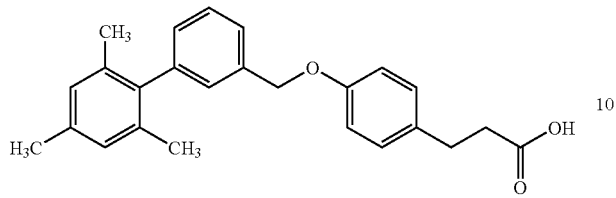

The title compound was obtained from methyl 3-{4-[(2',4',6'-trimethylbiphenyl-3-yl)methoxy]phenyl}propanoate according to a method similar to the method of Example 2 (yield 88%).

¹H NMR (CDCl₃) δ: 1.98(6H, s), 2.32(3H, s), 2.64(2H, t, J=7.4 Hz), 2.90(2H, t, J=7.4 Hz), 5.08(2H, s), 6.89(2H, d, J=8.8 Hz), 6.93(2H, s), 7.04-7.48(6H, m).

Example 48 methyl 3-(4-((6-methoxy-2',4'-dimethylbiphenyl-3-yl)methoxy)phenyl)propanoate

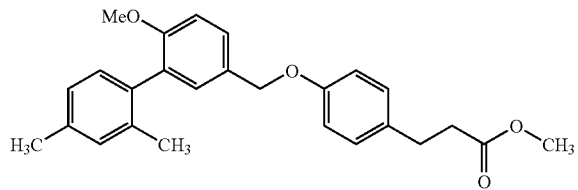

The title compound was obtained from methyl 3-(4-hydroxyphenyl)propanoate and (6-methoxy-2',4'-dimethylbiphenyl-3-yl)methanol according to a method similar to the method of Example 1 (yield 68%).

¹H NMR (CDCl₃) δ: 2.10(3H, s), 2.36(3H, s), 2.59(2H, t, J=7.6 Hz), 2.90(2H, t, J=7.6 Hz), 3.66(3H, s), 3.77(3H, s), 4.98(2H, s), 6.90(2H, d, J=8.8 Hz), 6.95(1H, d, J=8.4 Hz), 7.00-7.17(5H, m), 7.20(1H, d, J=2.2 Hz), 7.39(1H, dd, J=2.2, 8.4 Hz).

Example 49

3-(4-((6-methoxy-2',4'-dimethylbiphenyl-3-yl)methoxy)phenyl)propanoic acid

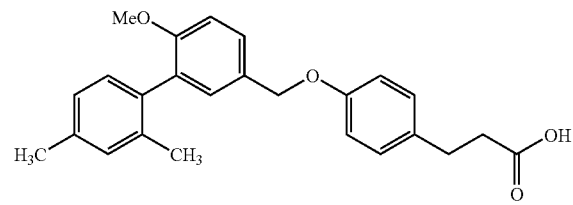

The title compound was obtained from methyl 3-(4-((6-methoxy-2',4'-dimethylbiphenyl-3-yl)methoxy)phenyl)propanoate according to a method similar to the method of Example 2 (yield 100%).

¹H NMR (CDCl₃) δ: 2.10(3H, s), 2.36(3H, s), 2.65(2H, t, J=7.6 Hz), 2.91(2H, t, J=7.6 Hz), 3.77(3H, s), 4.99(2H, s), 6.84-7.18(8H, m), 7.20(1H, d, J=2.2 Hz), 7.39(1H, dd, J=2.6, 8.4 Hz).

Example 50 ethyl 3-{2-fluoro-4-[(2',4',6'-trimethylbiphenyl-3-yl)methoxy]phenyl}propanoate

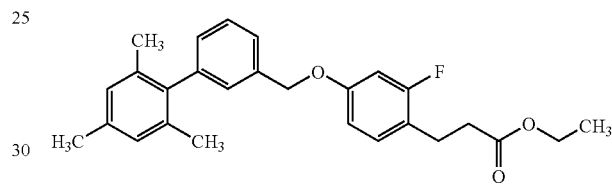

The title compound was obtained from ethyl 3-(2-fluoro-4-hydroxyphenyl)propanoate and (2',4',6'-trimethylbiphenyl-3-yl)methanol according to a method similar to the method of Example 1 (yield 74%).

MS m/z 421 (MH⁺)

Example 51

3-{2-fluoro-4-[(2',4',6'-trimethylbiphenyl-3-yl)methoxy]phenyl}propanoic acid

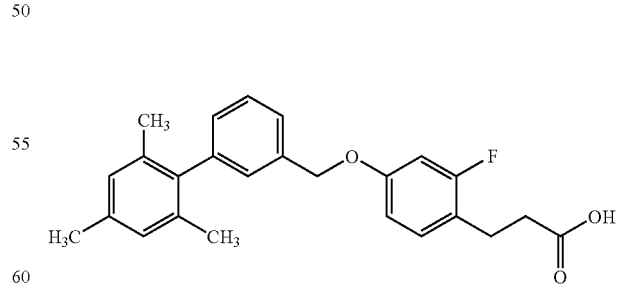

The title compound was obtained from ethyl 3-{2-fluoro-4-[(2',4',6'-trimethylbiphenyl-3-yl)methoxy]phenyl}propanoate according to a method similar to the method of Example 2 (yield 77%).

APCI(−) 391 (M−H)

Example 52 and 53 ethyl 3-{2-fluoro-4-[(2'-(4-fluorophenoxymethyl)-4',6'-dimethylbiphenyl-3-yl)methoxy]phenyl}propanoate (Example 52) and ethyl 3-{2-fluoro-4-[(4'-(4-fluorophenoxymethyl)-2',6'-dimethylbiphenyl-3-yl)methoxy]phenyl}propanoate (Example 53)

Mixture of

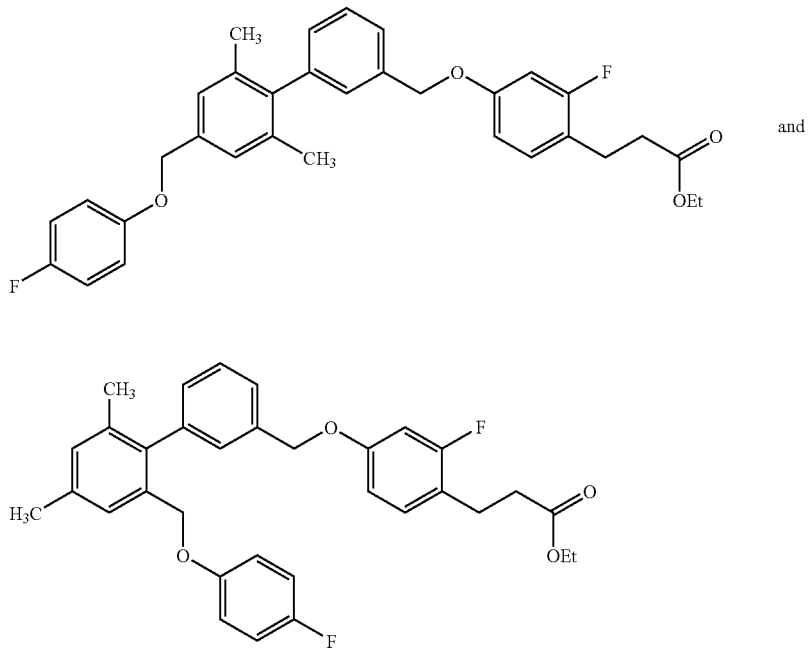

and

To a solution of the mixture (0.74 g, 2.20 mmol) obtained in Reference Example 23, ethyl 3-(2-fluoro-4-hydroxyphenyl)propanoate (0.47 g, 2.21 mmol) and tributylphosphine (0.71 mL, 2.85 mmol) in anhydrous tetrahydrofuran (40 mL) was added 1,1'-(azodicarbonyl)dipiperidine (0.72 g, 2.85 mmol) by small portions, and the mixture was stirred at room temperature for 18 hrs. The reaction mixture was diluted with diethyl ether (40 mL) and the precipitate was filtered off and the filtrate was concentrated under reduced pressure. The obtained residue was purified by silica gel column chromatography (ethyl acetate:hexane=1:10-1:5) to give a mixture (1.08 g, yield 93%) of the title compounds as a pale-yellow oil. The mixture was used for the next reaction without separation.

MS m/z 531(MH$^+$)

Example 54 and 55

3-{2-fluoro-4-[(2'-(4-fluorophenoxymethyl)-4',6'-dimethylbiphenyl-3-yl)methoxy]phenyl}propanoic acid (Example 54) and 3-{2-fluoro-4-[(4'-(4-fluorophenoxymethyl)-2',6'-dimethylbiphenyl-3-yl)methoxy]phenyl}propanoic acid (Example 55)

A mixture (1.08 g, 2.04 mmol) of ethyl 3-{2-fluoro-4-[(2'-(4-fluorophenoxymethyl)-4',6'-dimethylbiphenyl-3-yl)methoxy]phenyl}propanoate and ethyl 3-{2-fluoro-4-[(4'-(4-fluorophenoxymethyl)-2',6'-dimethylbiphenyl-3-yl)methoxy]phenyl}propanoate obtained in Examples 52 and 53 was dissolved in a mixed solvent of tetrahydrofuran (10 mL) and ethanol (10 mL). To the solution was added an aqueous solution (5 mL) of 85% potassium hydroxide (0.34 g, 5.15 mmol) and the mixture was stirred at room temperature for 18 hrs. The reaction solution was diluted with ethyl acetate, washed successively with aqueous citric acid solution, water and saturated brine, dried over magnesium sulfate, and concentrated under reduced pressure. The obtained residue was applied to chiral column (CHIRALPAK) chromatography (hexane:2-propanol:acetic acid=94:6:0.1) to purify each steric isomer.

3-{2-Fluoro-4-[(2'-(4-fluorophenoxymethyl)-4',6'-dimethylbiphenyl-3-yl)methoxy]phenyl}propanoic acid (657 mg, yield 64%) was obtained as a pale-yellow oil.

$^1$H NMR (CDCl$_3$) δ: 2.03(3H, s), 2.38(3H, s), 2.63(2H, t, J=7.4 Hz), 2.90(2H, t, J=7.4 Hz), 4.59(2H, s), 5.00(2H, s), 6.57-7.18(9H, m), 7.23(2H, br s), 7.30-7.44(2H, m).

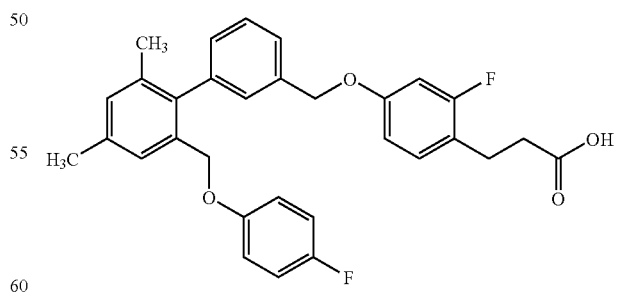

3-{2-Fluoro-4-[(4'-(4-fluorophenoxymethyl)-2',6'-dimethylbiphenyl-3-yl)methoxy]phenyl}propanoic acid (141 mg, yield 14%) was obtained as colorless prism crystals.

$^1$H NMR (CDCl$_3$) δ: 2.02(6H, s), 2.05-3.00(4H, m), 4.97 (2H, s), 5.07(2H, s), 6.62-6.72(2H, m), 6.90-7.14(7H, m), 7.16(2H, s), 7.36-7.50 (2H, m).

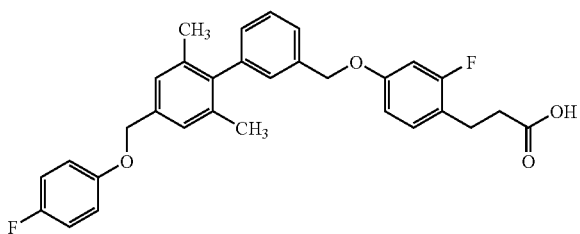

Example 56 tert-butyl 3-{4-[(4'-{[tert-butyl(dimethyl)silyl]oxy}-2',6'-dimethylbiphenyl-3-yl)methoxy]phenyl}propanoate

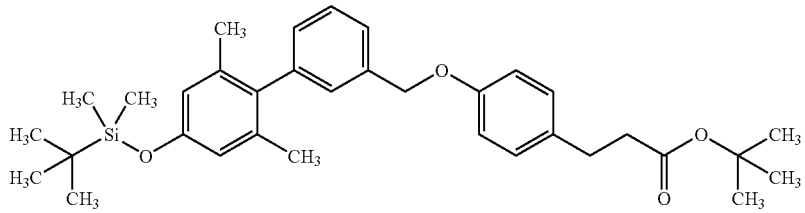

The title compound was obtained as a pale-yellow oil from (4'-{[tert-butyl(dimethyl)silyl]oxy}-2',6'-dimethylbiphenyl-3-yl)methanol and tert-butyl 3-(4-hydroxyphenyl)propanoate according to a method similar to the method of Example 1 (yield 87%).

$^1$H NMR (CDCl$_3$) δ: 0.23 (6H, s), 1.00 (9H, s), 1.41 (9H, s), 1.95 (6H, s), 2.49 (2H, t, J=7.8 Hz), 2.84 (2H, t, J=7.8 Hz), 5.07 (2H, s), 6.58 (2H, s), 6.89 (2H, d, J=8.4 Hz), 7.01-7.14 (3H, m), 7.18 (1H, s), 7.33-7.46 (2H, m).

To a solution of tert-butyl 3-{4-[(4'-{[tert-butyl(dimethyl)silyl]oxy}-2',6'-dimethylbiphenyl-3-yl)methoxy]phenyl}propanoate (2.38 g, 4.35 mmol) in tetrahydrofuran (24 mL) was added tetrabutylammonium fluoride (1 M tetrahydrofuran solution, 4.79 mmol, 4.79 mL) at room temperature with stirring and the mixture was stirred at room temperature for 2 hrs. The reaction mixture was concentrated under reduced pressure and the residue was partitioned between water and ethyl acetate. The organic layer was dried over anhydrous magnesium sulfate, and concentrated under reduced pressure. The residue was purified by silica gel column chromatography (hexane/ethyl acetate=10/1-hexane/ethyl acetate=3/1) to give the title compound (1.69 g, yield 90%) as a colorless oil.

$^1$H NMR (CDCl$_3$) δ: 1.41 (9H, s), 1.96 (6H, s), 2.50 (2H, t, J=7.8 Hz), 2.84 (2H, t, J=7.8 Hz), 5.08 (2H, s), 6.59 (2H, s), 6.89 (2H, d, J=8.7 Hz), 7.04-7.14 (3H, m), 7.18 (1H, s), 7.35-7.45 (2H, m).

Example 58 ethyl 3-[4-({4'-[2-ethoxy-1-(ethoxymethyl)ethoxy]-2',6'-dimethylbiphenyl-3-yl}methoxy)-2-fluorophenyl]propanoate

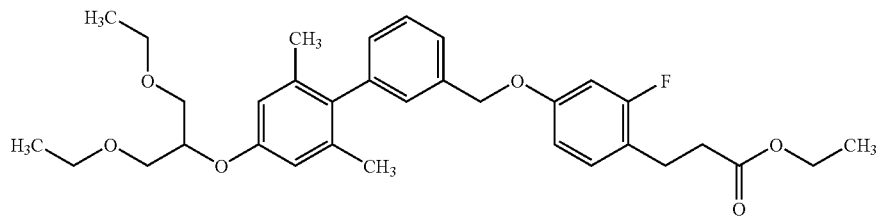

The title compound was obtained as a colorless oil from ethyl 3-{2-fluoro-4-[(4'-hydroxy-2',6'-dimethylbiphenyl-3-yl)methoxy]phenyl}propanoate and 1,3-diethoxypropan-2-ol according to a method similar to the method of Example 1 (yield 65%).

MS m/z 553 (MH$^+$)

Example 57 tert-butyl 3-{4-[(4'-hydroxy-2',6'-dimethylbiphenyl-3-yl)methoxy]phenyl}propanoate

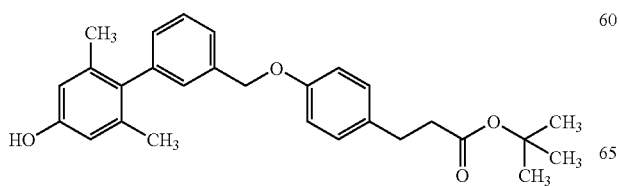

Example 59

3-[4-({4'-[2-ethoxy-1-(ethoxymethyl)ethoxy]-2',6'-dimethylbiphenyl-3-yl}methoxy)-2-fluorophenyl]propanoic acid

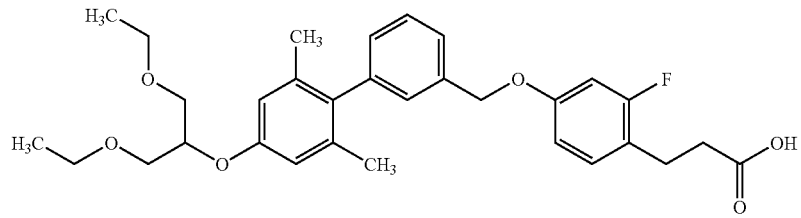

To a mixed solution of ethyl 3-[4-({4'-[2-ethoxy-1-(ethoxymethyl)ethoxy]-2',6'-dimethylbiphenyl-3-yl}methoxy)-2-fluorophenyl]propanoate (0.665 g, 1.20 mmol) in ethanol (6 mL) and tetrahydrofuran (6 mL) was added 2 M aqueous sodium hydroxide solution (2 mL) and the mixture was stirred at room temperature for 72 hrs. Water was added to the reaction mixture and the mixture was neutralized with 10% aqueous citric acid solution and extracted with ethyl acetate. The extract was washed with saturated brine, dried over anhydrous magnesium sulfate and concentrated under reduced pressure. The residue was purified by silica gel column chromatography (20%-80% ethyl acetate/hexane) to give the title compound (0.588 g, yield 93%) as a colorless viscous oil.

MS m/z 525 (MH$^+$)

Example 60

3-(4-{[4'-(2-ethoxyethoxy)-2',6'-dimethylbiphenyl-3-yl]methoxy}-2-fluorophenyl)propanamide

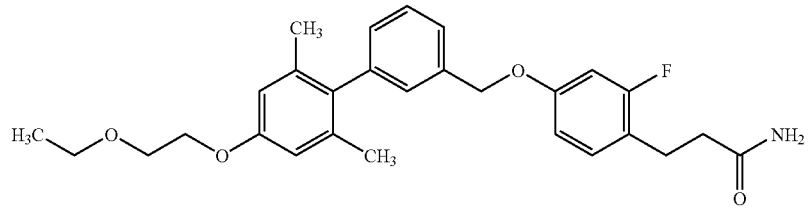

A mixture of 3-(4-{[4'-(2-ethoxyethoxy)-2',6'-dimethylbiphenyl-3-yl]methoxy}-2-fluorophenyl)propanoic acid (0.233 g, 0.500 mmol), 7 M ammonia/methanol (0.4 mL, 2.80 mmol) solution, 1-ethyl-3-(3-aminopropyl)carbodiimide hydrochloride (2.88 g, 1.50 mmol), 1-hydroxybenzotriazole (0.230 g, 1.50 mmol), 1,8-diazabicyclo[5.4.0]-7-undecene (0.448 mL, 3.00 mmol), triethylamine (0.502 mL, 3.60 mmol) and acetonitrile (3 mL) was stirred at room temperature for 27 hrs. The reaction mixture was poured into saturated aqueous sodium hydrogen carbonate solution and the mixture was extracted with ethyl acetate. The extract was washed with saturated brine, dried over anhydrous magnesium sulfate and concentrated under reduced pressure. The residue was purified by basic silica gel column chromatography (50% ethyl acetate/hexane-ethyl acetate) to give the title compound (0.186 g, yield 80%) as a colorless oil.

MS m/z 466 (MH$^+$)

Example 61

1-[3-(4-{[4'-(2-ethoxyethoxy)-2',6'-dimethylbiphenyl-3-yl]methoxy}-2-fluorophenyl)propanoyl]pyrrolidine

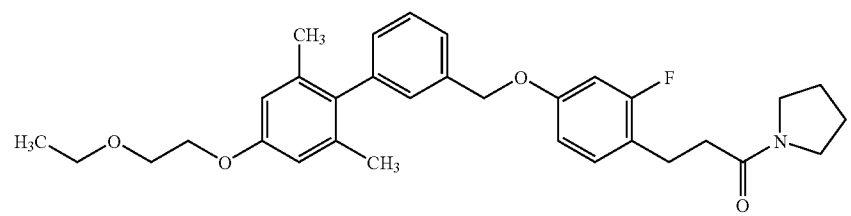

The title compound was obtained as a yellow oil from 3-(4-{[4'-(2-ethoxyethoxy)-2',6'-dimethylbiphenyl-3-yl]methoxy}-2-fluorophenyl)propanoic acid and pyrrolidine according to a method similar to the method of Example 60 (yield 95%).
MS m/z 520 (MH⁺)

Example 62

3-(4-{[4'-(methoxymethoxy)-2',6'-dimethylbiphenyl-3-yl]methoxy}phenyl)propanoic acid

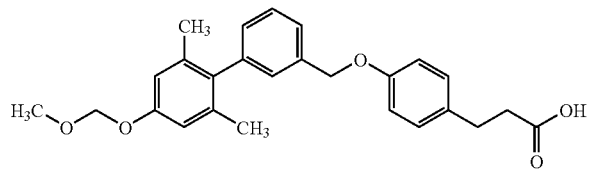

To a solution of methyl 3-{4-[(4'-hydroxy-2',6'-dimethylbiphenyl-3-yl)methoxy]phenyl}propanoate (0.50 g, 1.28 mmol), potassium carbonate (0.35 g, 2.56 mmol) and sodium iodide (0.19 g, 1.28 mmol) in N,N-dimethylformamide (5.0 mL) was added chloromethyl methyl ether (0.13 mL, 1.66 mmol) at room temperature with stirring and the mixture was stirred at 50° C. for 24 hrs. The reaction mixture was diluted with ethyl acetate, washed with water and saturated brine, dried and concentrated under reduced pressure. The residue was purified by silica gel column chromatography (hexane/ethyl acetate=10/1-hexane/ethyl acetate=3/1) to give a colorless oil. Then, to a mixture of the oil, methanol (4 mL) and tetrahydrofuran (8 mL) was added 1 N aqueousسة sodium hydroxide solution (2.6 mL) at room temperature with stirring, and the mixture was stirred at the same temperature for 2 hrs. The reaction mixture was adjusted to pH3 with 1 N hydrochloric acid, diluted with ethyl acetate, washed with saturated brine, dried and concentrated under reduced pressure. The residue was purified by silica gel column chromatography (hexane/ethyl acetate=4/1-hexane/ethyl acetate=1/2) to give the title compound (0.12 g, yield 22%) as colorless crystals.
MS (APCI–): 419 (M–H)

Example 63

3-{4-[(4'-ethoxy-2',6'-dimethylbiphenyl-3-yl)methoxy]phenyl}propanoic acid

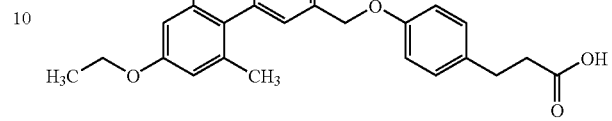

The title compound was obtained as colorless crystals from methyl 3-{4-[(4'-hydroxy-2',6'-dimethylbiphenyl-3-yl)methoxy]phenyl}propanoate and iodoethane according to a method similar to the method of Example 62 (yield 14%).
MS (APCI–): 403 (M–H)

Example 64

3-(4-{[4'-(2-butoxyethoxy)-2',6'-dimethylbiphenyl-3-yl]methoxy}phenyl)propanoic acid

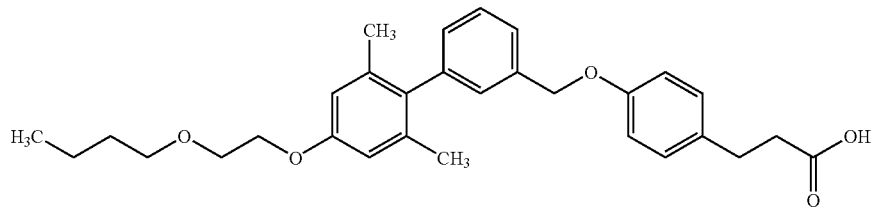

The title compound was obtained as colorless crystals from methyl 3-{4-[(4'-hydroxy-2',6'-dimethylbiphenyl-3-yl)methoxy]phenyl}propanoate and 2-chloroethyl n-butyl ether according to a method similar to the method of Example 62 (yield 66%).
MS (APCI–): 475 (M–H)

Example 65

3-[4-({4'-[2-(benzyloxy)ethoxy]-2',6'-dimethylbiphenyl-3-yl}methoxy)phenyl]propanoic acid

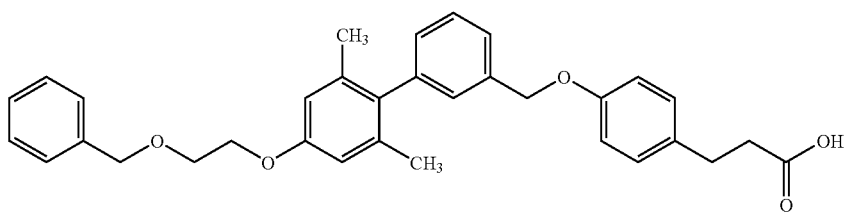

To a solution of methyl 3-{4-[(4'-hydroxy-2',6'-dimethylbiphenyl-3-yl)methoxy]phenyl}propanoate (0.50 g, 1.28 mmol), 2-(benzyloxy)ethanol (0.20 mL, 1.41 mmol) and tributylphosphine (0.48 mL, 1.92 mmol) in tetrahydrofuran (10 mL) was added 1,1'-(azodicarbonyl)dipiperidine (0.48 g, 1.92 mmol) at 0° C. with stirring. The reaction mixture was stirred at room temperature for 18 hrs., and an equivalent amount of the aforementioned reagents (2-(benzyloxy)ethanol, tributylphosphine and 1,1'-(azodicarbonyl)dipiperidine) were added at the same temperature and the mixture was further stirred for 18 hrs. Diethyl ether was added to the reaction mixture and insoluble material was filtered off. The filtrate was concentrated under reduced pressure and the residue was purified by silica gel column chromatography (hexane/ethyl acetate=10/1-hexane/ethyl acetate=2/1) to give a colorless oil. Then, to a mixture of the oil, methanol (4 mL) and tetrahydrofuran (8 mL) was added 1 N aqueous sodium hydroxide solution (2.6 mL) at room temperature with stirring, and the mixture was stirred at the same temperature for 2 hrs. The reaction mixture was neutralized with 1 N hydrochloric acid, diluted with ethyl acetate, washed with saturated brine, dried and concentrated under reduced pressure. The residue was purified by silica gel column chromatography (hexane/ethyl acetate=4/1-hexane/ethyl acetate=1/2) to give the title compound (0.26 g, yield 39%) as colorless crystals.

MS (APCI−): 509 (M−H)

Example 66

3-(4-{[2',6'-dimethyl-4'-(3-pyridin-2-ylpropoxy)biphenyl-3-yl]methoxy}phenyl)propanoic acid

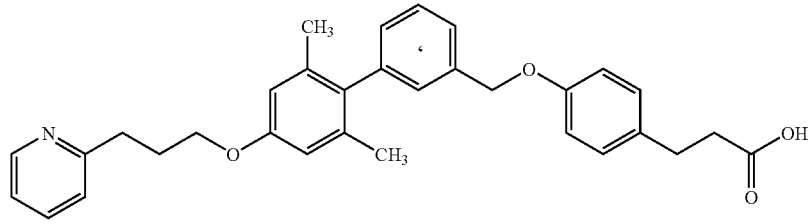

The title compound was obtained as a colorless oil from methyl 3-{4-[(4'-hydroxy-2',6'-dimethylbiphenyl-3-yl)methoxy]phenyl}propanoate and 3-(pyridin-2-yl)propan-1-ol according to a method similar to the method of Example 65 (yield 28%).

MS (APCI−): 494 (M−H)

Example 67

3-{4-[(4'-butoxy-2',6'-dimethylbiphenyl-3-yl)methoxy]phenyl}propanoic acid

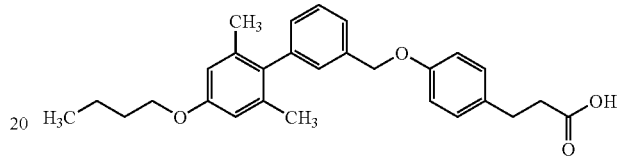

The title compound was obtained as colorless crystals from methyl 3-{4-[(4'-hydroxy-2',6'-dimethylbiphenyl-3-yl)methoxy]phenyl}propanoate and 1-butanol according to a method similar to the method of Example 65 (yield 45%).

MS (APCI−): 431 (M−H)

Example 68 methyl 3-[4-({4'-[2-(ethylthio)ethoxy]-2',6'-dimethylbiphenyl-3-yl}methoxy)phenyl]propanoate

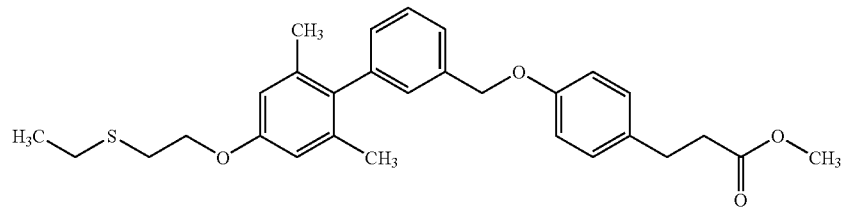

The title compound was obtained as a pale-yellow oil from methyl 3-{4-[(4'-hydroxy-2',6'-dimethylbiphenyl-3-yl)methoxy]phenyl}propanoate and 2-(ethylthio)ethanol according to a method similar to the method of Example 1 (yield 64%).

¹H NMR (CDCl₃) δ: 1.31 (3H, t, J=7.2 Hz), 1.98 (6H, s), 2.59 (2H, t, J=7.8 Hz), 2.67 (2H, q, J=7.2 Hz), 2.85-2.97 (4H, m), 3.66(3H, s), 4.15 (2H, t, J=6.9 Hz), 5.08 (2H, s), 6.66 (2H, s), 6.89 (2H, d, J=8.7 Hz), 7.04-7.14 (3H, m), 7.17 (1H, s), 7.35-7.47 (2H, m).

Example 69

3-[4-({4'-[2-(ethylthio)ethoxy]-2',6'-dimethylbiphenyl-3-yl}methoxy)phenyl]propanoic acid

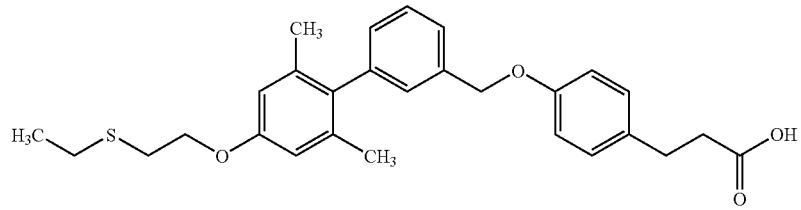

The title compound was obtained as colorless crystals from methyl 3-[4-({4'-[2-(ethylthio)ethoxy]-2',6'-dimethylbiphenyl-3-yl}methoxy)phenyl]propanoate according to a method similar to the method of Example 37 (yield 47%).

MS (APCI−): 463 (M−H).

Example 70 tert-butyl 3-[4-({4'-[2-(ethylthio)ethoxy]-2',6'-dimethylbiphenyl-3-yl}methoxy)phenyl]propanoate To a solution of tert-butyl 3-{4-[(4'-hydroxy-2',6'-dimethylbiphenyl-3-yl)methoxy]phenyl}propanoate (1.69 g, 3.91 mmol), 2-(ethylthio)ethanol (0.46 mL, 4.30 mmol) and tributylphosphine (1.46 mL, 5.86 mmol) in tetrahydrofuran (33 mL) was added 1,1'-(azodicarbonyl)dipiperidine (1.48 g, 5.86 mmol) at room temperature with stirring. The reaction mixture was stirred at room temperature for 16 hrs., and an equivalent amount of the aforementioned reagents (2-(ethylthio)ethanol, tributylphosphine and 1,1'-(azodicarbonyl)dipiperidine) were added at the same temperature and the mixture was further stirred for 16 hrs. Diethyl ether was added to the reaction mixture and insoluble material was filtered off. The filtrate was concentrated under reduced pressure and the residue was purified by silica gel column chromatography (hexane/ethyl acetate=10/1-hexane/ethyl acetate=4/1) to give the title compound (1.40 g, yield 69%) as a colorless oil.

¹H NMR (CDCl₃) δ: 1.31 (3H, t, J=7.2 Hz), 1.41 (9H, s), 1.99 (6H, s), 2.49 (2H, t, J=7.8 Hz), 2.67 (2H, q, J=7.2 Hz), 2.84 (2H, t, J=7.8 Hz), 2.92 (2H, t, J=6.9 Hz), 4.15 (2H, t, J=6.9 Hz), 5.08 (2H, s), 6.66 (2H, s), 6.89 (2H, d, J=8.7 Hz), 7.05-7.14 (3H, m), 7.18 (1H, s), 7.35-7.45 (2H, m).

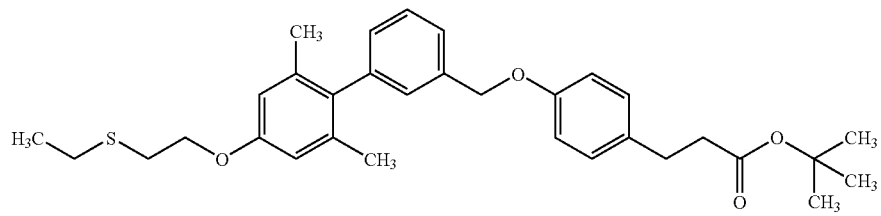

Example 71 tert-butyl 3-[4-({4'-[2-(ethylsulfonyl)ethoxy]-2',6'-dimethylbiphenyl-3-yl}methoxy)phenyl]propanoate

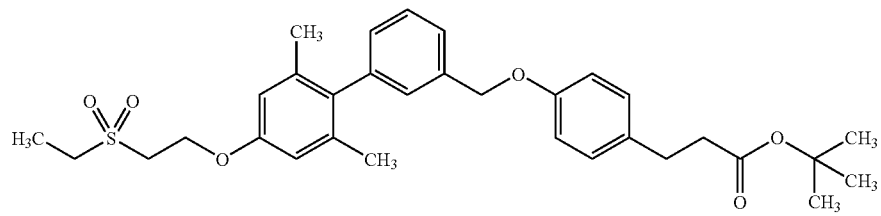

To a solution of tert-butyl 3-[4-({4'-[2-(ethylthio)ethoxy]-2',6'-dimethylbiphenyl-3-yl}methoxy)phenyl]propanoate (0.70 g, 1.34 mmol) in dichloromethane (14 mL) was added m-chloroperbenzoic acid (0.73 g, 2.96 mmol) at 0° C. with stirring and the mixture was stirred at the same temperature for 2 hrs. The reaction mixture was washed with 1 N aqueous sodium hydroxide solution and saturated brine, dried over anhydrous magnesium sulfate and concentrated under reduced pressure. The residue was purified by silica gel column chromatography (hexane/ethyl acetate=10/1-hexane/ethyl acetate=1/1) to give the title compound (0.67 g, yield 74%) as a pale-yellow oil.

$^1$H NMR (CDCl$_3$) δ: 1.41 (9H, s), 1.47 (3H, t, J=7.5 Hz), 1.99 (6H, s), 2.49 (2H, t, J=7.8 Hz), 2.84 (2H, t, J=7.8 Hz), 3.19 (2H, q, J=7.5 Hz), 3.42 (2H, t, J=5.1 Hz), 4.44 (2H, t, J=5.1 Hz), 5.08 (2H, s), 6.64 (2H, s), 6.88 (2H, d, J=8.7 Hz), 7.03-7.14 (3H, m), 7.17 (1H, s), 7.36-7.48 (2H, m).

Example 72

3-[4-({4'-[2-(ethylsulfonyl)ethoxy]-2',6'-dimethylbiphenyl-3-yl}methoxy)phenyl]propanoic acid

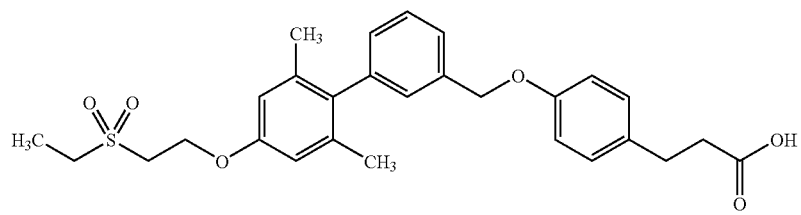

To a solution of tert-butyl 3-[4-({4'-[2-(ethylsulfonyl)ethoxy]-2',6'-dimethylbiphenyl-3-yl}methoxy)phenyl]propanoate (0.37 g, 0.67 mmol) in toluene (3.7 mL) was added trifluoroacetic acid (3.7 mL) at room temperature with stirring and the mixture was stirred at room temperature for 2 hrs. The reaction mixture was concentrated under reduced pressure, the obtained crystals were collected by filtration, washed and dried to give the title compound (0.24 g, yield 72%) as colorless crystals.

MS (APCI−): 495 (M−H)

Example 73

3-[4-({2',6'-dimethyl-4'-[3-(6-methylpyridin-2-yl)propoxy]biphenyl-3-yl}methoxy)phenyl]propanoic acid

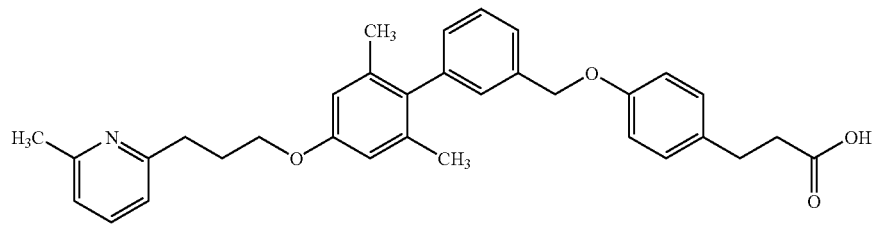

The title compound was obtained as a pale-yellow oil from methyl 3-{4-[(4'-hydroxy-2',6'-dimethylbiphenyl-3-yl)methoxy]phenyl}propanoate and 3-(6-methylpyridin-2-yl)propan-1-ol according to a method similar to the method of Example 65 (yield 17%).

MS (APCI−): 508 (M−H)

Example 74 ethyl 3-(4-{[4'-(2-ethoxyethoxy)-2',6'-dimethylbiphenyl-3-yl]methoxy}phenyl)-2,2-difluoropropanoate

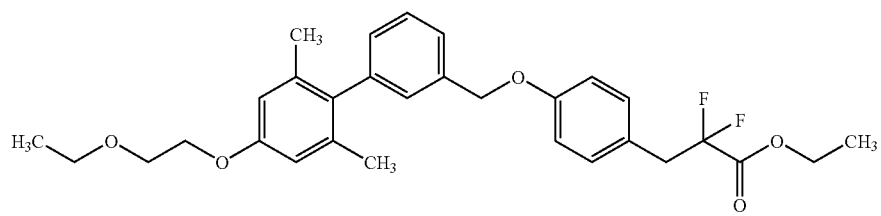

The title compound was obtained as a colorless oil from ethyl 2,2-difluoro-3-(4-hydroxyphenyl)propanoate and [4'-(2-ethoxyethoxy)-2',6'-dimethylbiphenyl-3-yl]methanol according to a method similar to the method of Example 1 (yield 51%).
MS m/z 513(MH$^+$)

Example 75

3-(4-{[4'-(2-ethoxyethoxy)-2',6'-dimethylbiphenyl-3-yl]methoxy}phenyl)-2,2-difluoropropanoic acid

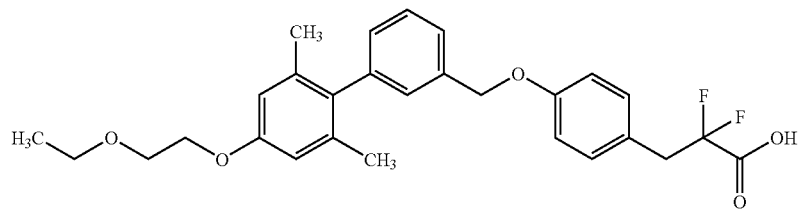

The title compound was obtained as a colorless oil from ethyl 3-(4-{[4'-(2-ethoxyethoxy)-2',6'-dimethylbiphenyl-3-yl]methoxy}phenyl)-2,2-difluoropropanoate according to a method similar to the method of Example 2 (yield 79%).
MS m/z 485(MH$^+$)
$^1$H NMR (CDCl$_3$) δ: 1.21-1.30(3H, m), 1.95(6H, s), 3.25 (2H, t, J=16.7 Hz), 3.63(2H, q, J=7.0 Hz), 3.77-3.85(2H, m), 4.07-4.19(2H, m), 5.02(2H, s), 6.66(2H, s), 6.87(2H, d, J=8.5 Hz), 7.02-7.20(4H, m), 7.30-7.43(2H, m).

Example 76 methyl 3-(4-{[2',6'-dimethyl-4'-(tetrahydro-2H-thiopyran-4-yloxy)biphenyl-3-yl]methoxy}phenyl)propanoate

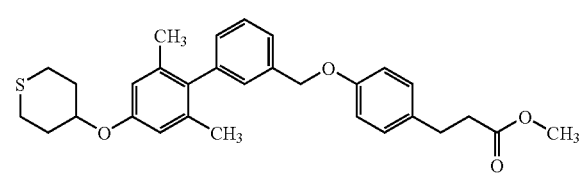

The title compound was obtained as a colorless oil from methyl 3-{4-[(4'-hydroxy-2',6'-dimethylbiphenyl-3-yl)methoxy]phenyl}propanoate and tetrahydro-2H-thiopyran-4-ol according to a method similar to the method of Example 1 (yield 12%).
$^1$H NMR (CDCl$_3$) δ: 1.98 (6H, s), 1.99-2.11(2H, m), 2.15-2.27 (2H, m), 2.53-2.65 (4H, m), 2.84-3.01 (4H, m), 3.66 (3H, s), 4.37 (1H, m), 5.08 (2H, s), 6.65 (2H, s), 6.89 (2H, d, J=8.7 Hz), 7.05-7.14 (3H, m), 7.18 (1H, s), 7.35-7.46 (2H, m).

Example 77

3-(4-{[2',6'-dimethyl-4'-(tetrahydro-2H-thiopyran-4-yloxy)biphenyl-3-yl]methoxy}phenyl)propanoic acid

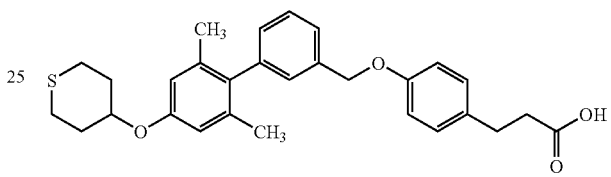

The title compound was obtained as colorless crystals from methyl 3-(4-{[2',6'-dimethyl-4'-(tetrahydro-2H-thiopyran-4-yloxy)biphenyl-3-yl]methoxy}phenyl)propanoate according to a method similar to the method of Example 37 (yield 55%).
MS (ESI+): 477 (M+H)

Example 78

3-[4-({4'-[(1,1-dioxidotetrahydro-2H-thiopyran-4-yl)oxy]-2',6'-dimethylbiphenyl-3-yl}methoxy)phenyl]propanoic acid

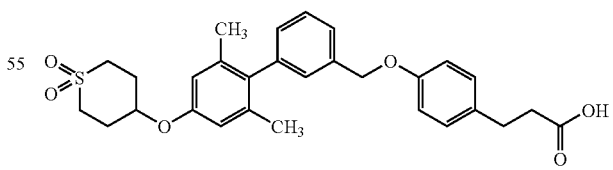

To a solution of methyl 3-(4-{[2',6'-dimethyl-4'-(tetrahydro-2H-thiopyran-4-yloxy)biphenyl-3-yl]methoxy}phenyl)propanoate (0.11 g, 0.22 mmol) in dichloromethane (2.2 mL) was added m-chloroperbenzoic acid (0.12 g, 0.49 mmol) at 0° C. with stirring and the mixture was stirred at the same temperature for 2 hrs. The reaction mixture was washed with 1 N aqueous sodium hydroxide solution and saturated brine, dried over anhydrous magnesium sulfate and concentrated under reduced pressure. To a mixture of the residue, methanol (2 mL) and tetrahydrofuran (4 mL) was added 1 N aqueous sodium hydroxide solution (0.44 mL) at room temperature with stirring and the mixture was stirred at the same temperature for 2 hrs. The reaction mixture was diluted with ethyl acetate, washed with 1 N hydrochloric acid and saturated brine, dried and concentrated under reduced pressure. The residue was purified by silica gel column chromatography (hexane/ethyl acetate=10/1-hexane/ethyl acetate=1/1) to give the title compound (43 mg, yield 38%) as colorless crystals.

MS (ESI+): 509 (M+H).

Example 79

3-[4-({2',6'-dimethyl-4'-[3-(6-methylpyridin-2-yl) propoxy]biphenyl-3-yl}methoxy)phenyl]propanoic acid hydrochloride To a solution of methyl 3-{4-[(4'-hydroxy-2',6'-dimethyl-biphenyl-3-yl)methoxy]phenyl}propanoate (0.40 g, 1.03 mmol), (6-methylpyridin-2-yl)methanol (0.14 g, 1.13 mmol) and triphenylphosphine (0.34 g, 1.31 mmol) in tetrahydrofuran (8.0 mL) was added diisopropyl azodicarboxylate (40% toluene solution, 0.59 mL, 1.13 mmol) at room temperature with stirring. The reaction mixture was stirred at room temperature for 12 hrs., and an equivalent amount of the aforementioned reagents ((6-methylpyridin-2-yl)methanol, triphenylphosphine and diisopropyl azodicarboxylate) were added and the mixture was further stirred at the same temperature for 12 hrs. The reaction mixture was concentrated under reduced pressure and the residue was purified by silica gel column chromatography (hexane/ethyl acetate=10/1-hexane/ethyl acetate=1/1) to give a colorless oil. Then, to a mixture of the oil, methanol (4 mL) and tetrahydrofuran (8 mL) was added 1 N aqueous sodium hydroxide solution (2.1

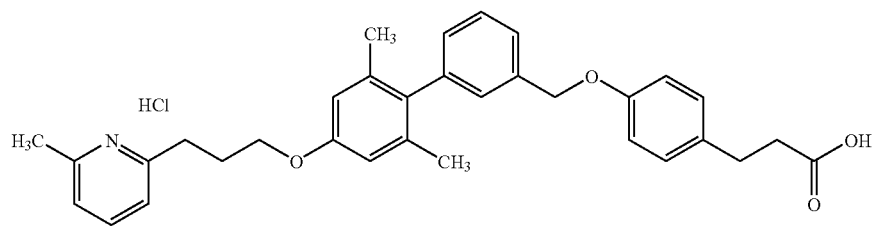

To a solution of 3-[4-({2',6'-dimethyl-4'-[3-(6-methylpyridin-2-yl)propoxy]biphenyl-3-yl}methoxy)phenyl]propanoic acid (55 mg, 0.11 mmol) in ethyl acetate (2.2 mL) was added 4 N hydrogen chloride-ethyl acetate solution (81 μL, 0.32 mmol) and the mixture was concentrated under reduced pressure. The obtained crystals were collected by filtration, washed and dried to give the title compound (42 mg, yield 71%) as colorless crystals.

MS (ESI+): 510 (M+H, as a free form)

Example 80

3-[4-({2',6'-dimethyl-4'-[(6-methylpyridin-2-yl) methoxy]biphenyl-3-yl}methoxy)phenyl]propanoic acid hydrochloride mL) at room temperature with stirring and the mixture was stirred at the same temperature for 2 hrs. The reaction mixture was neutralized with 1 N hydrochloric acid, diluted with ethyl acetate, washed with saturated brine, dried and concentrated under reduced pressure. The residue was purified by silica gel column chromatography (hexane/ethyl acetate=10/1-hexane/ethyl acetate=1/4) to give a colorless oil. The oil was dissolved in ethyl acetate and 4 N hydrogen chloride-ethyl acetate solution was added. The mixture was concentrated under reduced pressure. The obtained crystals were collected by filtration, washed and dried to give the title compound (0.24 g, yield 44%) as colorless crystals.

MS (APCI−): 480 (M−H, as a free form)

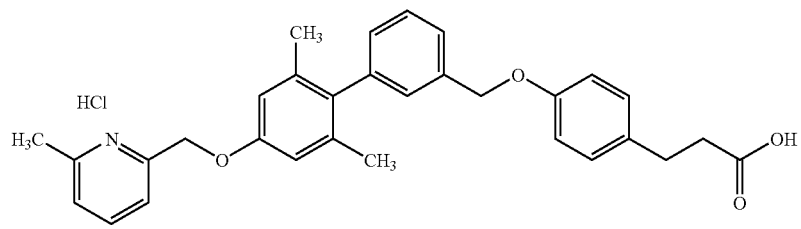

Example 81

3-[4-({2',6'-dimethyl-4'-[2-(6-methylpyridin-2-yl)ethoxy]biphenyl-3-yl}methoxy)phenyl]propanoic acid hydrochloride

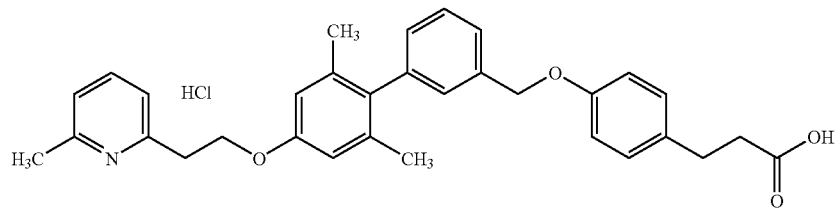

The title compound was obtained as colorless crystals from methyl 3-[4-[(4'-hydroxy-2',6'-dimethylbiphenyl-3-yl)methoxy]phenyl]propanoate and 2-(6-methylpyridin-2-yl)ethanol according to a method similar to the method of Example 80 (yield 26%).
MS (APCI−): 494 (M−H, as a free form)

Example 82 ethyl 3-{4-[(2',6'-dimethyl-4'-nitrobiphenyl-3-yl)methoxy]-2-fluorophenyl}propanoate

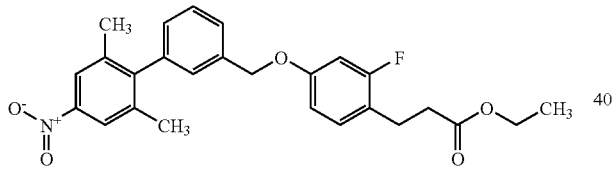

The title compound was obtained as a pale-yellow oil from (2',6'-dimethyl-4'-nitrobiphenyl-3-yl)methanol and ethyl 3-(2-fluoro-4-hydroxyphenyl)propanoate according to a method similar to the method of Example 1 (yield 97%).

MS (ESI+): 452 (M+H)

Example 83

3-{4-[(2',6'-dimethyl-4'-nitrobiphenyl-3-yl)methoxy]-2-fluorophenyl}propanoic acid The title compound was obtained as colorless crystals from ethyl 3-{4-[(2',6'-dimethyl-4'-nitrobiphenyl-3-yl)methoxy]-2-fluorophenyl}propanoate according to a method similar to the method of Example 37 (yield 84%).
MS (APCI−): 422 (M−H)

Example 84 ethyl 3-[4-({4'-[2-(ethylthio)ethoxy]-2',6'-dimethylbiphenyl-3-yl}methoxy)-2-fluorophenyl]propanoate

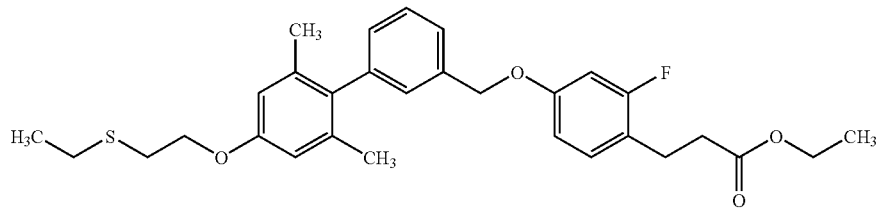

The title compound was obtained as a colorless oil from ethyl 3-{2-fluoro-4-[(4'-hydroxy-2',6'-dimethylbiphenyl-3-yl)methoxy]phenyl}propanoate and 2-(ethylthio)ethanol according to a method similar to the method of Example 70 (yield 79%).
$^1$H NMR (CDCl$_3$) δ: 1.23 (3H, t, J=7.2 Hz), 1.31 (3H, t, J=7.5 Hz), 1.98 (6H, s), 2.57 (2H, t, J=7.8 Hz), 2.67 (2H, q, J=7.5 Hz), 2.86-2.96 (4H, m), 4.07-4.19 (4H, m), 5.06 (2H, s), 6.62-6.71 (4H, m), 7.04-7.13 (2H, m), 7.16 (1H, s), 7.33-7.47 (2H, m).

Example 85 ethyl 3-[4-({4'-[2-(ethylsulfonyl)ethoxy]-2',6'-dimethylbiphenyl-3-yl}methoxy)-2-fluorophenyl]propanoate

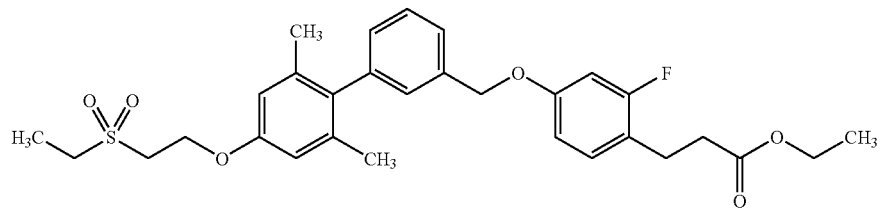

The title compound was obtained as a colorless oil from ethyl 3-[4-({4'-[2-(ethylthio)ethoxy]-2',6'-dimethylbiphenyl-3-yl}methoxy)-2-fluorophenyl]propanoate according to a method similar to the method of Example 71 (yield 89%).

MS (ESI+): 543 (M+H)

Example 86

3-[4-({4'-[2-(ethylsulfonyl)ethoxy]-2',6'-dimethylbiphenyl-3-yl}methoxy)-2-fluorophenyl]propanoic acid

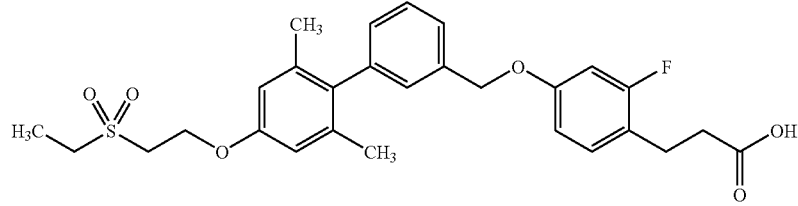

A mixture of ethyl 3-[4-({4'-[2-(ethylsulfonyl)ethoxy]-2',6'-dimethylbiphenyl-3-yl}methoxy)-2-fluorophenyl]propanoate (0.19 g, 0.35 mmol), acetic acid (4.5 mL), water (4.0 mL) and conc. sulfuric acid (0.65 mL) was stirred at 90° C. for 4 hrs. The reaction mixture was cooled, diluted with ethyl acetate, washed with water and saturated brine, dried and concentrated under reduced pressure. The residue was purified by silica gel column chromatography (hexane/ethyl acetate=4/1-ethyl acetate) to give the title compound (0.12 g, yield 61%) as colorless crystals.

MS (APCI−): 513 (M−H)
m.p.: 126-127° C.

Example 87 ethyl 3-[4-({4'-[2-(diethylamino)ethoxy]-2',6'-dimethylbiphenyl-3-yl}methoxy)-2-fluorophenyl]propanoate

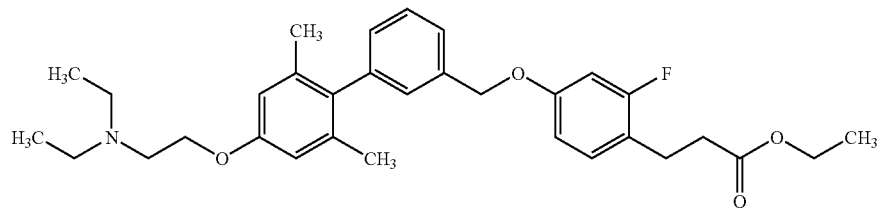

The title compound was obtained as a colorless oil from ethyl 3-{2-fluoro-4-[(4'-hydroxy-2',6'-dimethylbiphenyl-3-yl)methoxy]phenyl}propanoate and 2-(diethylamino)ethanol according to a method similar to the method of Example 70 (yield 100%).

MS (ESI+): 522 (M+H)

Example 88

3-[4-({4'-[2-(diethylamino)ethoxy]-2',6'-dimethylbiphenyl-3-yl}methoxy)-2-fluorophenyl]propanoic acid hydrochloride

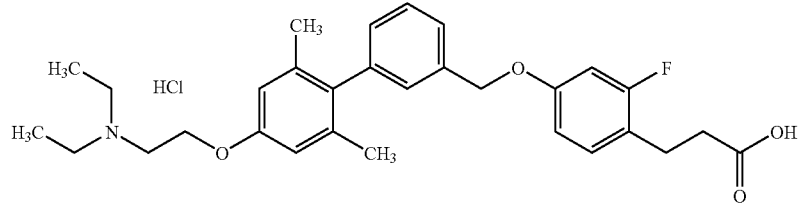

To a mixture of ethyl 3-[4-({4'-[2-(diethylamino)ethoxy]-2',6'-dimethylbiphenyl-3-yl}methoxy)-2-fluorophenyl]propanoate (0.62 g, 1.18 mmol), methanol (5 mL) and tetrahydrofuran (10 mL) was added 1 N aqueous sodium hydroxide solution (2.4 mL) at room temperature with stirring and the mixture was stirred at the same temperature for 2 hrs. The reaction mixture was neutralized with 1 N hydrochloric acid, diluted with ethyl acetate, washed with saturated brine, dried and concentrated under reduced pressure. The residue was purified by preparative HPLC to give a colorless oil. The oil was dissolved in ethyl acetate, neutralized with saturated aqueous sodium hydrogen carbonate, washed with water and saturated brine, dried and concentrated under reduced pressure. The residue was dissolved in ethyl acetate and 4 N hydrogen chloride-ethyl acetate solution was added. The precipitated crystals were collected by filtration, washed and dried to give the title compound (0.20 g, yield 32%) as colorless crystals.

MS (ESI+): 494 (M+H, as a free form)

Example 89 ethyl 3-[4-({2',6'-dimethyl-4'-[3-(2-oxopyrrolidin-1-yl)propoxy]biphenyl-3-yl}methoxy)-2-fluorophenyl]propanoate

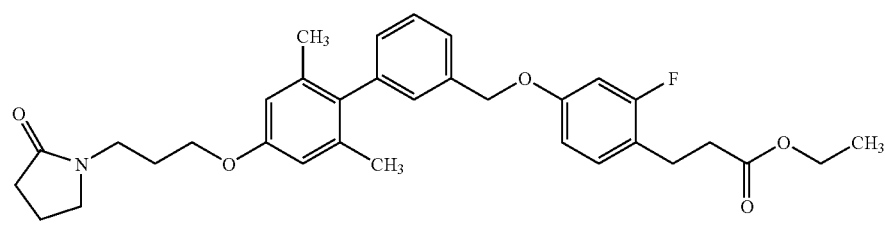

The title compound was obtained as a colorless oil from ethyl 3-{2-fluoro-4-[(4'-hydroxy-2',6'-dimethylbiphenyl-3- yl)methoxy]phenyl}propanoate and 1-(3-hydroxypropyl) pyrrolidin-2-one according to a method similar to the method of Example 1 (yield 67%).
MS (ESI+): 548 (M+H)

Example 90

3-[4-({2',6'-dimethyl-4'-[3-(2-oxopyrrolidin-1-yl) propoxy]biphenyl-3-yl}methoxy)-2-fluorophenyl] propanoic acid

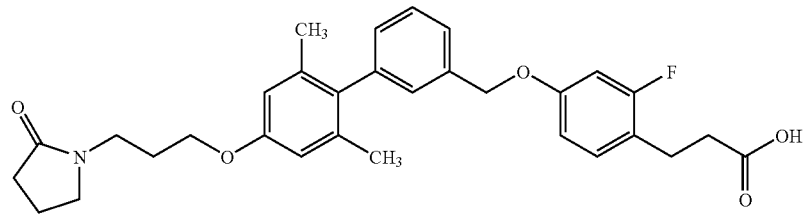

The title compound was obtained as colorless crystals from ethyl 3-[4-({2',6'-dimethyl-4'-[3-(2-oxopyrrolidin-1-yl)propoxy]biphenyl-3-yl}methoxy)-2-fluorophenyl]propanoate according to a method similar to the method of Example 37 (yield 64%). This compound was purified by preparative HPLC (gradient cycle A).
MS (ESI+): 520 (M+H).
m.p.: 139-140° C.

Example 91 ethyl 3-(2-fluoro-4-{[4'-(methoxymethoxy)-2',6'-dimethylbiphenyl-3-yl]methoxy}phenyl)propanoate

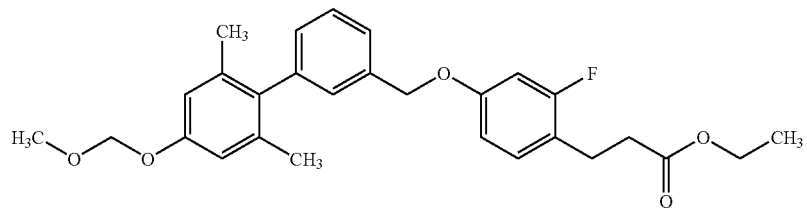

The title compound was obtained as a colorless oil from [4'-(methoxymethoxy)-2',6'-dimethylbiphenyl-3-yl]methanol and ethyl 3-(2-fluoro-4-hydroxyphenyl)propanoate according to a method similar to the method of Example 1 (yield 82%).

$^1$H NMR (CDCl$_3$) δ: 1.23(3H, t, J=7.2 Hz), 1.99(6H, s), 2.57(2H, t, J=7.6 Hz), 2.90(2H, t, J=7.6 Hz), 3.51(3H, s), 4.12(2H, q, J=7.2 Hz), 5.06(2H, s), 5.19(2H, s), 6.60-6.75 (2H, m), 6.80(2H, 20 s), 7.02-7.50(5H, m).

Example 92

3-(2-fluoro-4-{[4'-(methoxymethoxy)-2',6'-dimethylbiphenyl-3-yl]methoxy}phenyl)propanoic acid The title compound was obtained as colorless needle crystals from ethyl 3-(2-fluoro-4-{[4'-(methoxymethoxy)-2',6'-dimethylbiphenyl-3-yl]methoxy}phenyl)propanoate according to a method similar to the method of Example 2 (yield 88%).

MS m/z 437 (MH+)

Example 93 ethyl 3-[4-({4'-[2-(ethylamino)ethoxy]-2',6'-dimethylbiphenyl-3-yl}methoxy)-2-fluorophenyl]propanoate

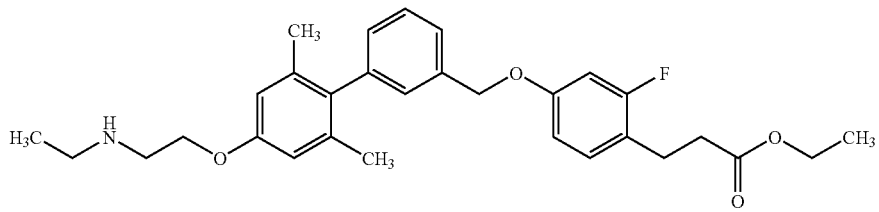

To a solution of ethyl 3-{2-fluoro-4-[(4'-hydroxy-2',6'-dimethylbiphenyl-3-yl)methoxy]phenyl}propanoate (0.50 g, 1.18 mmol), 2-ethylaminoethanol (0.10 mL, 1.30 mmol) and tributylphosphine (0.44 mL, 1.78 mmol) in tetrahydrofuran (10 mL) was added 1,1'-(azodicarbonyl)dipiperidine (0.45 g, 1.78 mmol) at room temperature with stirring. The reaction mixture was stirred at room temperature for 16 hrs. An equivalent amount of the aforementioned reagents (2-ethylaminoethanol, tributylphosphine and 1,1'-(azodicarbonyl)dipiperidine) were added and the mixture was further stirred at the same temperature for 16 hrs. Diethyl ether was added to the reaction mixture and insoluble material was filtered off. The filtrate was concentrated under reduced pressure and the residue was purified by preparative HPLC (gradient cycle A) to give a colorless oil. The obtained oil was dissolved in ethyl acetate, neutralized with saturated aqueous sodium hydrogen carbonate, washed with water and saturated brine, dried and concentrated under reduced pressure to give the title compound (0.52 g, yield 58%) as a colorless oil.

MS (ESI+): 494 (M+H)

Example 94 ethyl 3-{4-[(4'-{2-[acetyl(ethyl)amino]ethoxy}-2',6'-dimethylbiphenyl-3-yl)methoxy]-2-fluorophenyl}propanoate

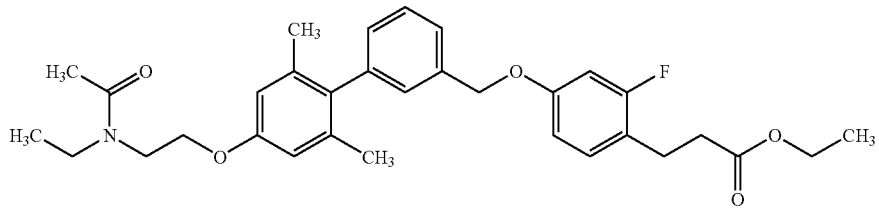

A mixture of ethyl 3-[4-({4'-[2-(ethylamino)ethoxy]-2',6'-dimethylbiphenyl-3-yl}methoxy)-2-fluorophenyl]propanoate (0.27 g, 0.55 mmol), 4-dimethylaminopyridine (7 mg, 55 μmol), acetic anhydride (0.10 mL, 1.09 mmol) and pyridine (5.4 mL) was stirred at room temperature for 62 hrs. The reaction mixture was concentrated and the residue was purified by silica gel column chromatography (hexane/ethyl acetate=9/1-ethyl acetate) to give the title compound (0.25 g, yield 85%) as a colorless oil.

MS (ESI+): 536 (M+H)

Example 95

3-{4-[(4'-{2-[acetyl(ethyl)amino]ethoxy}-2',6'-dimethylbiphenyl-3-yl)methoxy]-2-fluorophenyl}propanoic acid

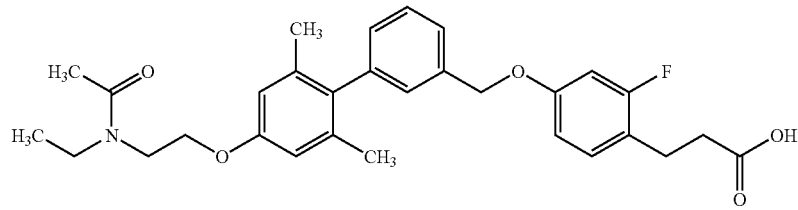

The title compound was obtained as colorless crystals from ethyl 3-{4-[(4'-{2-[acetyl(ethyl)amino]ethoxy}-2',6'-dimethylbiphenyl-3-yl)methoxy]-2-fluorophenyl}propanoate according to a method similar to the method of Example 37 (yield 51%).

MS (ESI+): 508 (M+H)

Example 96 ethyl 3-[4-({2',6'-dimethyl-4'-[(6-methylpyridin-2-yl)methoxy]biphenyl-3-yl}methoxy)-2-fluorophenyl]propanoate

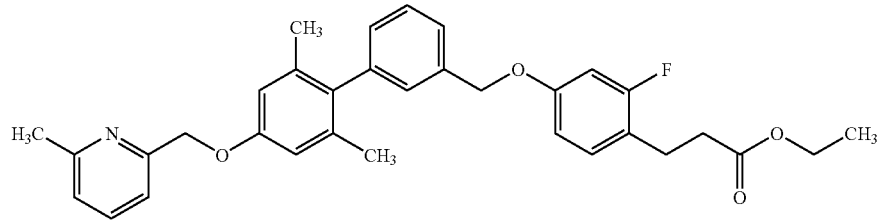

To a solution of ethyl 3-{2-fluoro-4-[(4'-hydroxy-2',6'-dimethylbiphenyl-3-yl)methoxy]phenyl}propanoate (1.2 g, 2.84 mmol), (6-methylpyridin-2-yl)methanol (0.39 g, 3.12 mmol) and triphenylphosphine (0.95 g, 3.61 mmol) in tetrahydrofuran (24 mL) was added diisopropyl azodicarboxylate (40% toluene solution, 1.54 mL, 3.12 mmol) at room temperature with stirring. The reaction mixture was stirred at room temperature for 12 hrs., and an equivalent amount of the aforementioned reagents ((6-methylpyridin-2-yl)methanol, triphenylphosphine and diisopropyl azodicarboxylate) were added. The mixture was further stirred at the same temperature for 12 hrs. The reaction mixture was concentrated under reduced pressure and the residue was purified by silica gel column chromatography (hexane/ethyl acetate=10/1-hexane/ethyl acetate=1/1) to give the title compound (1.3 g, yield 87%) as a colorless oil.

MS (ESI+): 528 (M+H)

Example 97

3-[4-({2',6'-dimethyl-4'-[(6-methylpyridin-2-yl)methoxy]biphenyl-3-yl}methoxy)-2-fluorophenyl]propanoic acid hydrochloride

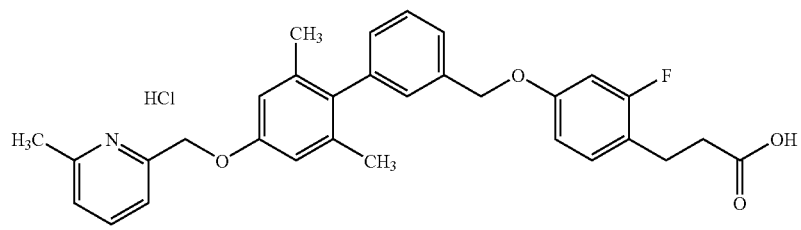

To a mixture of ethyl 3-[4-({2',6'-dimethyl-4'-[(6-methylpyridin-2-yl)methoxy]biphenyl-3-yl}methoxy)-2-fluorophenyl]propanoate (1.30 g, 2.46 mmol), methanol (6 mL) and tetrahydrofuran (10 mL) was added 1 N sodium hydroxide aqueous solution (4.9 mL) at room temperature with stirring, and the mixture was stirred at the same temperature for 2 hrs. The reaction mixture was neutralized with 1 N hydrochloric acid, diluted with ethyl acetate, washed with saturated brine, dried and concentrated under reduced pressure. The residue was purified by silica gel column chromatography (hexane/ethyl acetate=4/1-ethyl acetate) to give an oil. The oil was dissolved in ethyl acetate and 4 N hydrogen chloride-ethyl acetate solution was added. The precipitated crystals were collected by filtration, washed and dried to give the title compound (1.14 g, yield 86%) as colorless crystals.

MS (ESI+): 500 (M+H, as a free form). m.p.: 55-56° C.

Example 98 ethyl 3-[2-fluoro-4-({4'-[(4-hydroxytetrahydro-2H-thiopyran-4-yl)methoxy]-2',6'-dimethylbiphenyl-3-yl}methoxy)phenyl]propanoate

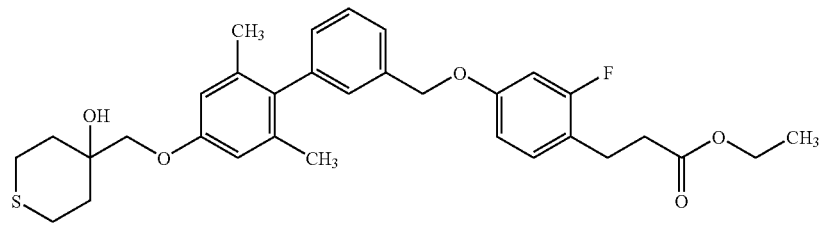

To a solution of 4-({[3'-(hydroxymethyl)-2,6-dimethylbiphenyl-4-yl]oxy}methyl)tetrahydro-2H-thiopyran-4-ol (0.90 g, 2.51 mmol), ethyl 3-(2-fluoro-4-hydroxyphenyl)propanoate (0.56 g, 2.64 mmol) and tributylphosphine (0.86 mL, 3.26 mmol) in tetrahydrofuran (20 mL) was added 1,1'-(azodicarbonyl)dipiperidine (0.85 g, 3.26 mmol) at room temperature with stirring, and the mixture was stirred for 10 hrs. The resulting precipitate was filtered off and the filtrate was concentrated under reduced pressure. The residue was purified by silica gel column chromatography (hexane/ethyl acetate=10/1-hexane/ethyl acetate=2/1) to give the title compound (1.24 g, yield 89%) as a colorless oil.

$^1$H NMR (CDCl$_3$) δ: 1.23(3H, t, J=7.2 Hz), 1.75-1.90(2H, m), 1.99(6H, s), 2.05-2.16(2H, m, J=13.9 Hz), 2.19(1H, s), 2.39-2.52(2H, m), 2.57(2H, t, J=7.6 Hz), 2.89(2H, t, J=7.6 Hz), 3.03-3.19(2H, m), 3.79(2H, s), 4.12(2H, q, J=7.2 Hz), 5.06(2H, s), 6.60-6.73(4H, m), 7.01-7.19(3H, m), 7.33-7.48 (2H, m).

Example 99 ethyl 3-[2-fluoro-4-({4'-[(4-hydroxy-1,1-dioxidotetrahydro-2H-thiopyran-4-yl)methoxy]-2',6'-dimethylbiphenyl-3-yl}methoxy)phenyl]propanoate

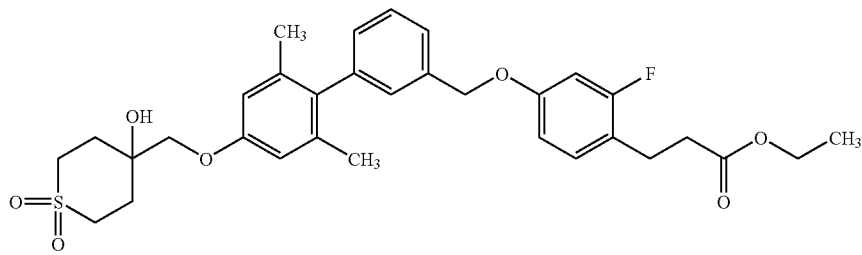

The title compound was obtained as colorless crystals from ethyl 3-[2-fluoro-4-({4'-[(4-hydroxytetrahydro-2H-thiopyran-4-yl)methoxy]-2',6'-dimethylbiphenyl-3-yl}methoxy)phenyl]propanoate according to a method similar to the method of Example 71 (yield 72%).

MS m/z 585 (MH$^+$)

Example 100

3-[2-fluoro-4-({4'-[(4-hydroxy-1,1-dioxidotetrahydro-2H-thiopyran-4-yl)methoxy]-2',6'-dimethylbiphenyl-3-yl}methoxy)phenyl]propanoic acid

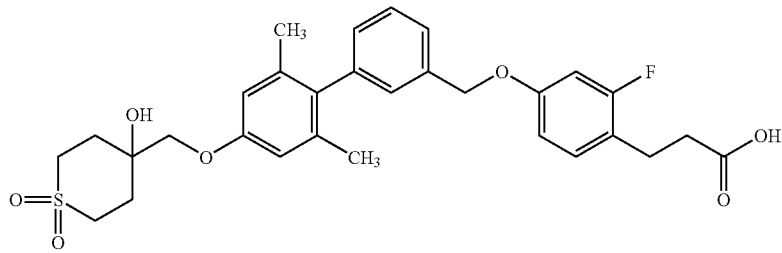

The title compound was obtained as colorless crystals from ethyl 3-[2-fluoro-4-({4'-[(4-hydroxy-1,1-dioxidotetrahydro-2H-thiopyran-4-yl)methoxy]-2',6'-dimethylbiphenyl-3-yl}methoxy)phenyl]propanoate according to a method similar to the method of Example 37 (yield 78%).

MS m/z 557 (MH$^+$).
m.p.: 198-199° C.

Example 101 ethyl 3-[4-({2',6'-dimethyl-4'-[(methylsulfonyl)oxy]biphenyl-3-yl}methoxy)-2-fluorophenyl]propanoate

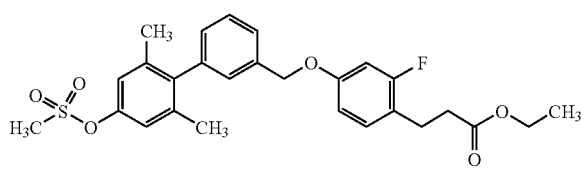

To an ice-cooled solution of ethyl 3-{2-fluoro-4-[(4'-hydroxy-2',6'-dimethylbiphenyl-3-yl)methoxy]phenyl}propanoate (310 mg, 0.736 mmol) in pyridine (8 mL) was added dropwise methanesulfonyl chloride (168 mg, 1.47 mmol). The mixture was stirred at room temperature for 2 days. Water was added, and the mixture was extracted with ethyl acetate. The extract was washed with saturated brine, dried over anhydrous magnesium sulfate and concentrated under reduced pressure. The residue was purified by silica gel column chromatography (hexane/ethyl acetate=10/1-1/1) to give the title compound (320 mg, yield 87%) as a colorless oil.

MS m/z 501(MH$^+$)

Example 102

3-[4-({2',6'-dimethyl-4'-[(methylsulfonyl)oxy]biphenyl-3-yl}methoxy)-2-fluorophenyl]propanoic acid

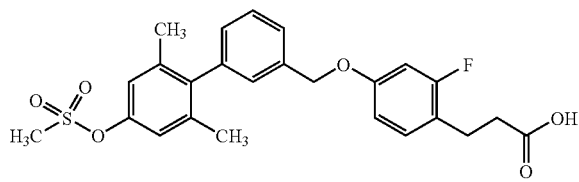

The title compound was obtained as a colorless oil from ethyl 3-[4-({2',6'-dimethyl-4'-[(methylsulfonyl)oxy]biphenyl-3-yl}methoxy)-2-fluorophenyl]propanoate according to a method similar to the method of Example 2 (yield 61%).

MS m/z 473(MH$^+$).
m.p.: 124-125° C.

Example 103 ethyl 3-[4-({2',6'-dimethyl-4'-[(3-thienylsulfonyl)oxy]biphenyl-3-yl}methoxy)-2-fluorophenyl]propanoate

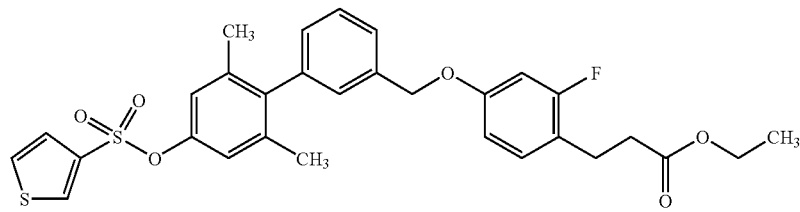

The title compound was obtained as a colorless oil from ethyl 3-{2-fluoro-4-[(4'-hydroxy-2',6'-dimethylbiphenyl-3-yl)methoxy]phenyl}propanoate and 3-thiophenesulfonyl chloride according to a method similar to the method of Example 101 (yield 57%).

MS m/z 569(MH$^+$)

Example 104

3-[4-({2',6'-dimethyl-4'-[(3-thienylsulfonyl)oxy]biphenyl-3-yl}methoxy)-2-fluorophenyl]propanoic acid

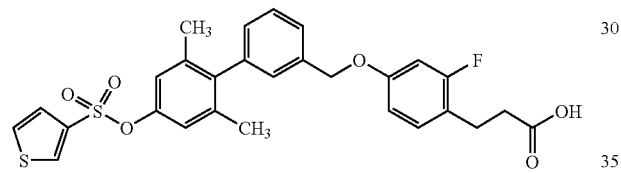

The title compound was obtained as colorless crystals from ethyl 3-[4-({2',6'-dimethyl-4'-[(3-thienylsulfonyl)oxy]biphenyl-3-yl}methoxy)-2-fluorophenyl]propanoate according to a method similar to the method of Example 2 (yield 44%).

MS m/z 541(MH$^+$)

Example 105 ethyl 3-(4-{[4'-(2-ethoxyethoxy)-6-methoxy-2',6'-dimethylbiphenyl-3-yl]methoxy}-2-fluorophenyl)propanoate

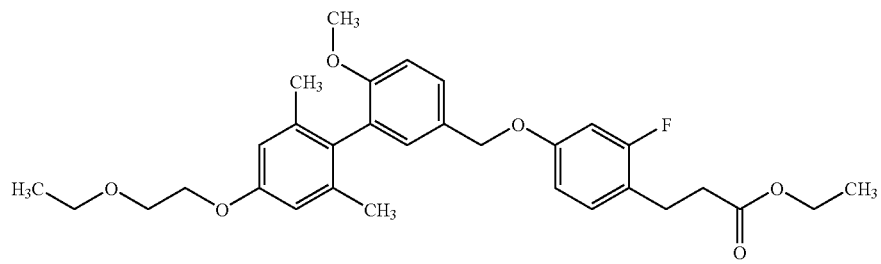

The title compound was obtained as a pale-yellow oil from ethyl 3-(2-fluoro-4-hydroxyphenyl)propanoate and [4'-(2-ethoxyethoxy)-6-methoxy-2',6'-dimethylbiphenyl-3-yl]methanol according to a method similar to the method of Example 1 (yield 88%).

MS (ESI+): 525 (M+H)

Example 106
3-(4-{[4'-(2-ethoxyethoxy)-6-methoxy-2',6'-dimethylbiphenyl-3-yl]methoxy}-2-fluorophenyl)propanoic acid

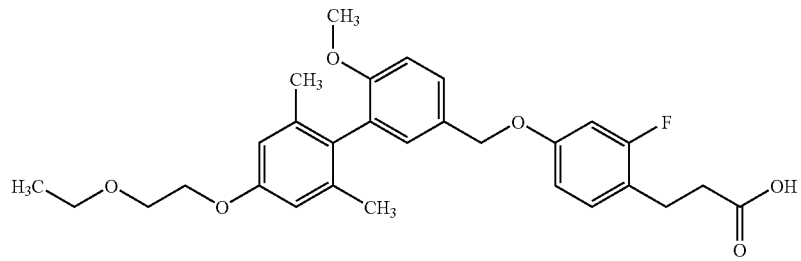

To a mixture of ethyl 3-(4-{[4'-(2-ethoxyethoxy)-6-methoxy-2',6'-dimethylbiphenyl-3-yl]methoxy}-2-fluorophenyl)propanoate (0.45 g, 0.86 mmol), methanol (4.5 mL) and tetrahydrofuran (9 mL) was added 1 N aqueous sodium hydroxide solution (1.7 mL) at room temperature with stirring and the mixture was stirred at the same temperature for 2 hrs. The reaction mixture was neutralized with 1 N hydrochloric acid and concentrated under reduced pressure. The residue was diluted with ethyl acetate, washed with water and saturated brine, dried and concentrated under reduced pressure. The residue was purified by silica gel column chromatography (hexane/ethyl acetate=2/1-hexane/ethyl acetate=1/2) to give the title compound (85 mg, yield 20%) as a colorless oil.
MS (ESI+): 497 (M+H)

Example 107
tert-butyl (2S)-2-{[(3'-{[4-(3-ethoxy-3-oxopropyl)-3-fluorophenoxy]methyl}-2,6-dimethylbiphenyl-4-yl)oxy]methyl}pyrrolidine-1-carboxylate

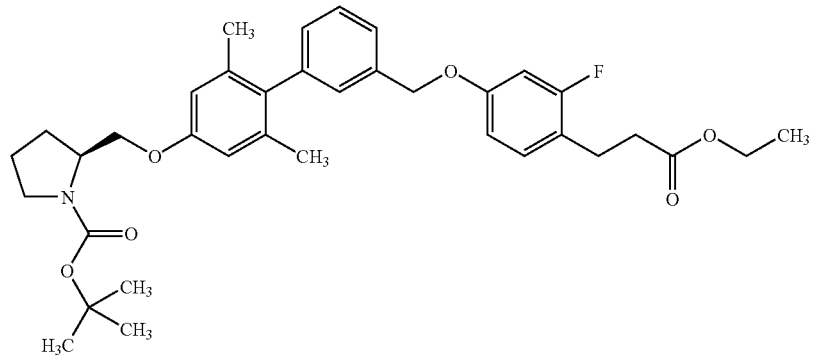

The title compound was obtained as a colorless oil from ethyl 3-{2-fluoro-4-[(4'-hydroxy-2',6'-dimethylbiphenyl-3-yl)methoxy]phenyl}propanoate and tert-butyl (2S)-2-(hydroxymethyl)pyrrolidine-1-carboxylate according to a method similar to the method of Example 1 (yield 8.6%).
$^1$H NMR (CDCl$_3$) δ: 1.23(3H, t, J=7.4 Hz), 1.48(9H, s), 1.70-2.10(4H, m), 1.98(6H, s), 2.57(2H, t, J=7.6 Hz), 2.90 (2H, t, J=7.6 Hz), 3.30-3.50(3H, m), 4.11(2H, q, J=7.4 Hz), 4.00-4.24(2H, m), 5.06(2H, s), 6.60-6.72(4H, m), 7.04-7.48 (5H, m).

Example 108
3-{4-[(4'-{[(2S)-1-(tert-butoxycarbonyl)pyrrolidin-2-yl]methoxy}-2',6'-dimethylbiphenyl-3-yl)methoxy]-2-fluorophenyl}propanoic acid

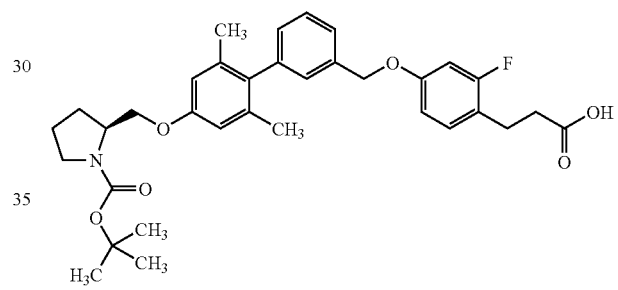

The title compound was obtained as a colorless solid from tert-butyl (2S)-2-{[(3'-{[4-(3-ethoxy-3-oxopropyl)-3-fluorophenoxy]methyl}-2,6-dimethylbiphenyl-4-yl)oxy]methyl}pyrrolidine-1-carboxylate according to a method similar to the method of Example 2 (yield 61%).

MS (APCI-): 576 (M-H)

Example 109 ethyl 3-[4-({2',6'-dimethyl-4'-[(6-methylpyridin-2-yl)oxy]biphenyl-3-yl}methoxy)-2-fluorophenyl]propanoate

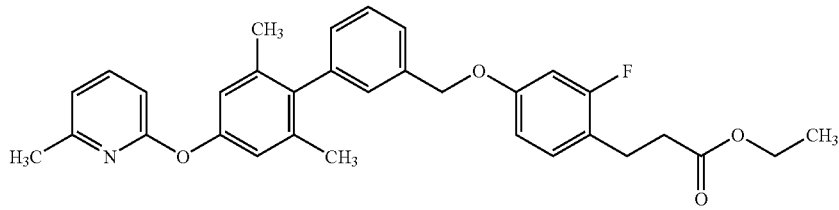

The title compound was obtained as a colorless oil from ethyl 3-(2-fluoro-4-hydroxyphenyl)propanoate and {2',6'-dimethyl-4'-[(6-methylpyridin-2-yl)oxy]biphenyl-3-yl}methanol according to a method similar to the method of Example 1 (yield 94%).

MS (ESI+): 514 (M+H)

Example 110

3-[4-({2',6'-dimethyl-4'-[(6-methylpyridin-2-yl)oxy]biphenyl-3-yl}methoxy)-2-fluorophenyl]propanoic acid

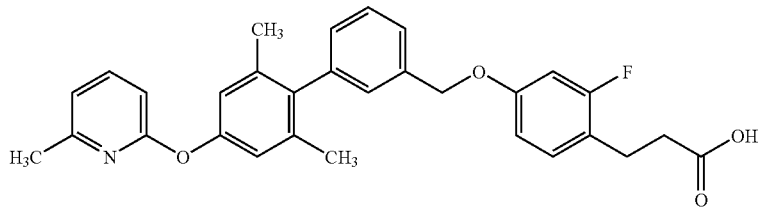

The title compound was obtained as a colorless oil from ethyl 3-[4-({2',6'-dimethyl-4'-[(6-methylpyridin-2-yl)oxy]biphenyl-3-yl}methoxy)-2-fluorophenyl]propanoate according to a method similar to the method of Example 106 (yield 62%).

MS (ESI+): 486 (M+H)

Example 111

3-[4-({2',6'-dimethyl-4'-[(6-methylpyridin-2-yl)oxy]biphenyl-3-yl}methoxy)-2-fluorophenyl]propanoic acid hydrochloride

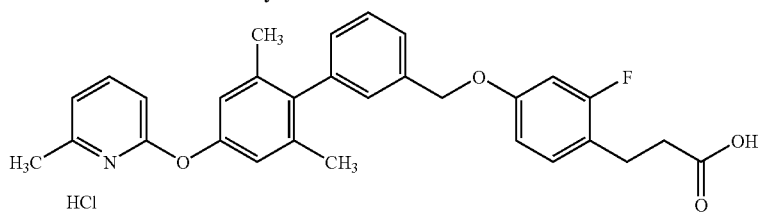

The title compound was obtained as colorless crystals from 3-[4-({2',6'-dimethyl-4'-[(6-methylpyridin-2-yl)oxy]biphenyl-3-yl}methoxy)-2-fluorophenyl]propanoic acid according to a method similar to the method of Example 79 (yield 83%).

MS (ESI+): 486 (M+H, as a free form)

Example 112 ethyl 3-(4-{[2',6'-dimethyl-4'-(tetrahydro-2H-thiopyran-4-yloxy)biphenyl-3-yl]methoxy}-2-fluorophenyl)propanoate

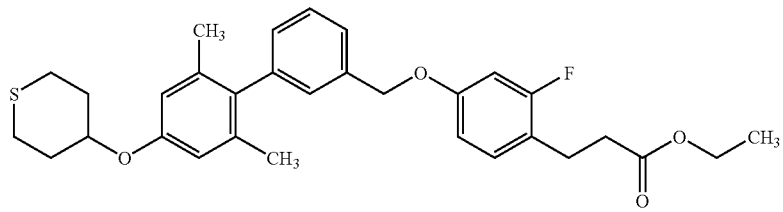

To a solution of ethyl 3-{2-fluoro-4-[(4'-hydroxy-2',6'-dimethylbiphenyl-3-yl)methoxy]phenyl}propanoate (0.50 g, 1.18 mmol), tetrahydro-2H-thiopyran-4-ol (0.15 g, 1.30 mmol) and triphenylphosphine (0.31 g, 1.30 mmol) in tetrahydrofuran (10 mL) was added diethyl azodicarboxylate (40% toluene solution, 0.70 mL, 1.53 mmol) at room temperature with stirring. The reaction mixture was stirred at room temperature for 19 hrs., and an equivalent amount of the aforementioned reagents (tetrahydro-2H-thiopyran-4-ol, triphenylphosphine and diethyl azodicarboxylate) were added. The mixture was further stirred at the same temperature for 6 hrs. The reaction mixture was concentrated under reduced pressure, and the residue was purified by silica gel column chromatography (hexane/ethyl acetate=10/1-hexane/ethyl acetate=3/1) to give the title compound (0.53 g, yield 91%) as a yellow oil.

$^1$H NMR (CDCl$_3$) δ: 1.23 (3H, t, J=7.1 Hz), 1.98 (6H, s), 1.99-2.11 (2H, m), 2.16-2.27 (2H, m), 2.53-2.64 (4H, m), 2.85-3.01 (4H, m), 4.07-4.17 (2H, m), 4.32-4.42 (1H, m), 5.06 (2H, s), 6.62-6.71 (4H, m), 7.05-7.12 (2H, m), 7.17 (1H, s), 7.34-7.46 (2H, m).

Example 113 ethyl 3-[4-({4'-[(1,1-dioxidotetrahydro-2H-thiopyran-4-yl)oxy]-2',6'-dimethylbiphenyl-3-yl}methoxy)-2-fluorophenyl]propanoate

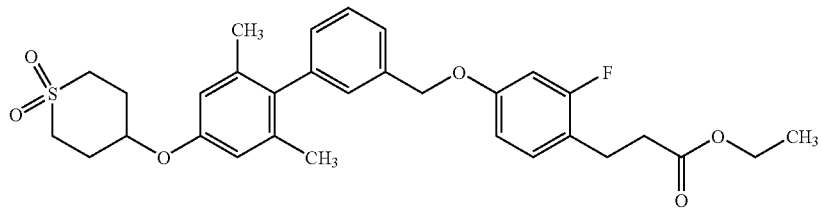

The title compound was obtained as a pale-yellow oil from ethyl 3-(4-{[2',6'-dimethyl-4'-(tetrahydro-2H-thiopyran-4-yloxy)biphenyl-3-yl]methoxy}-2-fluorophenyl)propanoate according to a method similar to the method of Example 71, except for using ethyl acatate instead of dichloromethane (yield 45%).

MS (ESI+): 555 (M+H)

Example 114

3-[4-({4'-[(1,1-dioxidotetrahydro-2H-thiopyran-4-yl)oxy]-2',6'-dimethylbiphenyl-3-yl}methoxy)-2-fluorophenyl]propanoic acid

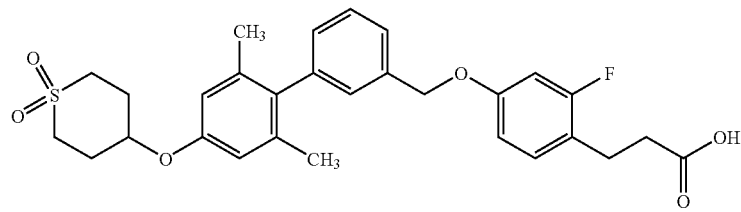

The title compound was obtained as colorless crystals from ethyl 3-[4-({4'-[(1,1-dioxidotetrahydro-2H-thiopyran-4-yl)oxy]-2',6'-dimethylbiphenyl-3-yl}methoxy)-2-fluorophenyl]propanoate according to a method similar to the method of Example 37 (yield 68%).
MS (ESI+): 527 (M+H).
m.p.: 148-149° C.

Example 115 ethyl 3-[4-({2',6'-dimethyl-4'-[(3-methyloxetan-3-yl)methoxy]biphenyl-3-yl}methoxy)-2-fluorophenyl]propanoate

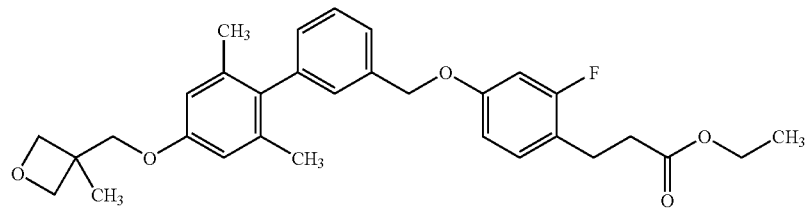

The title compound was obtained as a colorless oil from ethyl 3-{2-fluoro-4-[(4'-hydroxy-2',6'-dimethylbiphenyl-3-yl)methoxy]phenyl}propanoate and 3-methyl-3-oxetanemethanol according to a method similar to the method of Example 70 (yield 92%).
MS (ESI+): 507 (M+H)

Example 116

3-[4-({2',6'-dimethyl-4'-[(3-methyloxetan-3-yl)methoxy]biphenyl-3-yl}methoxy)-2-fluorophenyl]propanoic acid

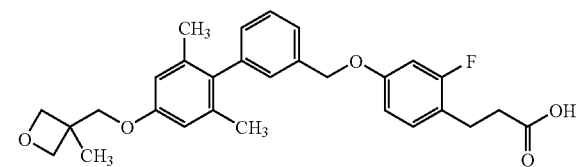

The title compound was obtained as colorless crystals from ethyl 3-[4-({2',6'-dimethyl-4'-[(3-methyloxetan-3-yl)meth oxy]biphenyl-3-yl}methoxy)-2-fluorophenyl]propanoate according to a method similar to the method of Example 37 (yield 67%).
MS (ESI+): 479 (M+H).
m.p.: 112-113° C.

Example 117 ethyl 3-(4-{[2',6'-dimethyl-4'-(tetrahydro-2H-pyran-4-yloxy)biphenyl-3-yl]methoxy}-2-fluorophenyl) propanoate

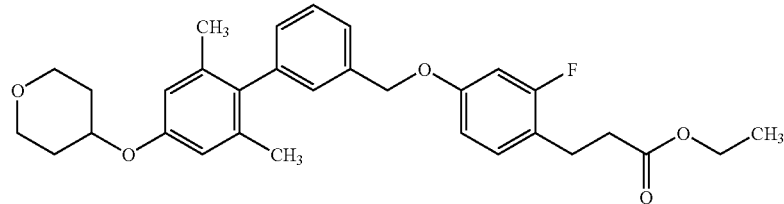

The title compound was obtained as a colorless oil from ethyl 3-{2-fluoro-4-[(4'-hydroxy-2',6'-dimethylbiphenyl-3-yl)methoxy]phenyl}propanoate and tetrahydro-2H-pyran-4-ol according to a method similar to the method of Example 112 (yield 97%).
MS (ESI+): 507 (M+H)

Example 118

3-(4-{[2',6'-dimethyl-4'-(tetrahydro-2H-pyran-4-yloxy)biphenyl-3-yl]methoxy}-2-fluorophenyl)propanoic acid

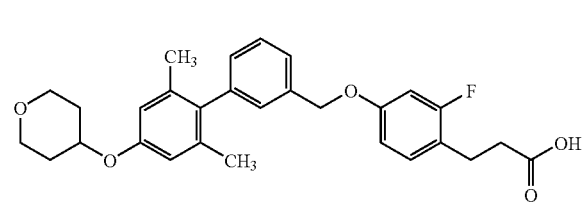

The title compound was obtained as colorless crystals from ethyl 3-(4-{[2',6'-dimethyl-4'-(tetrahydro-2H-pyran-4-yloxy)biphenyl-3-yl]methoxy}-2-fluorophenyl)propanoate according to a method similar to the method of Example 37 (yield 47%).

MS (ESI+): 479 (M+H).
m.p.: 123° C.

Example 119

3-(4-{[2',6'-dimethyl-4'-(tetrahydro-2H-thiopyran-4-yloxy)biphenyl-3-yl]methoxy}-2-fluorophenyl)propanoic acid

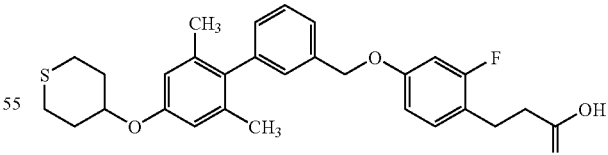

The title compound was obtained as colorless crystals from ethyl 3-(4-{[2',6'-dimethyl-4'-(tetrahydro-2H-thiopyran-4-yloxy)biphenyl-3-yl]methoxy}-2-fluorophenyl)propanoate according to a method similar to the method of Example 37 (yield 49%).
MS m/z 495(MH⁺)

Example 120 ethyl 3-[4-({4'-[3-(diethoxyphosphoryl)propoxy]-2',6'-dimethylbiphenyl-3-yl}methoxy)-2-fluorophenyl]propanoate

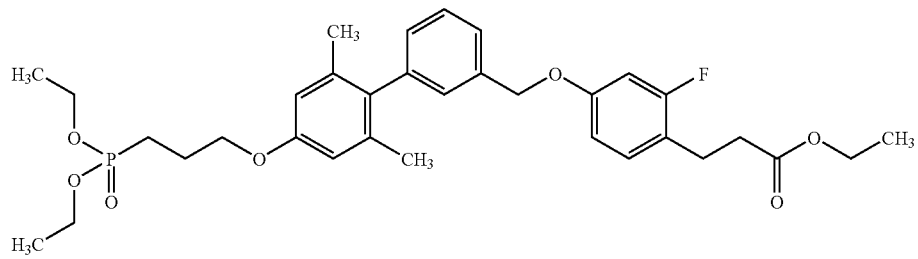

To a solution of ethyl 3-{2-fluoro-4-[(4'-hydroxy-2',6'-dimethylbiphenyl-3-yl)methoxy]phenyl}propanoate (315 mg, 0.74 mmol) in N,N-dimethylformamide (4 mL) was added sodium hydride (60%, 31 mg, 0.78 mmol) at 0° C. with stirring, and the mixture was stirred at room temperature for 30 min. Diethyl (3-bromopropyl)phosphonate (578 mg, 2.23 mmol) and potassium iodide (37 mg, 0.22 mmol) were added, and the mixture was further stirred overnight at 60° C. The reaction mixture was concentrated under reduced pressure. Brine was added to the residue, and the mixture was extracted with ethyl acetate. The extract was dried over anhydrous sodium sulfate and concentrated under reduced pressure. The residue was purified by silica gel column chromatography (hexane/ethyl acetate=10/1-1/4) and then by preparative HPLC (gradient cycle A) to give the title compound (0.22 g, yield 50%) as a colorless oil.

MS m/z 601 (MH$^+$)

Example 121

3-[4-({4'-[3-(diethoxyphosphoryl)propoxy]-2',6'-dimethylbiphenyl-3-yl}methoxy)-2-fluorophenyl]propanoic acid

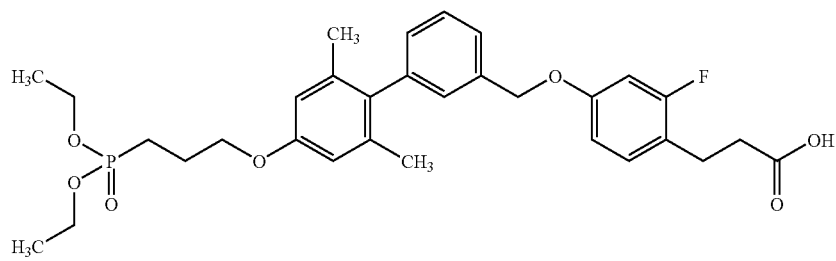

The title compound was obtained as a colorless oil from ethyl 3-[4-({4'-[3-(diethoxyphosphoryl)propoxy]-2',6'-dimethylbiphenyl-3-yl}methoxy)-2-fluorophenyl]propanoate according to a method similar to the method of Example 37 (yield 64%).

MS m/z 573 (MH$^+$).

$^1$H NMR (CDCl$_3$) δ: 1.33(6H, t, J=7.1 Hz), 1.85-2.19(10H, m) 2.62(2H, t, J=7.6 Hz), 2.90(2H, t, J=7.6 Hz), 4.03(2H, t, J=6.1 Hz), 4.06-4.22(4H, m), 5.06(2H, s), 6.60-6.72(4H, m), 7.03-7.18(3H, m), 7.32-7.47(2H, m).

Example 122 ethyl 3-{4-[(4'-{[tert-butyl(dimethyl)silyl]oxy}-6-isopropoxy-2',6'-dimethylbiphenyl-3-yl)methoxy]-2-fluorophenyl}propanoate

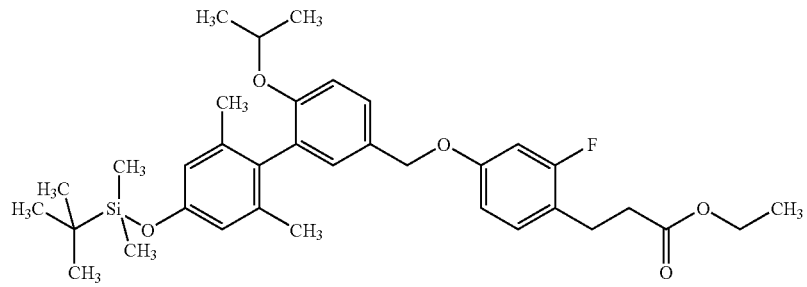

The title compound was obtained as a colorless oil from (4'-{[tert-butyl(dimethyl)silyl]oxy}-6-isopropoxy-2',6'-dimethylbiphenyl-3-yl)methanol and ethyl 3-(2-fluoro-4-hydroxyphenyl)propanoate according to a method similar to the method of Example 1 (yield 87%).

$^1$H NMR (CDCl$_3$) δ: 0.22(6H, s), 1.00(9H, s), 1.11(6H, d, J=6.0 Hz), 1.23(3H, t, J=7.2 Hz), 1.94(6H, s), 2.57(2H, t, J=7.6 Hz), 2.89(2H, t, J=7.6 Hz), 4.12(2H, q, J=7.2 Hz), 4.21-4.34(1H, m), 4.96(2H, s), 6.56(2H, s), 6.61-6.72(2H, m), 6.96(1H, d, J=8.5 Hz), 7.04-7.13(2H, m), 7.31(1H, dd, J=8.4, 2.4 Hz).

Example 123 ethyl 3-{2-fluoro-4-[(4'-hydroxy-6-isopropoxy-2',6'-dimethylbiphenyl-3-yl)methoxy]phenyl}propanoate

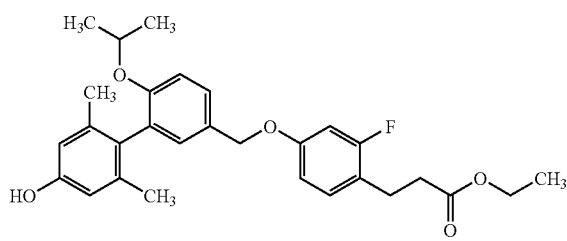

The title compound was obtained as a colorless oil from ethyl 3-{4-[(4'-{[tert-butyl(dimethyl)silyl]oxy}-6-isopropoxy-21,6'-dimethylbiphenyl-3-yl)methoxy]-2-fluorophenyl}propanoate according to a method similar to the method of Example 57 (yield 80%).

MS m/z 481 (MH$^+$)

Example 124 ethyl 3-[2-fluoro-4-({6-isopropoxy-2',6'-dimethyl-4'-[(3-methyloxetan-3-yl)methoxy]biphenyl-3-yl}methoxy)phenyl]propanoate

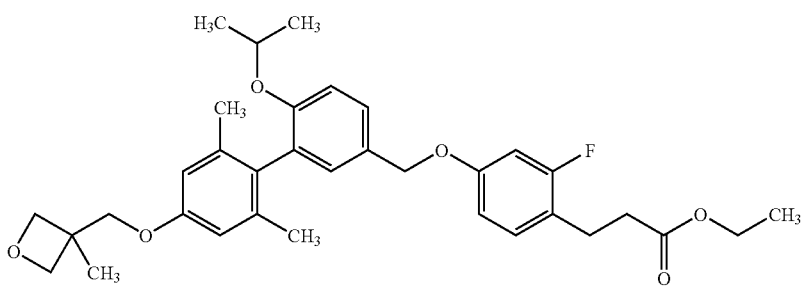

The title compound was obtained as a colorless oil from ethyl 3-{2-fluoro-4-[(4'-hydroxy-6-isopropoxy-2',6'-dimethylbiphenyl-3-yl)methoxy]phenyl}propanoate and 3-methyl-3-oxetanemethanol according to a method similar to the method of Example 70 (yield 72%).

MS m/z 565 (MH$^+$)

Example 125

3-[2-fluoro-4-({6-isopropoxy-2',6'-dimethyl-4'-[(3-methyloxetan-3-yl)methoxy]biphenyl-3-yl}methoxy)phenyl]propanoic acid

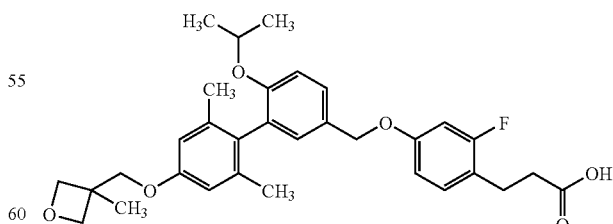

The title compound was obtained as a colorless amorphous powder from ethyl 3-[2-fluoro-4-({6-isopropoxy-2',6'-dimethyl-4'-[(3-methyloxetan-3-yl)methoxy]biphenyl-3-yl}methoxy)phenyl]propanoate according to a method similar to the method of Example 37 (yield 87%).

MS m/z 537 (MH$^+$).

$^1$H NMR (CDCl$_3$) δ: 1.15(6H, d, J=6.0 Hz), 1.45(3H, s), 1.98(6H, s), 2.64(2H, t, J=7.7 Hz), 2.90(2H, t, J=7.6 Hz), 4.04(2H, s), 4.31-4.41(1H, m), 4.47(2H, d, J=5.8 Hz), 4.66 (2H, d, J=5.8 Hz), 4.96(2H, s), 6.61-6.72(4H, m), 6.96(1H, d, J=8.5 Hz), 7.03-7.14(2H, m), 7.32(1H, dd, J=8.5, 2.3 Hz).

Formulation Example 1 (Production of Capsule)

| | |
|---|---|
| 1) compound of Example 1 | 30 mg |
| 2) microcrystalline cellulose | 10 mg |
| 3) lactose | 19 mg |
| 4) magnesium stearate | 1 mg |
| total | 60 mg |

The above-mentioned 1), 2), 3) and 4) are mixed and filled in a gelatin capsule.

Formulation Example 2 (Production of Tablet)

| | |
|---|---|
| 1) compound of Example 1 | 30 g |
| 2) lactose | 50 g |
| 3) corn starch | 15 g |
| 4) carboxymethylcellulose calcium | 44 g |
| 5) magnesium stearate | 1 g |
| 1000 tablets total | 140 g |

The total amount of the above-mentioned 1), 2) and 3) and 30 g of 4) are kneaded with water, vacuum dried and granulated. The granulated powder is mixed with 14 g of 4) and 1 g of 5) and tableted with a tableting machine. In this way, 1000 tablets containing 30 mg of the compound of Example 1 per tablet are obtained.

Experimental Example 1

Determination of EC$_{50}$ of the Compound of the Present Invention Against Human GPR40

For determination of EC$_{50}$, CHO cell line that stably expressed human GPR40 was used. Unless otherwise indicated, the CHO cell line was cultured using α-MEM medium (Invitrogen) containing 10% fetal calf serum (Invitrogen).

The cells cultured to nearly confluent were rinsed with PBS (Invitrogen) on the previous day of the assay, peeled off with 0.05% Trypsin-EDTA solution (Invitrogen) and recovered by centrifugation. The number of the obtained cells was counted, and the cells were diluted such that 3×10$^5$ cells were contained per 1 mL of the medium, dispensed to a black welled 96-well plate (coster) by 100 μL per well and cultured overnight in a CO$_2$ incubator. Various test compounds were added to the CHO cells thus prepared, and the changes in the intracellular calcium concentration was measured using FLIPR (Molecular Device). The below-mentioned pre-treatment was applied to measure changes in the intracellular calcium concentration by FLIPR.

An assay buffer for adding a fluorescence dye Fluo3-AM (DOJIN) to the cells, or for washing the cells immediately before FLIPR assay was prepared. To a solution of 1M HEPES (pH 7.4, DOJIN, 20 mL) added to HBSS (Invitrogen, 1000 mL) (hereinafter HBSS/HEPES solution) was added a solution (10 mL) obtained by dissolving probenecid (Sigma, 710 mg) in 1N NaOH (5 mL), and adding and mixing an HBSS/HEPES solution (5 mL), and the resulting solution was used as assay buffer. Fluo3-AM (50 μg) was dissolved in dimethylsulfoxide (Wako, 21 μL), and an equivalent amount of 20% pluronic acid (Molecular Probes) was added and mixed. The solution was added to the assay buffer (10.6 mL) supplemented with fetal calf serum (105 μL) to give a fluorescence dye solution. On the previous day of assay, the medium of the CHO cells newly inoculated to the black welled 96-well plate was removed, the fluorescence dye solution was immediately dispensed by 100 μL per well and the cells were cultured in a CO$_2$ incubator for 1 hr to allow intake of the fluorescence dye by the cells. The cells after the culture were washed with the above-mentioned assay buffer and set on FLIPR. The test compound was diluted with dimethylsulfoxide in advance, dispensed to polypropylene 96-well plate (sample plate) by 2 μL, and cryopreserved at −20° C. To the thawed sample plate was added an assay buffer containing 0.015% CHAPS (DOJIN) by 198 μL, and simultaneously set on FLIPR together with the cell plate. After the aforementioned pre-treatment, changes in the intracellular calcium concentration upon addition of various test compounds was measured by FLIPR. Based on the results, a dose-response curve of each test compound was formed and EC$_{50}$ was calculated. The results are shown in Table 1.

TABLE 1

| Receptor Function Modulating Action On GPR40 | |
|---|---|
| Compound No. | EC$_{50}$ (μM) |
| Example 14 | 0.010 |
| Example 33 | 0.0061 |
| Example 39 | 0.032 |
| Example 49 | 0.011 |
| Example 54 | 0.049 |
| Example 75 | 0.016 |
| Example 86 | 0.032 |
| Example 90 | 0.034 |
| Example 97 | 0.023 |
| Example 100 | 0.017 |
| Example 102 | 0.015 |
| Example 114 | 0.02 |

INDUSTRIAL APPLICABILITY

The compound (I), a salt thereof and a prodrug thereof have a superior GPR40 receptor function modulating action and can be used as an agent for the prophylaxis or treatment of diabetes and the like.

This application is based on patent application Nos. 431629/2003 and 241484/2004 filed in Japan, the content of which is hereby incorporated by reference.

The invention claimed is:

1. A compound represented by the formula (I):

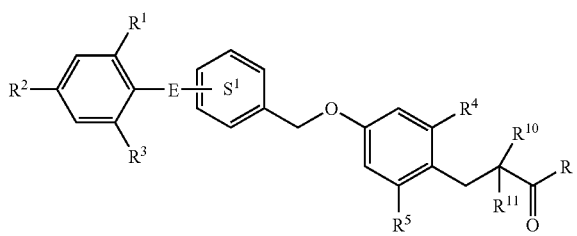

wherein $R^1$, $R^3$, $R^4$ and $R^5$ are the same or different and each is a hydrogen atom, a halogen atom, optionally substituted $C_{1-6}$ alkyl group, optionally substituted $C_{2-6}$ alkenyl group, optionally substituted $C_{2-6}$ alkynyl group, optionally substituted $C_{3-8}$ cycloalkyl group, optionally substituted $C_{6-14}$ aryl group, optionally substituted $C_{7-16}$ aralkyl group or an optionally substituted hydroxy group;

R² is a halogen atom, a nitro group, optionally substituted $C_{1-6}$ alkyl group, optionally substituted $C_{2-6}$ alkenyl group, optionally substituted $C_{2-6}$ alkynyl group, optionally substituted $C_{3-8}$ cycloalkyl group, optionally substituted $C_{6-14}$ aryl group, optionally substituted $C_{7-16}$ aralkyl group, an optionally substituted hydroxy group, an optionally substituted amino group, an optionally substituted mercapto group, an optionally substituted acyl group or an optionally substituted heterocyclic group;

$R^{10}$ and $R^{11}$ are the same or different and each is a hydrogen atom, a halogen atom or a $C_{1-6}$ alkoxy group;

E is a bond, an optionally substituted $C_{1-4}$ alkylene group, $-W^1-O-W^2-$, $-W^1-S-W^2-$ or $-W^1-N(R^6)-W^2-$ (wherein $W^1$ and $W^2$ are the same or different and each is a bond or an optionally substituted $C_{1-3}$ alkylene group, and $R^6$ is a hydrogen atom, an optionally substituted acyl group, optionally substituted $C_{1-6}$ alkyl group, optionally substituted $C_{2-6}$ alkenyl group, optionally substituted $C_{2-6}$ alkynyl group, optionally substituted $C_{3-8}$ cycloalkyl group, optionally substituted $C_{6-14}$ aryl group or optionally substituted $C_{7-16}$ aralkyl group);

ring $S^1$ is a benzene ring optionally further having substituent(s) selected from a halogen atom, optionally substituted $C_{1-6}$ alkyl group, optionally substituted $C_{2-6}$ alkenyl group, optionally substituted $C_{2-6}$ alkynyl group, optionally substituted $C_{3-8}$ cycloalkyl group, optionally substituted $C_{6-14}$ aryl group, optionally substituted $C_{7-16}$ aralkyl group, an optionally substituted hydroxy group and an optionally substituted amino group; and R is an optionally substituted hydroxy group or an optionally substituted amino group;

provided that $R^1$ and $R^3$ are not simultaneously a hydrogen atom, or a salt thereof.

2. The compound of claim 1, wherein $R^2$ is a halogen atom, an optionally substituted hydrocarbon group, an optionally substituted hydroxy group, an optionally substituted amino group, an optionally substituted mercapto group or an optionally substituted heterocyclic group, and $R^{10}$ and $R^{11}$ are both hydrogen atoms, or a salt thereof.

3. The compound of claim 1, wherein $R^4$ and $R^5$ are the same or different and each is a hydrogen atom or a halogen atom, or a salt thereof.

4. The compound of claim 1, wherein E is a bond, or a salt thereof.

5. The compound of claim 1, wherein R is a hydroxy group, or a salt thereof.

6. The compound of claim 1, wherein $R^1$ and $R^3$ are the same or different and each is a $C_{1-6}$ alkyl group, or a salt thereof.

7. The compound of claim 1, wherein $R^2$ is an optionally substituted hydroxy group, or a salt thereof.

8. The compound of claim 1, wherein $R^{10}$ and $R^{11}$ are both hydrogen atoms, or a salt thereof.

9. The compound of claim 1, wherein ring $S^1$ is a benzene ring optionally further having a $C_{1-6}$ alkoxy group, or a salt thereof.

10. 3-[4-[[4'-(benzyloxy)-2',6'-dimethylbiphenyl-3-yl]methoxy]phenyl]propanoic acid;

3-(4-{[4'-(2-ethoxyethoxy)-2',6'-dimethylbiphenyl-3-yl]methoxy}phenyl)-2,2-difluoropropanoic acid;

3-[4-({4'-[2-(ethylsulfonyl)ethoxy]-2',6'-dimethylbiphenyl-3-yl}methoxy)-2-fluorophenyl]propanoic acid;

3-[4-({2',6'-dimethyl-4'-[3-(2-oxopyrrolidin-1-yl)propoxy]biphenyl-3-yl}methoxy)-2-fluorophenyl]propanoic acid;

3-[4-({2',6'-dimethyl-4'-[(6-methylpyridin-2-yl)methoxy]biphenyl-3-yl}methoxy)-2-fluorophenyl]propanoic acid;

3-[2-fluoro-4-({4'-[(4-hydroxy-1,1-dioxidotetrahydro-2H-thiopyran-4-yl)methoxy]-2',6'-dimethylbiphenyl-3-yl}methoxy)phenyl]propanoic acid;

3-[4-({2',6'-dimethyl-4'-[(methylsulfonyl)oxy]biphenyl-3-yl}methoxy)-2-fluorophenyl]propanoic acid;

3-[4-({4'-[(1,1-dioxidotetrahydro-2H-thiopyran-4-yl)oxy]-2',6'-dimethylbiphenyl-3-yl}methoxy)-2-fluorophenyl]propanoic acid;

3-[4-({2',6'-dimethyl-4'-[(3-methyloxetan-3-yl)methoxy]biphenyl-3-yl}methoxy)-2-fluorophenyl]propanoic acid;

3-(4-{[2',6'-dimethyl-4'-(tetrahydro-2H-pyran-4-yloxy)biphenyl-3-yl]methoxy}-2-fluorophenyl)propanoic acid;

3-[4-({4'-[3-(diethoxyphosphoryl)propoxy]-2',6'-dimethylbiphenyl-3-yl}methoxy)-2-fluorophenyl]propanoic acid;

3-[2-fluoro-4-({6-isopropoxy-2',6'-dimethyl-4'-[(3-methyloxetan-3-yl)methoxy]biphenyl-3-yl}methoxy)phenyl]propanoic acid;

or a salt thereof.

11. A pharmaceutical agent comprising a compound of claim 1 or a salt thereof.

12. A method for the production of an agent for the treatment of diabetes, which comprises mixing a compound of claim 1 or a salt thereof with a pharmaceutically acceptable carrier.

13. A method for the treatment of diabetes in a mammal, which comprises administering an effective amount of a compound of claim 1 or a salt thereof to the mammal.

14. A production method of a compound represented by the formula (Ib):

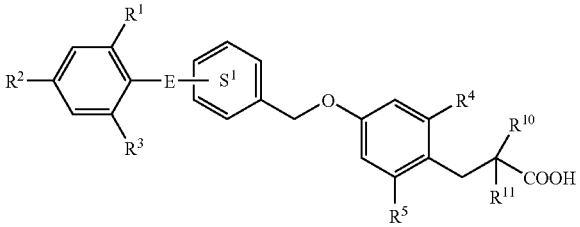

(Ib)

wherein $R^1$, $R^3$, $R^4$ and $R^5$
are the same or different and each is a hydrogen atom, a halogen atom, optionally substituted $C_{1-6}$ alkyl group, optionally substituted $C_{2-6}$ alkenyl group, optionally substituted $C_{2-6}$ alkynyl group, optionally substituted $C_{3-8}$ cycloalkyl group, optionally substituted $C_{6-14}$ aryl group, optionally substituted $C_{7-16}$ aralkyl group or an optionally substituted hydroxy group;

$R^2$ is a halogen atom, a nitro group, optionally substituted $C_{1-6}$ alkyl group, optionally substituted $C_{2-6}$ alkenyl group, optionally substituted $C_{2-6}$ alkynyl group, optionally substituted $C_{3-8}$ cycloalkyl group, optionally substituted $C_{6-14}$ aryl group, optionally substituted $C_{7-16}$ aralkyl group, an optionally substituted hydroxy group, an optionally substituted amino group, an optionally substituted mercapto group, an optionally substituted acyl group or an optionally substituted heterocyclic group;

$R^{10}$ and $R^{11}$ are the same or different and each is a hydrogen atom, a halogen atom or a $C_{1-6}$ alkoxy group;

E is a bond, an optionally substituted $C_{1-4}$ alkylene group, $-W^1-O-W^2-$, $-W^1-S-W^2-$ or $-W^1-N(R^6)-W^2-$ (wherein $W^1$ and $W^2$ are the same or different and each is a bond or an optionally substituted $C_{1-3}$ alkylene group, and $R^6$ is a hydrogen atom, an optionally substituted acyl group, optionally substituted $C_{1-6}$ alkyl group, optionally substituted $C^{2-6}$ alkenyl group, optionally substituted $C_{2-6}$ alkynyl group, optionally substituted $C_{3-8}$ cycloalkyl group, optionally substituted $C_{6-14}$ aryl group, optionally substituted $C_{7-16}$ aralkyl group);

ring $S^1$ is a benzene ring optionally further having substituent(s) selected from a halogen atom, optionally substituted $C_{1-6}$ alkyl group, optionally substituted $C_{2-6}$ alkenyl group, optionally substituted $C_{2-6}$ alkynyl group, optionally substituted $C_{3-8}$ cycloalkyl group, optionally substituted $C_{6-14}$ aryl group, optionally substituted $C_{7-16}$ aralkyl group, an optionally substituted hydroxy group and an optionally substituted amino group; and provided that $R^1$ and $R^3$ are not simultaneously a hydrogen atom, or a salt thereof, which comprises reacting a compound represented by the formula (X)

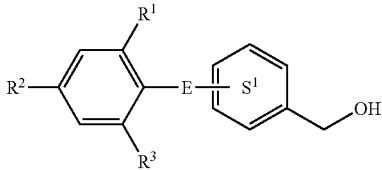

(X)

wherein each symbol is as defined above, or a salt thereof, and a compound represented by the formula (II):

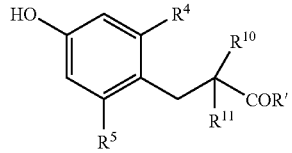

(II)

wherein $R^4$, $R^5$, $R^{10}$ and $R^{11}$ are as defined above, and R' is an optionally substituted $C_{1-6}$ alkoxy group, or a salt thereof, to give a compound represented by the formula (Ib'):

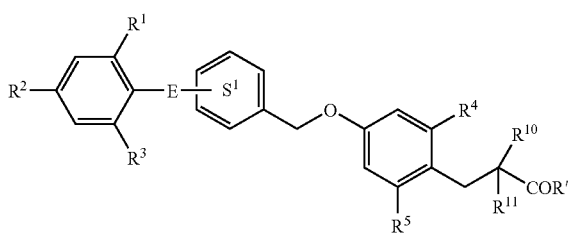

(Ib')

wherein each symbol is as defined above, or a salt thereof, and subjecting the compound or a salt thereof to a hydrolysis reaction.

15. A production method of a compound represented by the formula (Id):

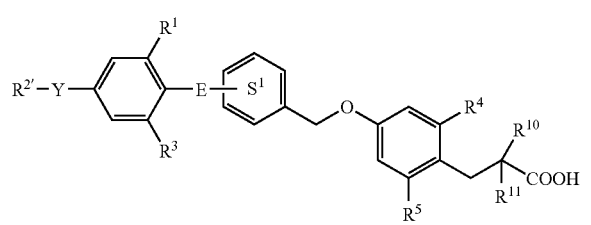

(Id)

wherein $R^1$, $R^3$, $R^4$ and $R^5$
are the same or different and each is a hydrogen atom, a halogen atom, optionally substituted $C_{1-6}$ alkyl group, optionally substituted $C_{2-6}$ alkenyl group, optionally substituted $C_{2-6}$ alkynyl group, optionally substituted $C_{3-8}$ cycloalkyl group, optionally substituted $C_{6-14}$ aryl group, optionally substituted $C_{7-16}$ aralkyl group or an optionally substituted hydroxy group;

$R^{10}$ and $R^{11}$ are the same or different and each is a hydrogen atom, a halogen atom or a $C_{1-6}$ alkoxy group;

E is a bond, an optionally substituted $C_{1-4}$ alkylene group, —$W^1$—O—$W^2$—, —$W^1$—S—$W^2$— or —$W^1$—N($R^6$)—$W^2$— (wherein $W^1$ and $W^2$ are the same or different and each is a bond or an optionally substituted $C_{1-3}$ alkylene group, and $R^6$ is a hydrogen atom, an optionally substituted acyl group, optionally substituted $C_{1-6}$ alkyl group, optionally substituted $C_{2-6}$ alkenyl group, optionally substituted $C_{2-6}$ alkynyl group, optionally substituted $C_{3-8}$ cycloalkyl group, optionally substituted $C_{6-14}$ aryl group, optionally substituted $C_{7-16}$ aralkyl group);

ring $S^1$ is a benzene ring optionally further having substituent(s) selected from a halogen atom, optionally substituted $C_{1-6}$ alkyl group, optionally substituted $C_{2-6}$ alkenyl group, optionally substituted $C_{2-6}$ alkynyl group, optionally substituted $C_{3-8}$ cycloalkyl group, optionally substituted $C_{6-14}$ aryl group, optionally substituted $C_{7-16}$ aralkyl group, an optionally substituted hydroxy group and an optionally substituted amino group;

provided that $R^1$ and $R^3$ are not simultaneously a hydrogen atom,

Y is —O— or —S—, and $R^{2'}$ is a substituent, or a salt thereof, which comprises reacting a compound represented by the formula (Ie'):

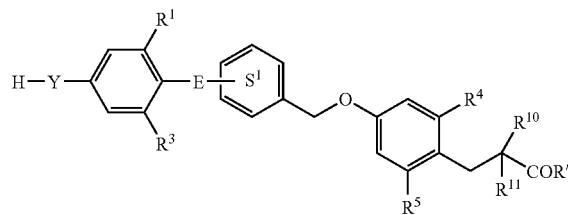

(Ie')

wherein $R^1$, $R^3$, $R^4$, $R^5$, $R^{10}$, $R^{11}$, E, Y and ring $S^1$ are as defined above, R' is an optionally substituted $C_{1-6}$ alkoxy group, or a salt thereof, and a compound represented by the formula:

$R^{2'}$—OH wherein $R^{2'}$ is as defined above, or a salt thereof, to give a compound represented by the formula (If'):

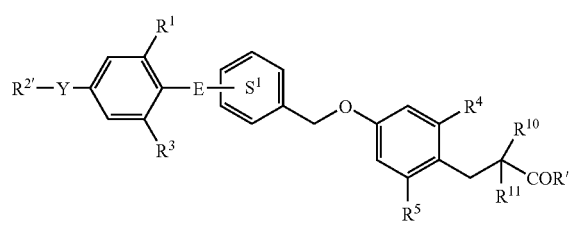

(If')

wherein each symbol is as defined above, or a salt thereof, and subjecting the compound or a salt thereof to a hydrolysis reaction.

* * * * *